(12) United States Patent
Towfigh

(10) Patent No.: US 11,602,425 B2
(45) Date of Patent: Mar. 14, 2023

(54) GENDER-SPECIFIC MESH IMPLANT WITH BARRIER FOR INGUINAL HERNIA REPAIR

(71) Applicant: Hexagon Health, Inc., Beverly Hills, CA (US)

(72) Inventor: Shirin Towfigh, Beverly Hills, CA (US)

(73) Assignee: Hexagon Health, Inc., Beverly Hills, CA (US)

( * ) Notice: Subject to any disclaimer, the term of this patent is extended or adjusted under 35 U.S.C. 154(b) by 442 days.

(21) Appl. No.: 16/549,941

(22) Filed: Aug. 23, 2019

(65) Prior Publication Data

US 2020/0054429 A1 Feb. 20, 2020

Related U.S. Application Data

(63) Continuation of application No. 15/202,440, filed on Jul. 5, 2016, now Pat. No. 10,433,943, which is a (Continued)

(51) Int. Cl.
*A61F 2/00* (2006.01)

(52) U.S. Cl.
CPC .... *A61F 2/0063* (2013.01); *A61F 2002/0068* (2013.01); *A61F 2230/0004* (2013.01); (Continued)

(58) Field of Classification Search
CPC ............ A61F 2/0063; A61F 2230/0004; A61F 2250/0078; A61F 2002/0068; (Continued)

(56) References Cited

U.S. PATENT DOCUMENTS

| 2,671,444 A | 3/1954 | Pease, Jr. |
| 4,769,038 A | 9/1988 | Bendavid et al. |

(Continued)

FOREIGN PATENT DOCUMENTS

| CN | 202843850 U | 4/2013 |
| CN | 104039267 A | 9/2014 |

(Continued)

OTHER PUBLICATIONS

U.S. Appl. No. 16/549,924 Office Action dated Aug. 19, 2021.
(Continued)

*Primary Examiner* — Jing Rui Ou
(74) *Attorney, Agent, or Firm* — Goodwin Procter LLP

(57) ABSTRACT

Disclosed herein are gender-specific implantable mesh for inguinal hernia repair in a patient, comprising: a fabric layer comprising a side defining a surface area wherein the fabric layer is configured to enable tissue adhesion to said mesh; an anti-adhesive barrier comprising a shape configured to prevent direct contact between the fabric layer and both a spermatic cord and a genital nerve upon implantation, wherein the shape covers a part of the surface area on the side of the fabric layer, the part being less than 25%, and wherein the shape is oblique to a horizontally-oriented centerline and a vertically-oriented centerline; and a keyhole configured to fit the genital nerve and the spermatic cord of the patient therethrough without constriction, wherein the keyhole is oblique and inferior to a horizontally-oriented centerline and medial to a vertically-oriented centerline.

19 Claims, 19 Drawing Sheets

Related U.S. Application Data continuation of application No. PCT/US2016/024090, filed on Mar. 24, 2016.

(60) Provisional application No. 62/137,759, filed on Mar. 24, 2015.

(52) U.S. Cl.
CPC ............ *A61F 2230/0006* (2013.01); *A61F 2230/0008* (2013.01); *A61F 2230/008* (2013.01); *A61F 2230/0019* (2013.01); *A61F 2230/0021* (2013.01); *A61F 2230/0023* (2013.01); *A61F 2230/0026* (2013.01); *A61F 2230/0078* (2013.01); *A61F 2250/0078* (2013.01)

(58) Field of Classification Search
CPC ...... A61F 2230/0006; A61F 2230/0008; A61F 2230/0019; A61F 2230/0021; A61F 2230/0023; A61F 2230/0026; A61F 2230/0078; A61F 2230/008
See application file for complete search history.

(56) References Cited

U.S. PATENT DOCUMENTS

| | | | |
|---|---|---|---|
| 5,716,409 A | 2/1998 | Debbas | |
| 5,813,975 A | 9/1998 | Valenti | |
| 6,066,777 A | 5/2000 | Benchetrit | |
| 6,241,768 B1 | 6/2001 | Agarwal et al. | |
| 6,258,124 B1 | 7/2001 | Darois et al. | |
| 6,497,650 B1 | 12/2002 | Nicolo | |
| 6,610,006 B1 | 8/2003 | Amid et al. | |
| 6,652,595 B1 | 11/2003 | Nicolo | |
| 6,736,823 B2* | 5/2004 | Darois ............ | A61F 2/0063 623/23.72 |
| 6,755,781 B2 | 6/2004 | Gellman | |
| 10,433,943 B2 | 10/2019 | Owfigh | |
| 2002/0013590 A1 | 1/2002 | Therin et al. | |
| 2002/0072694 A1 | 6/2002 | Snitkin et al. | |
| 2003/0114866 A1 | 6/2003 | Ulmsten et al. | |
| 2003/0212460 A1 | 11/2003 | Darois et al. | |
| 2005/0250977 A1 | 11/2005 | Montpetit et al. | |
| 2006/0004444 A1 | 1/2006 | Ward | |
| 2006/0229493 A1* | 10/2006 | Weiser ............ | A61B 17/06109 600/37 |
| 2007/0055095 A1 | 3/2007 | Chu et al. | |
| 2008/0243149 A1 | 10/2008 | Kockerling et al. | |
| 2010/0152530 A1 | 6/2010 | Timmer et al. | |
| 2011/0190573 A1 | 8/2011 | Deegan | |
| 2012/0078274 A1 | 3/2012 | Nicolo | |
| 2012/0179175 A1 | 7/2012 | Hammell | |
| 2012/0185004 A1 | 7/2012 | Mcjames et al. | |
| 2012/0253366 A1 | 10/2012 | Darois et al. | |
| 2013/0030360 A1 | 1/2013 | Stopek et al. | |
| 2013/0035543 A1 | 2/2013 | Fischer et al. | |
| 2013/0204077 A1 | 8/2013 | Nagale et al. | |
| 2013/0211191 A1 | 8/2013 | Beyer | |
| 2013/0267970 A1 | 10/2013 | Cardinale et al. | |
| 2014/0025096 A1 | 1/2014 | Hamlin et al. | |
| 2014/0081296 A1 | 3/2014 | Palmer et al. | |
| 2014/0236197 A1* | 8/2014 | Bell ............ | A61B 17/0485 606/151 |
| 2020/0054428 A1 | 2/2020 | Towfigh | |
| 2020/0205958 A1 | 7/2020 | Towfigh | |
| 2021/0236256 A1 | 8/2021 | Towfigh | |
| 2021/0244521 A1 | 8/2021 | Towfigh | |

FOREIGN PATENT DOCUMENTS

| | | |
|---|---|---|
| CN | 203885665 U | 10/2014 |
| WO | WO-0108594 A1 | 2/2001 |
| WO | WO-2006032812 A2 | 3/2006 |
| WO | WO-2013098349 A1 | 7/2013 |
| WO | WO-2016154478 A1 | 9/2016 |

OTHER PUBLICATIONS

U.S. Appl. No. 16/814,720 Office Action dated Jul. 22, 2021.
U.S. Appl. No. 16/814,720 Office Action dated Mar. 8, 2021.
U.S. Appl. No. 16/814,720 Office Action dated Oct. 23, 2020.
U.S. Appl. No. 17/240,617 Office Action dated Aug. 4, 2021.
U.S. Appl. No. 17/240,627 Office Action dated Jul. 26, 2021.
Abdalla et al., Short Term Outcomes of Laparoscopic Totally Extraperitoneal Repair of Uncomplicated Groin Hernia Using Polyester Anatomical Mesh Without Fixation. The Journal of Surgery 5(6): 97-104 (2017).
Covidien European Product Catalog. Hernia Care. FY 2013.
U.S. Appl. No. 16/814,720 First Action Interview Pilot Program dated Aug. 20, 2020.
Amid, Parviz K. Lichtenstein tension-free hernioplasty: Its inception, evolution and principles. Hernia, 8(1); pp. 1-7 (Feb. 2004).
Co-pending U.S. Appl. No. 16/549,924, filed Aug. 23, 2019.
International Application No. PCT/US16/24090 International Search Report and Written Opinion dated Jun. 24, 2016.
International Application No. PCT/US2016/024090 International Preliminary Report on Patentability dated Oct. 5, 2017.
Singapore Application No. 11201707850P Search Report dated Aug. 16, 2018.
U.S. Appl. No. 15/202,440 Final Office Action dated Jan. 4, 2019.
U.S. Appl. No. 15/202,440 Final Office Action dated Oct. 17, 2017.
U.S. Appl. No. 15/202,440 Non-Final Office Action dated Apr. 7, 2017.
U.S. Appl. No. 15/202,440 Non-Final Office Action dated Jun. 22, 2018.

* cited by examiner

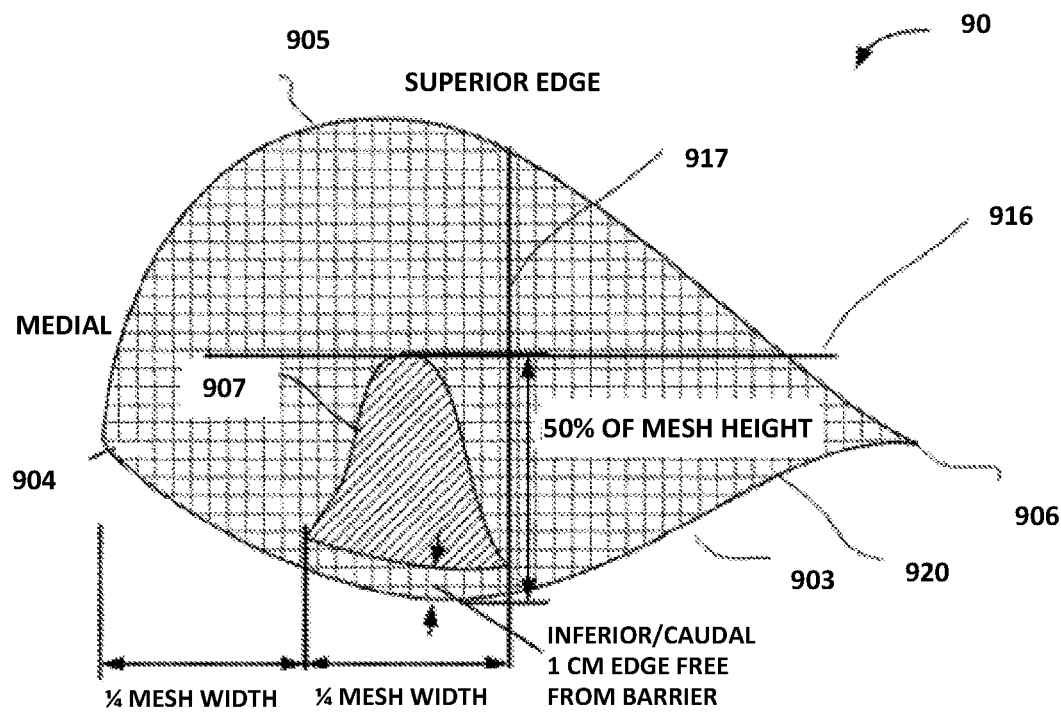
Fig. 9A
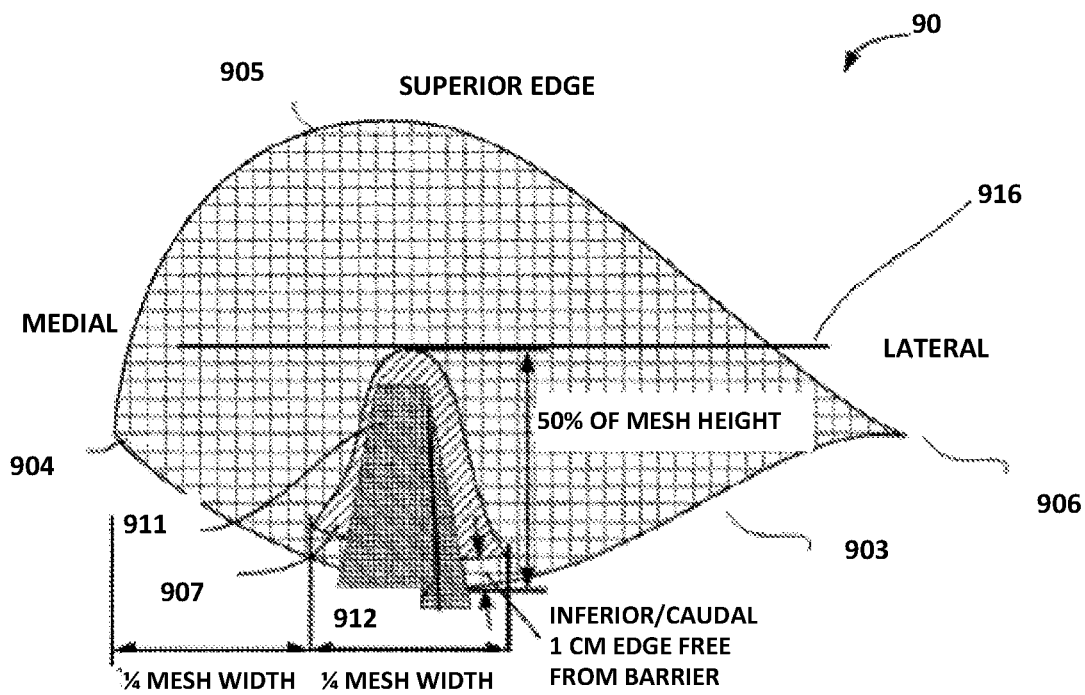

GENDER-SPECIFIC MESH IMPLANT WITH BARRIER FOR INGUINAL HERNIA REPAIR

CROSS-REFERENCE

This application is a continuation of U.S. application Ser. No. 15/202,440, filed Jul. 5, 2016, now U.S. Pat. No. 10,433,943, which is a continuation of International Application Number PCT/US2016/024090, filed Mar. 24, 2016, which claims the benefit of priority from U.S. Provisional Application No. 62/137,759, filed Mar. 24, 2015, all of which are incorporated herein by reference in their entirety.

BACKGROUND OF THE INVENTION

Hernia occurs when there is a weakness or hole in the muscular wall. Such hole allows organs and tissues to push through, or herniate, producing a bulge. Inguinal hernia is a protrusion of the abdominal-cavity contents through the inguinal canal or other defects within the groin region. Inguinal hernia is common in men. Inguinal hernia repair with mesh is one of the most frequently performed operations.

SUMMARY OF THE INVENTION

Inguinal hernias are defects within the muscle and fascia planes of the groin region. Complications and morbidity from inguinal hernia repair with mesh are not uncommon, and many are preventable and due to shortcomings of device and technique. Often, these defects, or holes, are simply a weakness or widening of naturally existing holes, as a non-limiting example, the inguinal canal or femoral canal. Inguinal hernias occur as a result of weakened muscle or fascia in the groin region. Abdominal contents, as non-limiting examples, intestines, fat, bladder, and other nearby organs, herniate through these defects and cause pain and/or bulging sensation. The contents also interact with nearby structures within and around the inguinal canal, as non-limiting examples, the spermatic cord in men, the round ligament in women, and with multiple nerves, including but not limiting to the ilioinguinal or genital branch of the genitofemoral nerves.

Men are considered to be more prone to inguinal hernias due to the narrower and deeper male pelvis. The vectors of force that are transmitted to the male pelvis, due to simple gravity or abdominal straining, result in pressure directed to the pelvic floor, which includes the inguinal canal and groin region. This concentration of force is considered the main reason why men have a higher prevalence of inguinal hernias than women. Also, men have a naturally wider inguinal canal diameter with a greater amount of content within the canal than women. These contents include but are not limited to the testicular vessels, nerves, the vas deferens, and muscle. It is possible that the wider orifice of entry to the inguinal canal, termed the internal ring (internal inguinal ring), can make it more prone to herniation of contents.

Women tend to have a wider and shallower pelvis than men, which helps accommodate for pregnancy. The wider shallower pelvis implies that forces from gravity or abdominal straining are distributed more evenly along the pelvic floor, resulting in less hernia formation. Also, the thin round ligament and genital nerve are the only structures that travel through the inguinal canal, thus the internal ring is much smaller than men.

Inguinal hernia repair is a common general surgical procedure performed in the United States. The gold standard for inguinal hernia repair involves use of synthetic mesh to patch the hernia defect in a tension-free manner. Inguinal hernia repair is performed using open, laparoscopic, or robotic-assisted techniques. The implantation of mesh has shown to be superior to non-mesh techniques due to the significantly lower risk of hernia recurrence when such a tension-free repair is performed.

Since the growth of synthetic mesh use, the risk of chronic pain associated with mesh implantation has taken center-stage in the United States. In some trials, over 20% of patients have mesh-related chronic pain, and 3% suffer from chronic debilitating pain that prevents them from performing their daily activities.

There is a disparity between the sexes in terms of how they respond to mesh implantation for inguinal hernia repair. Women have been found to be significantly more likely than men to suffer from mesh-related chronic pain. This is especially true with the open mesh repair techniques using heavyweight mesh, which is the standard. Among the various complications, they may suffer from chronic pelvic pain, pain with sexual intercourse, and nerve-related pain radiating to their mons and vagina, among other things. Men also have mesh-related pain and complications. These may suffer from testicular pain, sexual dysfunction, and infertility, among other things. These complications are seen with both open and laparoscopic/robotic techniques using mesh.

There is a numerous variety of mesh brands, sizes, and surgical techniques for mesh implantation. Currently, there are no differences in mesh product to accommodate for the differences in pelvic anatomy and the disparity in outcomes between male and female patients.

The present invention relates to implantable mesh for use in inguinal hernia repair operations. The devices disclosed herein are intended to address the issue of chronic pain and sexual dysfunction among males and females who undergo mesh implantation for inguinal hernia repair.

The majority of mesh-related complications are a result of a) the inflammatory response that arises from implantation of the material, b) the resultant adhesion to and/or ingrowth by the nearby structures or tissues adjacent to the mesh, or both a) and b). In males, mesh-related complications may affect the nerves around the vas deferens, the vas itself, and the vessels that Attorney Docket No. 48073-701.301 supply and drain the testicle. In females, affected structures or tissues include the nerves that lay in the groin region and supply the vagina, labia, groin, and thigh.

The devices disclosed herein are intended to protect these structures or tissues from mesh-related inflammation and tissue ingrowth by adding a protective barrier to the mesh implant, limited to the sensitive areas with which the mesh may be in contact with important structures or tissues. These areas differ between males and females, and the anatomy of the pelvis is notably different between the two sexes, and so the device varies in design for males and females. The protective barrier is intended to remain active during the healing stages after the operation, and while the inflammatory process is at its peak. The type of protective barrier may be synthetic, biologic, or a combination of both.

The meshes and methods disclosed herein may be used to reduce one or more selected from: chronic pain, functional impairment, and sexual dysfunction due to mesh implantation. At the same time, the protective barrier of the device and methods for application of the device may be used to reduce hernia recurrence and/or its severity. The area of protective barrier on the mesh may be limited to the sensitive areas, which are different between males and females. These sensitive areas may include the spermatic cord and its contents in males, and the local nerves seen among males and females. The devices disclosed herein may allow free inflammatory response, free mesh integration, or both to more tolerant areas of the groin including but not limited to muscle, fascia, periosteum, inguinal ligament, and Cooper's ligament. The devices disclosed herein may be applicable to various mesh placement techniques and surgical techniques. As non-limiting examples, these techniques include onlay mesh placement, sublay mesh placement, mesh-plug placement, retroperitoneal mesh placement, open mesh techniques, laparoscopic techniques, robotic techniques, or a combination thereof.

The devices and methods disclosed herein may include a barrier or a method of applying a barrier so that the tissue in contact with the barrier, i.e., the tube-like structure of the female or male body is protected from undesired inflammatory responses caused by the proper implantation of the mesh at least for a pre-determined period of time, i.e., the initial inflammatory phase after implantation. Further, the barrier may protect the tissue in contact with the barrier from undesired tissue adhesion to the spermatic cord and its contents or female tube-like structures that might cause tissue damages, discomfort, pain, functional impairment, or infertility. The barrier and methods of applying the barrier described herein may minimize the influences to desired tissue adhesion or ingrowth to the mesh where the barrier is not applied. The barrier may include one or more synthetic or biological materials that ensure the protection of tube-like structure of the female or the male patient especially during the initial phase of inflammation right after the mesh implantation for a pre-determined period of time.

In one aspect, disclosed herein are implantable meshes for onlay inguinal hernia repair in a male patient, comprising: a fabric layer comprising an anterior side defining a surface area, wherein the fabric layer is configured to enable tissue adhesion to said mesh; an anti-adhesive barrier comprising a shape configured to prevent direct contact between the fabric layer and critical structures of the male patient upon implantation, wherein the shape covers a part of the surface area on the anterior side of the fabric layer, the part being less than 25% of the surface area, wherein the part is inferior to a horizontally-oriented centerline and medial to a vertically-oriented centerline, wherein at least a portion of the fabric layer is barrier-free, the at least a portion being greater than 75% of the surface area, and wherein the at least a portion of the fabric layer comprises a first region superior to the horizontally-oriented centerline and a second region lateral to the vertically-oriented centerline; and a keyhole configured to properly fit the critical structures of the male patient there through without constriction, wherein the keyhole is substantially centered at 50% of a height of the fabric layer. In some cases, the shape is oblique to a horizontally-oriented centerline and a vertically-oriented centerline. In some cases, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some cases, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some cases, the shape is oblique such that a straight line starting from a most superior tip of said barrier and ending in a most medial tip of said barrier forms an angle with a horizontally-oriented centerline, the angle being in a range of 30 degrees to 60 degrees.

In some cases, the shape is oblique such that an edge of said barrier starting from a most superior tip of said barrier and going medially ends in a point at an edge of the fabric layer, the point being at least 1 cm inferior to the keyhole and medial to a vertically-oriented centerline. In some cases, a width of the fabric layer horizontally is greater than a height of the fabric layer vertically. In some cases, the part is greater than 10%. In some cases, the implantable mesh for onlay inguinal hernia repair in a male patient does not comprise a second fabric layer that is in direct contact with or in close vicinity to the fabric layer. In some cases, the shape has a gradually-increasing width laterally as said barrier extends obliquely toward a medial edge and an inferior edge the fabric layer. In some cases, the shape fans out obliquely toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the keyhole is pre-formed or tailored by a surgeon to accommodate for the critical structures of the male patient. In some cases, the fabric layer comprises a weave defining interstitial pores, the weave configured to enable tailoring of the keyhole without unravelling. In some cases, the implantable mesh for onlay inguinal hernia repair in a male patient comprises a fin configured to provide femoral space coverage for femoral hernia, the fin being barrier-free and extending inferiorly from an inguinal ligament level of the male patient upon implantation. In some cases, the implantable mesh for onlay inguinal hernia repair in a male patient is configured to be implanted anterior to a hernia defect and posterior to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for onlay inguinal hernia repair in a male patient, comprising: a fabric layer comprising an anterior side defining a surface area, wherein the fabric layer is configured to enable tissue adhesion to said mesh; an anti-adhesive barrier comprising a shape configured to prevent direct contact between the fabric layer and critical structures of the male patient upon implantation, wherein the shape covers a part of the surface area on the anterior side of the fabric layer, the part being less than 25%, and wherein the shape is oblique to a horizontally-oriented centerline and a vertically-oriented centerline; and a keyhole configured to properly fit the critical structures of the male patient therethrough without constriction, wherein the keyhole is inferior to a horizontally-oriented centerline and medial to a vertically-oriented centerline. In some cases, the part is inferior to a horizontally-oriented centerline and medial to a vertically-oriented centerline. In some cases, at least a portion of the fabric layer is barrier-free, the at least a portion being greater than 75% of the surface area, the at least a portion of the fabric layer comprise a first region superior to the horizontally-oriented centerline and a second region lateral to the vertically-oriented centerline. In some cases, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some cases, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some cases, the shape is oblique such that a straight line starting from a most superior tip of said barrier and ending in a most medial tip of said barrier forms an angle with a horizontally-oriented centerline, the angle being in a range of 30 degrees to 60 degrees. In some cases, the shape is oblique such that an edge of said barrier starting from a most superior tip of said barrier and going medially ends in a point at an edge of the fabric layer, the point being at least 1 cm inferior to the keyhole and medial to a vertically-oriented centerline. In some cases, a width of the fabric layer horizontally is greater than a height of the fabric layer vertically. In some cases, the part is greater than 10%. In some cases, the implantable mesh for onlay inguinal hernia repair in a male patient does not comprise a second fabric layer that is in direct contact with or in close vicinity to the fabric layer. In some cases, the shape has a gradually-increasing lateral width as said barrier goes obliquely toward a medial edge and an inferior edge the fabric layer. In some cases, the shape fans out obliquely toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the keyhole is pre-formed or tailored by a surgeon to accommodate for the critical structures of the male patient. In some cases, the fabric layer comprises a weave defining interstitial pores, the weave configured to enable tailoring of the keyhole without unravelling. In some cases, the implantable mesh for onlay inguinal hernia repair in a male patient comprises a fin configured to provide femoral space coverage for femoral hernia, the fin being barrier-free and extending inferiorly from an inguinal ligament level of the male patient upon implantation. In some cases, the implantable mesh for onlay inguinal hernia repair in a male patient is configured to be implanted anterior to a hernia defect and posterior to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for sublay inguinal hernia repair in a male patient, comprising: a fabric layer comprising an anterior side defining a surface area wherein the fabric layer is configured to enable tissue adhesion to said mesh; and an anti-adhesive barrier comprising a shape configured to prevent direct contact between the fabric layer and critical structures of the male patient upon implantation, wherein the shape covers a part of the surface area on the anterior side of the fabric layer, the part being less than 25%, wherein the part is inferior to a horizontally-oriented centerline and medial to a vertically-oriented centerline, wherein at least a portion of the fabric layer is barrier-free, the at least a portion being greater than 75% of the surface area, and wherein the at least a portion of the fabric layer comprises a first region superior to the horizontally-oriented centerline and a second region lateral to the vertically-oriented centerline, and wherein the anti-adhesive barrier is limited to be within a predetermined distance to an inferior edge of the fabric layer. In some cases, the predetermined distance is about 1 cm. In some cases, the implantable mesh for sublay inguinal hernia repair in a male patient does not comprise a keyhole, the keyhole comprising a size to accommodate critical structures of the male patient therethrough without constriction. In some cases, a second portion of the fabric layer is barrier-free, the second portion being at least 25% of a mesh width from a most medial tip of the fabric layer and inferior to a horizontally-oriented centerline. In some cases, a maximal barrier width laterally is no greater than 50% of a mesh width. In some cases, the shape is not oblique such that a straight line connecting a most superior point of the barrier and a midpoint of a most inferior edge of said barrier is substantially parallel to a vertically-oriented centerline. In some cases, the shape is not oblique such that a straight line connecting a most superior point of the barrier and a midpoint of a most inferior edge of said barrier is substantially orthogonal to a horizontally-oriented centerline. In some cases, a width of the fabric layer horizontally is greater than a height of the fabric layer vertically. In some cases, the part is greater than 10%. In some cases, the implantable mesh for sublay inguinal hernia repair in a male patient does not comprise a second fabric layer that is in direct contact with or in close vicinity to the fabric layer. In some cases, the shape has a gradually-increasing width laterally as said barrier extends toward a medial edge and an inferior edge the fabric layer. In some cases, the shape fans out toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the implantable mesh for sublay inguinal hernia repair in a male patient comprises a fin configured to provide femoral space coverage for femoral hernia, the fin being barrier-free and extending inferiorly from an inguinal ligament level of the male patient upon implantation. In some cases, the fabric layer comprises a weave defining interstitial pores, the weave configured to enable tailoring of the keyhole without unravelling. In some cases, the implantable mesh for sublay inguinal hernia repair in a male patient is configured to be implanted posterior to a hernia defect and posterior or deep to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for onlay inguinal hernia repair in a female patient, comprising: a fabric layer comprising a side defining a surface area wherein the fabric layer is configured to enable tissue adhesion to said mesh; and an anti-adhesive barrier comprising a shape configured to prevent direct contact between the fabric layer and a genital nerve of the female patient upon implantation, wherein the shape covers a part of the surface area on the side of the fabric layer, the part being less than 15% of the surface area, wherein the part is inferior to a horizontally-oriented centerline and medial to a vertically-oriented centerline, wherein at least a portion of the fabric layer is barrier-free, the at least a portion being greater than 85% of the surface area, and wherein the at least a portion of the fabric layer comprises a first region superior to the horizontally-oriented centerline and a second region lateral to the vertically-oriented centerline. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the fabric layer comprises a weave defining interstitial pores, the weave configured to enable tailoring of the keyhole without unravelling. In some cases, the implantable mesh for onlay inguinal hernia repair in a female patient comprises a precut or tailored keyhole, the keyhole comprising a size to accommodate a round ligament of the female patient therethrough without constriction. In some cases, the anti-adhesive barrier covers at most 15% of the surface area of the fabric layer on the posterior side. In some cases, the fabric layer has a density of no greater than 40 grams per square meter. In some cases, the implantable mesh for onlay inguinal hernia repair in a female patient does not comprise a second fabric layer that is in direct contact with or in close vicinity to the fabric layer. In some cases, the anti-adhesive barrier does not prevent contact between the fabric layer and a round ligament of the female patient. In some cases, a width of the fabric layer laterally is greater than a height of the fabric layer. In some cases, the fabric layer is configured to provide femoral coverage upon implantation into the female patient. In some cases, the side is anterior side, or a posterior side. In some cases, the part is inferior to a horizontally-oriented centerline and medial to a vertically-oriented centerline. In some cases, the shape has a maximal height of about 2 cm. In some cases, the fabric layer includes a fin extending inferiorly from an inguinal ligament level. In some cases, the fin is precut or tailored by a surgeon. In some cases, the fin does not obstruct a femoral artery and a femoral vein upon implantation into the female patient. In certain cases, the fin comprises a curved inferior tip configurable to enable attachment to Cooper's ligament. In some cases, the fin is substantially inferior to a horizontally-oriented centerline and medial to a vertically-oriented centerline. In some cases, the fin is configured to provide femoral space coverage for femoral hernia, the fin being barrier-free and extending inferiorly from an inguinal ligament level of the male patient upon implantation. In some cases, the implantable mesh for onlay inguinal hernia repair in a female patient is configured to be implanted anterior to a hernia defect and posterior to the genital nerve. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are implantable meshes for sublay inguinal hernia repair in a female patient, comprising: a fabric layer comprising a side defining a surface area; and a fin comprising a rounded inferior tip; the fin extending inferiorly from an inguinal ligament level of the fabric layer, wherein the fabric layer is configured to enable tissue adhesion to said mesh upon implantation in the female patient. In some embodiments, the fabric layer comprising a weave defining interstitial pores, each of the interstitial pores having a maximal dimension on the surface area that is no smaller than 4 mm, the maximal dimension being a width, a length, a diameter, or a diagonal. In some embodiments, the fabric layer comprises a weave defining interstitial pores, the weave configured to enable tailoring of the keyhole without unravelling. In some embodiments, the implantable mesh for sublay inguinal hernia repair in a female patient does not comprise a keyhole, the keyhole comprising a size to properly fit a round ligament of the female patient therethrough without constriction. In some embodiments, the implantable mesh for sublay inguinal hernia repair in a female patient does not comprise an anti-adhesive barrier. In some cases, the fabric layer has a density of no greater than 40 grams per square meter. In some cases, the mesh does not comprise a second fabric layer that is in direct contact with or in close vicinity to the fabric layer. In some cases, wherein a width of the fabric layer laterally is greater than a height of the fabric layer vertically. In some cases, the fabric layer is configured to provide femoral coverage upon implantation into the female patient. In some cases, the fabric layer includes a fin extending inferiorly from an inguinal ligament level. In some cases, the fin does not obstruct a femoral artery and femoral vein upon implantation into the female patient. In some cases, the fin comprises a curved inferior tip configurable to enable attachment to Cooper's ligament. In some cases, the fin is medial to a vertically-oriented centerline and medial to a vertically-oriented centerline. In some cases, the implantable mesh for sublay inguinal hernia repair in a female patient is configured to be implanted posterior to a hernia defect and posterior or deep to the genital nerve. In some cases, the fin is barrier-free and extending inferiorly from an inguinal ligament level. In some cases, the fin is precut or tailored by a surgeon. In some cases, the side is an anterior side or a posterior side. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are methods of making an implantable mesh for inguinal hernia repair in a male patient, the method comprising: providing a fabric layer, the fabric layer comprising a side comprising a surface area, wherein the fabric layer allows tissue adhesion to the implantable mesh; providing an anti-adhesive barrier on at least a part of the surface area of the fabric layer, wherein the anti-adhesive barrier comprises a shape to prevent direct contact between the fabric layer and critical structures upon implantation in the male patient, and wherein the anti-adhesive barrier covers no greater than about 25% of a surface area on the at least one side of the fabric layer; and cutting a keyhole that is completely surrounded by said barrier, wherein the keyhole is inferior to a horizontally-oriented centerline and medial to a vertically-oriented centerline, and wherein the keyhole is configured to accommodate for the critical structures of the male patient. In some embodiments, the part is inferior to a horizontally-oriented centerline and medial to a vertically-oriented centerline. In some embodiments, at least a portion of the fabric layer is barrier free, the portion being superior to the horizontally-oriented centerline and medial to the vertically-oriented centerline. In some embodiments, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some embodiments, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some embodiments, the shape is oblique such that a straight line starting from a most superior tip of said barrier and ending in a most medial tip of said barrier forms an angle with a horizontally-oriented centerline, the angle being in a range of 30 degrees to 60 degrees. In some embodiments, the shape is oblique such that an edge of said barrier starting from a most superior tip of said barrier and going medially ends in an edge of the fabric layer that is at least 1 cm inferior to the keyhole and medial to a vertically-oriented centerline. In some embodiments, the fabric layer comprises a weave defining interstitial pores, each of the interstitial pores having a maximal dimension on the surface area that is no smaller than 4 mm, the maximal dimension being a width, a length, a diameter, or a diagonal. In some embodiments, the part is greater than 10%. In some embodiments, the fabric layer has a density of no greater than 40 grams per square meter. In some embodiments, the implantable mesh does not comprise a second fabric layer that is in direct contact with or in close vicinity to the fabric layer. In some embodiments, the shape has a gradually-increasing lateral width as said barrier goes obliquely toward a medial edge and an inferior edge the fabric layer. In some embodiments, the shape fans out obliquely toward a medial edge and an inferior edge the fabric layer. In some embodiments, the critical structures comprise a spermatic cord and its contents, and a genital nerve. In some embodiments, the spermatic cord and its contents comprise vas deferens, testicular vessels, vasal nerves, cremasteric muscle, or a combination thereof. In some embodiments, the fabric layer comprises a weave defining interstitial pores, the weave configured to enable tailoring of the keyhole without unravelling. In some embodiments, the implantable mesh comprises a fin configured to provide femoral space coverage for femoral hernia, the fin being barrier-free and extending inferiorly from an inguinal ligament level. In some embodiments, the method of making an implantable mesh for inguinal hernia repair in a male patient comprises implanting the implantable mesh anterior or posterior to a hernia defect and posterior or deep to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are methods of making an implantable mesh for inguinal hernia repair in a female patient, comprising: providing a fabric layer, the fabric layer comprising a side comprising a surface area, wherein the fabric layer is configured to allow tissue adhesion to the implantable mesh upon implantation into the female patient; optionally providing an anti-adhesive barrier on at least a part of the surface area of the fabric layer, wherein the anti-adhesive barrier comprises a shape to prevent direct contact between the fabric layer and a genital nerve upon implantation into the female patient, and wherein the anti-adhesive barrier covers no greater than about 20% of a surface area on the at least one side of the fabric layer; and shaping a fin extending inferiorly from an inguinal ligament level of the fabric layer, the fin comprising a rounded inferior tip. In certain cases, the implantable mesh does not comprise a keyhole, the keyhole comprising a size to properly fit critical structures of the male patient therethrough without constriction. In some embodiments, the anti-adhesive barrier covers at most 10% of the surface area of the fabric layer on the posterior side. In some embodiments, the fabric layer has a density of no greater than 40 grams per square meter. In some embodiments, wherein the implantable mesh does not comprise a second fabric layer that is in direct contact with or in close vicinity to the fabric layer. In some cases, the anti-adhesive barrier does not prevent contact between the fabric layer and a round ligament of the female patient. In some cases, a width of the fabric layer laterally is greater than a height of the fabric layer. In some cases, the fabric layer is configured to provide femoral coverage after said mesh is properly inserted. In some cases, the fabric layer includes a fin extending inferiorly from an inguinal ligament level. In some cases, the fin does not obstruct a femoral artery and femoral vein after the mesh is properly implanted. In some cases, the fin comprises a curved inferior tip configurable to enable attachment to Cooper's ligament. In some cases, the fin is medial to a vertically-oriented centerline and inferior to a vertically-oriented centerline. In some cases, the part is inferior to a horizontally-oriented centerline and medial to a vertically-oriented centerline. In some cases, at least a portion of the fabric layer is barrier free, the portion being superior to the horizontally-oriented centerline and medial to the vertically-oriented centerline. In some cases, the shape has a maximal height of about 2 cm. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the method of making an implantable mesh for inguinal hernia repair in a female patient comprises implanting the implantable mesh anterior or posterior to both a hernia defect and the genital nerve. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the fin is configured to provide femoral space coverage for femoral hernia, the fin being barrier-free and extending inferiorly from an inguinal ligament level. In some cases, the fabric layer comprises a weave defining interstitial pores, the weave configured to enable tailoring of the keyhole without unravelling. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for inlay inguinal hernia repair in a patient, comprising: an onlay mesh comprising a first fabric layer comprising a first anterior side defining a first surface area, wherein the first fabric layer is configured to enable tissue adhesion to said mesh; a sublay mesh comprising a second fabric layer comprising a second anterior side defining a second surface area, wherein the first fabric layer is configured to enable tissue adhesion to said mesh; a tubular mesh connecting the onlay mesh and the sublay mesh, the tubular mesh comprising a fabric structure defining a third surface area, wherein the fabric structure is configured to enable tissue adhesion to said mesh an anti-adhesive barrier comprising a shape configured to prevent direct contact of critical structures by both of the first and the second fabric layers and the critical structures upon implantation in the patient, wherein the shape covers: a first part of the first surface area of the first fabric layer, the first part being less than 25% of the first surface area; a second part of the second surface area of the second fabric layer, the second part being less than 25% of the second surface area; and a third part of the third surface area of the fabric structure, the third part being less than 25% of the third surface area, wherein the first part is inferior to a horizontally-oriented centerline and medial to a vertically-oriented centerline of the first fabric layer, and wherein the second part is inferior to a horizontally-oriented centerline of the second fabric layer, wherein the third part extends substantially from the onlay mesh to the sublay mesh and connects the first part and the second part; and a keyhole in the first fabric layer configured to properly fit the critical structures of the patient therethrough without constriction, wherein the keyhole is substantially centered at about 30% to 50% of a vertical height of the first fabric layer. In certain embodiments, at least a portion of the first fabric layer is barrier-free, the portion being greater than 75% of the first surface area, and wherein the at least a portion of the fabric layer comprise a first region superior to the horizontally-oriented centerline and a second region lateral to the vertically-oriented centerline. In certain embodiments, at least a portion of the second fabric layer is barrier-free, the portion being greater than 75% of the second surface area, and wherein the at least a portion of the fabric layer comprise a first region superior to the horizontally-oriented centerline, a second region lateral to the vertical centerline, and a third region medial to the vertical centerline. In certain embodiments, the critical structures comprise a spermatic cord and its content and a genital nerve of a male patient, or a genital nerve of a female patient. In certain embodiments, the keyhole is lateral to a vertical centerline of the first fabric layer. In certain embodiments, the third surface area is a tubular surface area of the tubular mesh. In certain embodiments, the third part is in an inferolateral quarter of the tubular surface. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are implantable meshes for inlay inguinal hernia repair in a patient, comprising: a fabric layer comprising an outer side defining a surface area, the fabric layer being foldable; an anti-adhesive barrier comprising a shape configured to prevent direct contact between the fabric layer and critical structures of the patient upon implantation, wherein the shape covers at least a portion of the outer side, the portion being no greater than 50% of the surface area, wherein the shape is limited to be within a predetermined distance to an anterior edge of the outer side, wherein the shape extends substantially from a posterior edge of the outer side. In some embodiments, the predetermined distance is about 1 cm. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9A shows another non-limiting example of a mesh for inguinal hernia repair in male patients described herein with anti-adhesive barrier viewing from the anterior/ventral side, in accordance with embodiments.

DETAILED DESCRIPTION OF THE INVENTION

Figure 1:
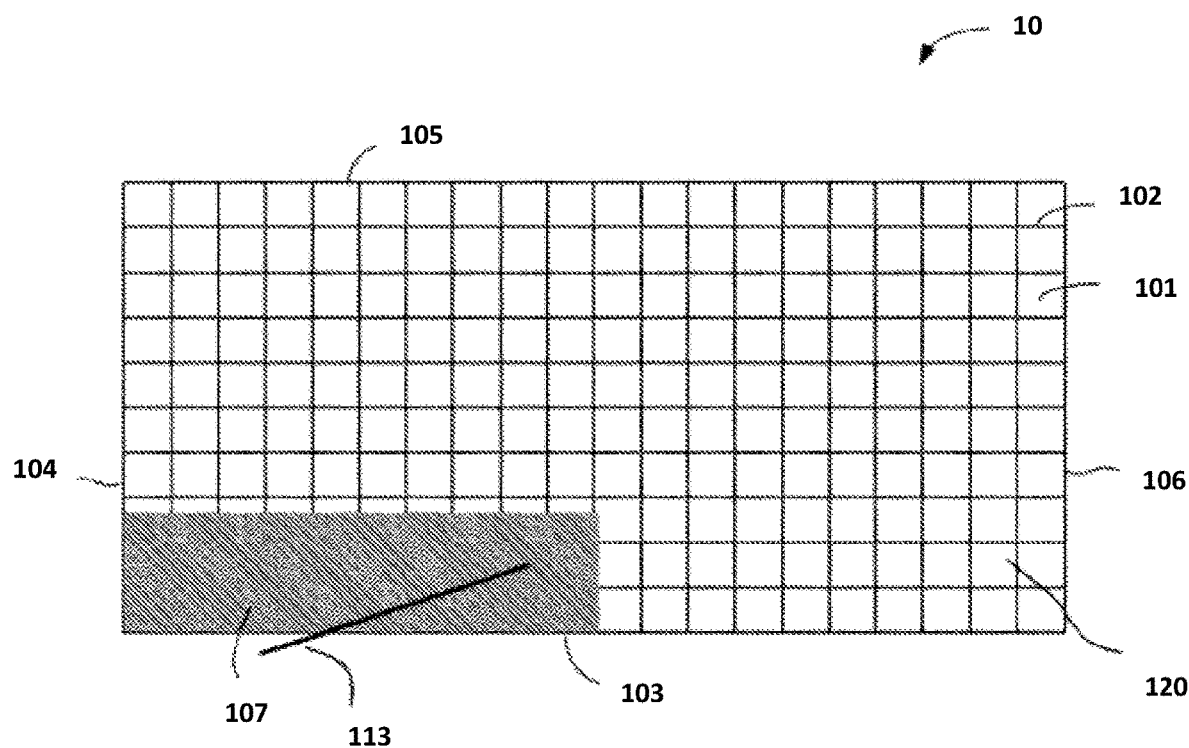
FIG. 1 shows a non-limiting example of a mesh for inguinal hernia repair in female patients described herein with anti-adhesive barrier, in accordance with embodiments.

In one aspect, disclosed herein are implantable meshes for onlay inguinal hernia repair in a male patient, comprising: a fabric layer comprising an anterior side defining a surface area, wherein the fabric layer is configured to enable tissue adhesion to said mesh; an anti-adhesive barrier comprising a shape configured to prevent direct contact between the fabric layer and critical structures of the male patient upon implantation, wherein the shape covers a part of the surface area on the anterior side of the fabric layer, the part being less than 25% of the surface area, wherein the part is inferior to a horizontally-oriented centerline and medial to a vertically-oriented centerline, wherein at least a portion of the fabric layer is barrier-free, the at least a portion being greater than 75% of the surface area, and wherein the at least a portion of the fabric layer comprises a first region superior to the horizontally-oriented centerline and a second region lateral to the vertically-oriented centerline; and a keyhole configured to properly fit the critical structures of the male patient therethrough without constriction, wherein the keyhole is substantially centered at 50% of a height of the fabric layer. In some cases, the shape is oblique to a horizontally-oriented centerline and a vertically-oriented centerline. In some cases, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some cases, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some cases, the shape is oblique such that a straight line starting from a most superior tip of said barrier and ending in a most medial tip of said barrier forms an angle with a horizontally-oriented centerline, the angle being in a range of 30 degrees to 60 degrees. In some cases, the shape is oblique such that an edge of said barrier starting from a most superior tip of said barrier and going medially ends in a point at an edge of the fabric layer, the point being at least 1 cm inferior to the keyhole and medial to a vertically-oriented centerline. In some cases, a width of the fabric layer horizontally is greater than a height of the fabric layer vertically. In some cases, the part is greater than 10%. In some cases, the implantable mesh for onlay inguinal hernia repair in a male patient does not comprise a second fabric layer that is in direct contact with or in close vicinity to the fabric layer. In some cases, the shape has a gradually-increasing width laterally as said barrier extends obliquely toward a medial edge and an inferior edge the fabric layer. In some cases, the shape fans out obliquely toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the keyhole is pre-formed or tailored by a surgeon to accommodate for the critical structures of the male patient. In some cases, the fabric layer comprises a weave defining interstitial pores, the weave configured to enable tailoring of the keyhole without unravelling. In some cases, the implantable mesh for onlay inguinal hernia repair in a male patient comprises a fin configured to provide femoral space coverage for femoral hernia, the fin being barrier-free and extending inferiorly from an inguinal ligament level of the male patient upon implantation. In some cases, the implantable mesh for onlay inguinal hernia repair in a male patient is configured to be implanted anterior to a hernia defect and posterior to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for onlay inguinal hernia repair in a male patient, comprising: a fabric layer comprising an anterior side defining a surface area, wherein the fabric layer is configured to enable tissue adhesion to said mesh; an anti-adhesive barrier comprising a shape configured to prevent direct contact between the fabric layer and critical structures of the male patient upon implantation, wherein the shape covers a part of the surface area on the anterior side of the fabric layer, the part being less than 25%, and wherein the shape is oblique to a horizontally-oriented centerline and a vertically-oriented centerline; and a keyhole configured to properly fit the critical structures of the male patient therethrough without constriction, wherein the keyhole is inferior to a horizontally-oriented centerline and medial to a vertically-oriented centerline. In some cases, the part is inferior to a horizontally-oriented centerline and medial to a vertically-oriented centerline. In some cases, at least a portion of the fabric layer is barrier-free, the at least a portion being greater than 75% of the surface area, the at least a portion of the fabric layer comprise a first region superior to the horizontally-oriented centerline and a second region lateral to the vertically-oriented centerline. In some cases, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some cases, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some cases, the shape is oblique such that a straight line starting from a most superior tip of said barrier and ending in a most medial tip of said barrier forms an angle with a horizontally-oriented centerline, the angle being in a range of 30 degrees to 60 degrees. In some cases, the shape is oblique such that an edge of said barrier starting from a most superior tip of said barrier and going medially ends in a point at an edge of the fabric layer, the point being at least 1 cm inferior to the keyhole and medial to a vertically-oriented centerline. In some cases, a width of the fabric layer horizontally is greater than a height of the fabric layer vertically. In some cases, the part is greater than 10%. In some cases, the implantable mesh for onlay inguinal hernia repair in a male patient does not comprise a second fabric layer that is in direct contact with or in close vicinity to the fabric layer. In some cases, the shape has a gradually-increasing lateral width as said barrier goes obliquely toward a medial edge and an inferior edge the fabric layer. In some cases, the shape fans out obliquely toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the keyhole is pre-formed or tailored by a surgeon to accommodate for the critical structures of the male patient. In some cases, the fabric layer comprises a weave defining interstitial pores, the weave configured to enable tailoring of the keyhole without unravelling. In some cases, the implantable mesh for onlay inguinal hernia repair in a male patient comprises a fin configured to provide femoral space coverage for femoral hernia, the fin being barrier-free and extending inferiorly from an inguinal ligament level of the male patient upon implantation. In some cases, the implantable mesh for onlay inguinal hernia repair in a male patient is configured to be implanted anterior to a hernia defect and posterior to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for sublay inguinal hernia repair in a male patient, comprising: a fabric layer comprising an anterior side defining a surface area wherein the fabric layer is configured to enable tissue adhesion to said mesh; and an anti-adhesive barrier comprising a shape configured to prevent direct contact between the fabric layer and critical structures of the male patient upon implantation, wherein the shape covers a part of the surface area on the anterior side of the fabric layer, the part being less than 25%, wherein the part is inferior to a horizontally-oriented centerline and medial to a vertically-oriented centerline, wherein at least a portion of the fabric layer is barrier-free, the at least a portion being greater than 75% of the surface area, and wherein the at least a portion of the fabric layer comprises a first region superior to the horizontally-oriented centerline and a second region lateral to the vertically-oriented centerline, and wherein the anti-adhesive barrier is limited to be within a predetermined distance to an inferior edge of the fabric layer. In some cases, the predetermined distance is about 1 cm. In some cases, the implantable mesh for sublay inguinal hernia repair in a male patient does not comprise a keyhole, the keyhole comprising a size to accommodate critical structures of the male patient therethrough without constriction. In some cases, a second portion of the fabric layer is barrier-free, the second portion being at least 25% of a mesh width from a most medial tip of the fabric layer and inferior to a horizontally-oriented centerline. In some cases, a maximal barrier width laterally is no greater than 50% of a mesh width. In some cases, the shape is not oblique such that a straight line connecting a most superior point of the barrier and a midpoint of a most inferior edge of said barrier is substantially parallel to a vertically-oriented centerline. In some cases, the shape is not oblique such that a straight line connecting a most superior point of the barrier and a midpoint of a most inferior edge of said barrier is substantially orthogonal to a horizontally-oriented centerline. In some cases, a width of the fabric layer horizontally is greater than a height of the fabric layer vertically. In some cases, the part is greater than 10%. In some cases, the implantable mesh for sublay inguinal hernia repair in a male patient does not comprise a second fabric layer that is in direct contact with or in close vicinity to the fabric layer. In some cases, the shape has a gradually-increasing width laterally as said barrier extends toward a medial edge and an inferior edge the fabric layer. In some cases, the shape fans out toward a medial edge and an inferior edge the fabric layer. In some cases, the critical structures comprise a spermatic cord and its contents, and a genital nerve. In some cases, the spermatic cord and its contents comprise vas deferens, testicular vessels, vasal nerves, cremasteric muscle, or a combination thereof. In some cases, the implantable mesh for sublay inguinal hernia repair in a male patient comprises a fin configured to provide femoral space coverage for femoral hernia, the fin being barrier-free and extending inferiorly from an inguinal ligament level of the male patient upon implantation. In some cases, the fabric layer comprises a weave defining interstitial pores, the weave configured to enable tailoring of the keyhole without unravelling. In some cases, the implantable mesh for sublay inguinal hernia repair in a male patient is configured to be implanted posterior to a hernia defect and posterior or deep to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for onlay inguinal hernia repair in a female patient, comprising: a fabric layer comprising a side defining a surface area wherein the fabric layer is configured to enable tissue adhesion to said mesh; and an anti-adhesive barrier comprising a shape configured to prevent direct contact between the fabric layer and a genital nerve of the female patient upon implantation, wherein the shape covers a part of the surface area on the side of the fabric layer, the part being less than 15% of the surface area, wherein the part is inferior to a horizontally-oriented centerline and medial to a vertically-oriented centerline, wherein at least a portion of the fabric layer is barrier-free, the at least a portion being greater than 85% of the surface area, and wherein the at least a portion of the fabric layer comprises a first region superior to the horizontally-oriented centerline and a second region lateral to the vertically-oriented centerline. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the fabric layer comprises a weave defining interstitial pores, the weave configured to enable tailoring of the keyhole without unravelling. In some cases, the implantable mesh for onlay inguinal hernia repair in a female patient comprises a precut or tailored keyhole, the keyhole comprising a size to accommodate a round ligament of the female patient therethrough without constriction. In some cases, the anti-adhesive barrier covers at most 15% of the surface area of the fabric layer on the posterior side. In some cases, the fabric layer has a density of no greater than 40 grams per square meter. In some cases, the implantable mesh for onlay inguinal hernia repair in a female patient does not comprise a second fabric layer that is in direct contact with or in close vicinity to the fabric layer. In some cases, the anti-adhesive barrier does not prevent contact between the fabric layer and a round ligament of the female patient. In some cases, a width of the fabric layer laterally is greater than a height of the fabric layer. In some cases, the fabric layer is configured to provide femoral coverage upon implantation into the female patient. In some cases, the side is anterior side, or a posterior side. In some cases, the part is inferior to a horizontally-oriented centerline and medial to a vertically-oriented centerline. In some cases, the shape has a maximal height of about 2 cm. In some cases, the fabric layer includes a fin extending inferiorly from an inguinal ligament level. In some cases, the fin is precut or tailored by a surgeon. In some cases, the fin does not obstruct a femoral artery and a femoral vein upon implantation into the female patient. In certain cases, the fin comprises a curved inferior tip configurable to enable attachment to Cooper's ligament. In some cases, the fin is substantially inferior to a horizontally-oriented centerline and medial to a vertically-oriented centerline. In some cases, the fin is configured to provide femoral space coverage for femoral hernia, the fin being barrier-free and extending inferiorly from an inguinal ligament level of the male patient upon implantation. In some cases, the implantable mesh for onlay inguinal hernia repair in a female patient is configured to be implanted anterior to a hernia defect and posterior to the genital nerve. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are implantable meshes for sublay inguinal hernia repair in a female patient, comprising: a fabric layer comprising a side defining a surface area; and a fin comprising a rounded inferior tip; the fin extending inferiorly from an inguinal ligament level of the fabric layer, wherein the fabric layer is configured to enable tissue adhesion to said mesh upon implantation in the female patient. In some embodiments, the fabric layer comprising a weave defining interstitial pores, each of the interstitial pores having a maximal dimension on the surface area that is no smaller than 4 mm, the maximal dimension being a width, a length, a diameter, or a diagonal. In some embodiments, the fabric layer comprises a weave defining interstitial pores, the weave configured to enable tailoring of the keyhole without unravelling. In some embodiments, the implantable mesh for sublay inguinal hernia repair in a female patient does not comprise a keyhole, the keyhole comprising a size to properly fit a round ligament of the female patient therethrough without constriction. In some embodiments, the implantable mesh for sublay inguinal hernia repair in a female patient does not comprise an anti-adhesive barrier. In some cases, the fabric layer has a density of no greater than 40 grams per square meter. In some cases, the mesh does not comprise a second fabric layer that is in direct contact with or in close vicinity to the fabric layer. In some cases, wherein a width of the fabric layer laterally is greater than a height of the fabric layer vertically. In some cases, the fabric layer is configured to provide femoral coverage upon implantation into the female patient. In some cases, the fabric layer includes a fin extending inferiorly from an inguinal ligament level. In some cases, the fin does not obstruct a femoral artery and femoral vein upon implantation into the female patient. In some cases, the fin comprises a curved inferior tip configurable to enable attachment to Cooper's ligament. In some cases, the fin is medial to a vertically-oriented centerline and medial to a vertically-oriented centerline. In some cases, the implantable mesh for sublay inguinal hernia repair in a female patient is configured to be implanted posterior to a hernia defect and posterior or deep to the genital nerve. In some cases, the fin is barrier-free and extending inferiorly from an inguinal ligament level. In some cases, the fin is precut or tailored by a surgeon. In some cases, the side is an anterior side or a posterior side. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are methods of making an implantable mesh for inguinal hernia repair in a male patient, the method comprising: providing a fabric layer, the fabric layer comprising a side comprising a surface area, wherein the fabric layer allows tissue adhesion to the implantable mesh; providing an anti-adhesive barrier on at least a part of the surface area of the fabric layer, wherein the anti-adhesive barrier comprises a shape to prevent direct contact between the fabric layer and critical structures upon implantation in the male patient, and wherein the anti-adhesive barrier covers no greater than about 25% of a surface area on the at least one side of the fabric layer; and cutting a keyhole that is completely surrounded by said barrier, wherein the keyhole is inferior to a horizontally-oriented centerline and medial to a vertically-oriented centerline, and wherein the keyhole is configured to accommodate for the critical structures of the male patient. In some embodiments, the part is inferior to a horizontally-oriented centerline and medial to a vertically-oriented centerline. In some embodiments, at least a portion of the fabric layer is barrier free, the portion being superior to the horizontally-oriented centerline and medial to the vertically-oriented centerline. In some embodiments, the shape is oblique such that a straight line connecting a center of the keyhole and a midpoint of an overlapping edge of said barrier and the fabric layer forms an angle with a vertically-oriented centerline, the angle being in a range of 30 degrees to 60 degrees. In some embodiments, the shape is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some embodiments, the shape is oblique such that a straight line starting from a most superior tip of said barrier and ending in a most medial tip of said barrier forms an angle with a horizontally-oriented centerline, the angle being in a range of 30 degrees to 60 degrees. In some embodiments, the shape is oblique such that an edge of said barrier starting from a most superior tip of said barrier and going medially ends in an edge of the fabric layer that is at least 1 cm inferior to the keyhole and medial to a vertically-oriented centerline. In some embodiments, the fabric layer comprises a weave defining interstitial pores, each of the interstitial pores having a maximal dimension on the surface area that is no smaller than 4 mm, the maximal dimension being a width, a length, a diameter, or a diagonal. In some embodiments, the part is greater than 10%. In some embodiments, the fabric layer has a density of no greater than 40 grams per square meter. In some embodiments, the implantable mesh does not comprise a second fabric layer that is in direct contact with or in close vicinity to the fabric layer. In some embodiments, the shape has a gradually-increasing lateral width as said barrier goes obliquely toward a medial edge and an inferior edge the fabric layer. In some embodiments, the shape fans out obliquely toward a medial edge and an inferior edge the fabric layer. In some embodiments, the critical structures comprise a spermatic cord and its contents, and a genital nerve. In some embodiments, the spermatic cord and its contents comprise vas deferens, testicular vessels, vasal nerves, cremasteric muscle, or a combination thereof. In some embodiments, the fabric layer comprises a weave defining interstitial pores, the weave configured to enable tailoring of the keyhole without unravelling. In some embodiments, the implantable mesh comprises a fin configured to provide femoral space coverage for femoral hernia, the fin being barrier-free and extending inferiorly from an inguinal ligament level. In some embodiments, the method of making an implantable mesh for inguinal hernia repair in a male patient comprises implanting the implantable mesh anterior or posterior to a hernia defect and posterior or deep to the critical structures. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are methods of making an implantable mesh for inguinal hernia repair in a female patient, comprising: providing a fabric layer, the fabric layer comprising a side comprising a surface area, wherein the fabric layer is configured to allow tissue adhesion to the implantable mesh upon implantation into the female patient; optionally providing an anti-adhesive barrier on at least a part of the surface area of the fabric layer, wherein the anti-adhesive barrier comprises a shape to prevent direct contact between the fabric layer and a genital nerve upon implantation into the female patient, and wherein the anti-adhesive barrier covers no greater than about 20% of a surface area on the at least one side of the fabric layer; and shaping a fin extending inferiorly from an inguinal ligament level of the fabric layer, the fin comprising a rounded inferior tip. In certain cases, the implantable mesh does not comprise a keyhole, the keyhole comprising a size to properly fit critical structures of the male patient therethrough without constriction. In some embodiments, the anti-adhesive barrier covers at most 10% of the surface area of the fabric layer on the posterior side. In some embodiments, the fabric layer has a density of no greater than 40 grams per square meter. In some embodiments, wherein the implantable mesh does not comprise a second fabric layer that is in direct contact with or in close vicinity to the fabric layer. In some cases, the anti-adhesive barrier does not prevent contact between the fabric layer and a round ligament of the female patient. In some cases, a width of the fabric layer laterally is greater than a height of the fabric layer. In some cases, the fabric layer is configured to provide femoral coverage after said mesh is properly inserted. In some cases, the fabric layer includes a fin extending inferiorly from an inguinal ligament level. In some cases, the fin does not obstruct a femoral artery and femoral vein after the mesh is properly implanted. In some cases, the fin comprises a curved inferior tip configurable to enable attachment to Cooper's ligament. In some cases, the fin is medial to a vertically-oriented centerline and inferior to a vertically-oriented centerline. In some cases, the part is inferior to a horizontally-oriented centerline and medial to a vertically-oriented centerline. In some cases, at least a portion of the fabric layer is barrier free, the portion being superior to the horizontally-oriented centerline and medial to the vertically-oriented centerline. In some cases, the shape has a maximal height of about 2 cm. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the method of making an implantable mesh for inguinal hernia repair in a female patient comprises implanting the implantable mesh anterior or posterior to both a hernia defect and the genital nerve. In some cases, the fabric layer comprises a weave defining interstitial pores, each of the interstitial pores having a maximal dimension on the surface area that is no smaller than 4 mm, the maximal dimension being a width, a length, a diameter, or a diagonal. In some cases, the fin is configured to provide femoral space coverage for femoral hernia, the fin being barrier-free and extending inferiorly from an inguinal ligament level. In some cases, the fabric layer comprises a weave defining interstitial pores, the weave configured to enable tailoring of the keyhole without unravelling. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In another aspect, disclosed herein are implantable meshes for inlay inguinal hernia repair in a patient, comprising: an onlay mesh comprising a first fabric layer comprising a first anterior side defining a first surface area, wherein the first fabric layer is configured to enable tissue adhesion to said mesh; a sublay mesh comprising a second fabric layer comprising a second anterior side defining a second surface area, wherein the first fabric layer is configured to enable tissue adhesion to said mesh; a tubular mesh connecting the onlay mesh and the sublay mesh, the tubular mesh comprising a fabric structure defining a third surface area, wherein the fabric structure is configured to enable tissue adhesion to said mesh an anti-adhesive barrier comprising a shape configured to prevent direct contact of critical structures by both of the first and the second fabric layers and the critical structures upon implantation in the patient, wherein the shape covers: a first part of the first surface area of the first fabric layer, the first part being less than 25% of the first surface area; a second part of the second surface area of the second fabric layer, the second part being less than 25% of the second surface area; and a third part of the third surface area of the fabric structure, the third part being less than 25% of the third surface area, wherein the first part is inferior to a horizontally-oriented centerline and medial to a vertically-oriented centerline of the first fabric layer, and wherein the second part is inferior to a horizontally-oriented centerline of the second fabric layer, wherein the third part extends substantially from the onlay mesh to the sublay mesh and connects the first part and the second part; and a keyhole in the first fabric layer configured to properly fit the critical structures of the patient therethrough without constriction, wherein the keyhole is substantially centered at about 30% to 50% of a vertical height of the first fabric layer. In certain embodiments, at least a portion of the first fabric layer is barrier-free, the portion being greater than 75% of the first surface area, and wherein the at least a portion of the fabric layer comprise a first region superior to the horizontally-oriented centerline and a second region lateral to the vertically-oriented centerline. In certain embodiments, at least a portion of the second fabric layer is barrier-free, the portion being greater than 75% of the second surface area, and wherein the at least a portion of the fabric layer comprise a first region superior to the horizontally-oriented centerline, a second region lateral to the vertical centerline, and a third region medial to the vertical centerline. In certain embodiments, the critical structures comprise a spermatic cord and its content and a genital nerve of a male patient, or a genital nerve of a female patient. In certain embodiments, the keyhole is lateral to a vertical centerline of the first fabric layer. In certain embodiments, the third surface area is a tubular surface area of the tubular mesh. In certain embodiments, the third part is in an inferolateral quarter of the tubular surface. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

In yet another aspect, disclosed herein are implantable meshes for inlay inguinal hernia repair in a patient, comprising: a fabric layer comprising an outer side defining a surface area, the fabric layer being foldable; an anti-adhesive barrier comprising a shape configured to prevent direct contact between the fabric layer and critical structures of the patient upon implantation, wherein the shape covers at least a portion of the outer side, the portion being no greater than 50% of the surface area, wherein the shape is limited to be within a predetermined distance to an anterior edge of the outer side, wherein the shape extends substantially from a posterior edge of the outer side. In some embodiments, the predetermined distance is about 1 cm. In some cases, the keyhole is partly or completely surrounded by said barrier on at least one side of the fabric layer. In some cases, the fabric layer is synthetic, biologic, or hybrid. In some cases, the anti-adhesive barrier is synthetic, biological, or hybrid. In some cases, the anti-adhesive barrier is absorbable by surrounding tissues. In some cases, the anti-adhesive barrier is at least partly absorbed after at least one week post implantation. In some cases, the anti-adhesive barrier is permanent. In some cases, the anti-adhesive barrier is configured to be positioned lateral to a midline line of the patient on a left side or on a right side upon implantation. In some cases, the mesh is configured to be implanted lateral to a midline of the patient on a left side or on a right side upon implantation.

Overview

The present invention relates to implants used for repairing an inguinal hernia. In some cases, inguinal hernias include all hernias of the groin. In some cases, inguinal hernia includes but is not limited to indirect and directs inguinal hernias, femoral hernias, and obturator hernias. Typically, implantable mesh (generally sheets of mesh having two flat sides) adheres to the subject's tissue on both flat sides following and/or during an inflammatory response to the implantation of the device. The goal of hernia repair is for this adhesion to occur on both flat sides of a mesh, however, adhesion of a mesh to certain anatomical structures at the implantation site can cause functional deterioration, pain, and other effects which are difficult to treat and can cause life-long debility.

In some embodiments, the mesh, scaffold, or other implant, whether synthetic or non-synthetic, used for the intention of inguinal hernia repair are herein referred as a group termed "mesh." In some cases, implants as disclosed herein include but are not limited to meshes, biologics, allografts, xenografts, scaffolds, bioactive synthetic meshes, absorbable meshes, non-absorbable meshes, hybrid products, and implants made of other biomaterials. In some cases, for the simplicity of language, "mesh" is equivalent to "implant" as disclosed herein.

In some cases, an optimal mesh repair of an inguinal hernia is to have selective adhesion of the mesh onto the abdominal and pelvic floor structures that support the hernia defect which includes but are not limited to nearby muscles, fascias, and ligaments, without adhesion to critical structures including but not limited to nerves (including a genital nerve) and optionally the round ligament in female and the spermatic cord and its content and nerves (including a genital nerve) in males. In some cases, by adding an adhesion barrier to areas on the mesh that are at risk for adherence or tissue ingrowth, selective adhesion and optimal hernia repair are achieved.

In some cases, implants as disclosed herein include one or more selected from: a synthetic implant, a partially synthetic implant, and a non-synthetic implant. In some cases, implants as disclosed herein include but are not limited to meshes, biologics, allografts, xenografts, scaffolds, bioactive synthetic meshes, absorbable meshes, non-absorbable meshes, hybrid products, and implants made of other biomaterials.

The devices and methods disclosed herein may include mesh for implantation during different surgical procedures, for non-limiting examples, open inguinal surgery, laparoscopic surgery, or robotic-assisted surgery. The devices and methods disclosed herein may include mesh for implantation at different location, for non-limiting example, left or right of the midline of the body, on top of muscle, and/or behind the muscle. The technique for mesh implantation may be open, laparoscopic, or robotic-assisted, and this does not vary greatly between males and females. The onlay, sublay, or hybrid techniques may not be significantly variable between males and females. The purpose of this application is not to change the operative technique for inguinal hernia repair, rather to only improve the mesh implant to address gender-based differences in pelvic anatomy and its content and thus reduce complications.

The devices and methods disclosed herein may include gender-specific features and designs. The male and female pelvic anatomies vary in size, structure, and content. The average male pelvis is narrower, longer and deeper whereas the average female pelvis is wider, broader, shorter, and shallower as compared to average male pelvis. In order to maximize the adherence of mesh to normal abdominal and pelvic structures while maintaining the minimal necessary barrier against critical structures and reducing mesh-related chronic pain, there may be a difference in design of the mesh product and method of barrier application between male and female mesh products. The devices and methods disclosed herein may include gender-specific features so that the spermatic cord content of the male patient is well protected. These gender-specific features may include one or more structural features of the mesh and its elements. These gender-specific features may include one or more material features of the mesh and its elements. These gender-specific features may include one or more method features of implanting the mesh and its elements. As non-limiting examples, these gender-specific features may include one or more selected from: thickness of the barrier, thickness of a fabric layer, the width and/or position of the slit-like structure, size of the key-hole like structure, thickness of the key-hole like structure, position of the key-hole like structure, weave pattern of the mesh, shape of the mesh, size of the mesh, thickness of the mesh, or the like.

In some cases, meshes are flat or nearly-flat sheets and are two-dimensional, as can been seen in FIGS. 1-3, and 5-14. They have two sides to its flatness: an anterior (or ventral) and posterior (or dorsal) side. This connotation is made based on its position after implantation in the body. In some embodiments, for inguinal hernia repair, both sides of the mesh may adhere to the body in order to provide for a secure repair, without mesh migration post procedure. The devices and methods disclosed herein may lower the recurrence rate of hernia repairs without adding tension to the repair of the defect. In some cases, meshes have a three-dimensional design, as can been see in FIGS. 4 and 15. In some cases, mesh includes an inlay component that is intended to plug the hernia defect or lay within the inguinal canal. In this situation, the inlay portion of the mesh is immediately in contact with critical structures adjacent to it within the inguinal canal, which includes but is not limited to the spermatic cord, the genital branch of the genitofemoral nerve, or both.

In some cases, mesh that has poor or slow adhesion to its surroundings is more likely to fail, thereby hernia repair using mesh that is poorly adherent has a higher hernia recurrence rate, higher seroma rate, and the mesh is more likely to migrate. Thus, the devices disclosed herein have an initial inflammatory stage in which the device may adhere to typically but not limited to muscle, ligament, or fascia, as possible, and may have relatively rapid and relatively strong tissue ingrowth from as much normal healthy vascular tissue.

In some cases, during the initial inflammation stage of the mesh, it also adheres to and is involved in tissue ingrowth with structures that can result in postoperative pain, discomfort, functional deterioration, and sexual impairment. In some cases, these structures include but are not limited to the spermatic cord and its contents as well as nearby nerves. Non-limiting example of these structures includes the genital branch of the genitofemoral nerve and the nerves along the vas deferens, which runs within the spermatic cord. In some cases, adherence of the mesh to undesired tissues or regions occurs with both flat and three-dimensional mesh designs. In some cases, such undesired adherence causes chronic groin pain, pelvic pain, and/or pain with sexual intercourse and orgasm. Males may also suffer from testicular pain and infertility.

The devices and methods disclosed herein may include gender-specific features. These gender-specific features may include one or more selected from: thickness, density, weight, size, or shape of the fabric layer; material of the fabric layer; pore size of the fabric layer; lateral width of the fabric layer; width of the slit-like structure; size, thickness, shape, and position of the key-hole like structure; size, shape, position of the barrier, material of the barrier, or a combination thereof. The devices and methods disclosed herein may include mesh for implantation with different surgical procedures, e.g., open or laparoscopic techniques. The devices and methods disclosed herein may include mesh for implantation at different location, i.e., to the left or right of the midline of the body, on top of inguinal floor muscle or behind the inguinal and pelvic floor muscle. The spermatic cord runs through this muscle, via the inguinal canal. The spermatic cord includes a combination of spermatic cord, vas deferens, vasal nerves, testicular vessels, genital branch of the genitofemoral nerve, and cremasteric muscle.

In some embodiments, the implantable mesh for inguinal hernia repair disclosed herein is synthetic. In further embodiments, the fabric layer, the anti-adhesive barrier, or both the fabric layer and the anti-adhesive barrier are synthetic. In some embodiments, the synthetic mesh is made of one or more synthetic materials selected from one or more selected from but not limited to: polypropylene, polyester, expanded Polytetrafluoroethylene (ePTFE), and polymer suitable for inguinal floor reconstruction. In some embodiments the fabric layer comprises an interlaced structure defining a plurality of interstitial openings (alternatively called interstices herein).

In some embodiments, the implantable mesh for inguinal hernia repair disclosed herein is a hybrid mesh. In some embodiments, a hybrid mesh includes at least one synthetic material and at least one biological material. In further embodiments, the fabric layer, the anti-adhesive barrier, or both the fabric layer and the anti-adhesive barrier are hybrid. In some embodiments, the fabric layer is synthetic, biological or hybrid. In some embodiments, the fabric layer is hybrid, and the anti-adhesive barrier is biological, or hybrid, or synthetic. In some embodiments, the biological material is absorbable over a pre-determined period of time by the human body. In some embodiments, the implantable mesh for inguinal hernia repair disclosed herein is a biological mesh. In some embodiments, the implantable mesh for inguinal hernia repair disclosed herein is a hybrid mesh combining at least a biological and a synthetic material in either the fabric layer, the barrier, or both the fabric layer and the barrier. In some embodiments, the implantable mesh for inguinal hernia repair disclosed herein is a hybrid mesh combining at least an absorbable material and a synthetic material in either the fabric layer, the barrier, the attachment means of the barrier, both the fabric layer and the barrier, both the barrier and the attachment means, or all three of the fabric layer, the barrier, and the attachment means. In some embodiments, the barrier includes one or more materials selected from but not limited to: collagen, calcium alginate, polyglactin, polyglycolic acid. In some embodiments, the barrier includes one or more materials selected from: a biological material, a synthetic material, Seprafilm® adhesion barrier, animal membranes, gold foil, mineral oil, rubber, Teflon, chemically modified sugars, cellulose, oxidized and/or regenerated cellulose. In some embodiments, the barrier includes but not limited to one or more materials selected from: Hyalobarrier, auto cross-linked polymers of hyaluronic acid (ACP®), SprayShield, PrevAdh®, Intercoat®, Evicel®, Surgiwrap®, CoSeal®, and Preclude®, ADCON® Gel, Sepragel™ ENT, INCERT™, Tenoglide™, Oxiplex®, REPEL CV®, or a combination thereof.

Figure 15:
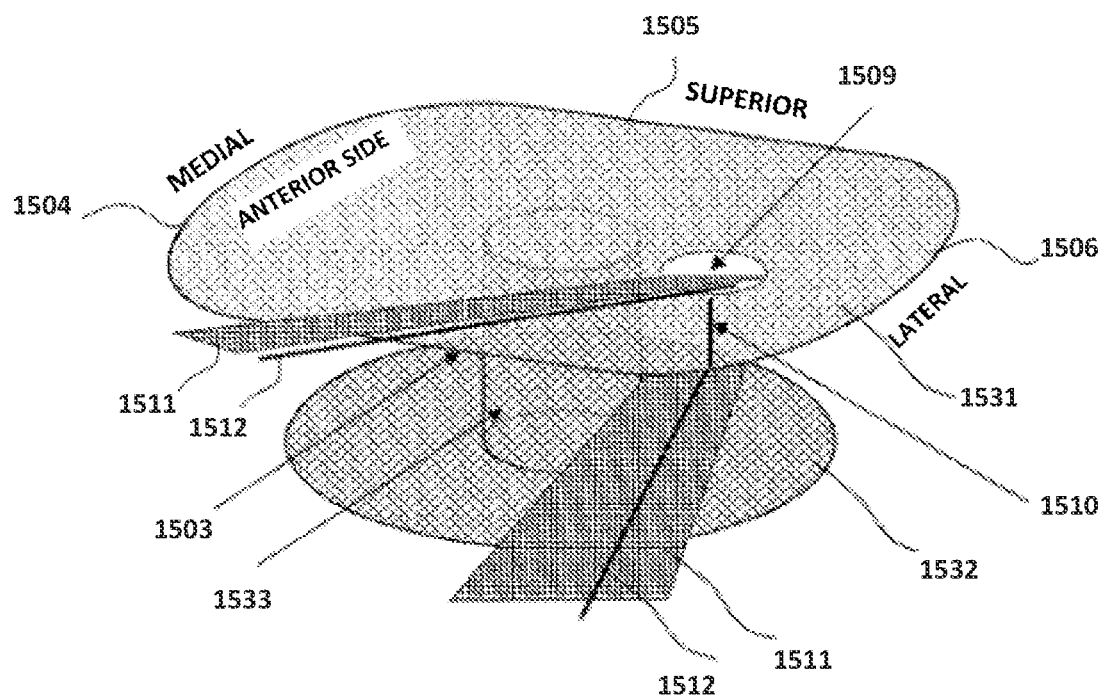
FIG. 15 shows another non-limiting example of a mesh for inguinal hernia repair described herein with anti-adhesive barrier viewing from the anterior/ventral side, in accordance with embodiments.
Figure 15:
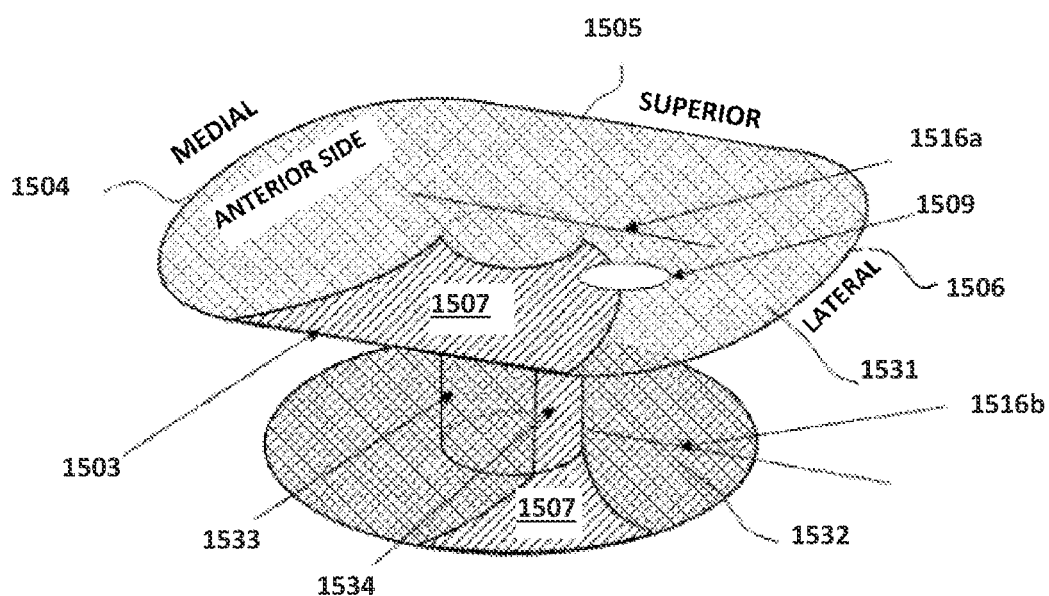

In some embodiments, the mesh may include one or more selected from but not limited to: a flat mesh, a 3-dimensional mesh, a preperitoneal mesh, an onlay mesh, a mesh plug, a Prolene hernia system (PHS) mesh, and a combination of these mesh categories. In some embodiments, a Prolene Hernia System (PHS®) mesh, as shown in FIG. 15, is a mesh that has two mesh layers and a mesh cylinder connecting the two mesh layers. In some embodiments, the top onlay mesh layer 1531 is connected by a hollow mesh tube 1533 to a bottom sublay mesh layer 1532. In some embodiments, the top and the bottom mesh layers have identical or different surface areas and/or surface shapes. In some embodiments, the mesh tube has a circular cross section, an oval cross section, a u-shaped cross section, a rectangular cross section, or other differently shaped cross sections.

In some embodiments, the mesh is intended to be positioned as a sublay or an onlay mesh such that the spermatic contents or a tube-like structure lays on top of (or anteriorly to) the mesh, underneath (posterior to) the mesh, and/or through the mesh contacting the anterior side, the posterior side, or both sides of the mesh. In further embodiments, the surface, anterior, posterior, ventral, or dorsal surface of mesh that contact the tube like structure or the spermatic cord includes the barrier that protects the tissue from contacting the synthetic part of the mesh, for non-limiting example, the fabric layer.

In some embodiments, the mesh is individually packaged sterilely or non-sterilely.

Gender-Specific Mesh for Male

A male-specific mesh, as can been seen in FIGS. 2-3, 4, 5-6, 7-9, may be configured to reduce chronic mesh-related pain. The male specific mesh may be a flat onlay (FIGS. 2-3, 5-6, 7-8) or a flat sublay (FIG. 9) mesh. An onlay mesh may be implanted anterior to a hernia defect and posterior or deep to the critical structures. A sublay mesh may be implanted posterior to a hernia defect and posterior or deep to the critical structures. Because the pelvis is rounded, and the anterior pelvis and posterior pelvis are both involved during retroperitoneal mesh placement, then there may be some portion of mesh (at the lower margin) which will lay flat but anterior to (ventral to, on top of) the spermatic cord, etc. at its most proximal area, but the mesh is substantially posterior to and deep to the critical structures.

In particular, the male specific mesh may be configured to reduce pain related to one or more selected from: mesh adhesion, mesh erosion, mesh entrapment of adjacent tissues (as nonlimiting examples, nerves and the spermatic cord and its contents). The male specific mesh may be configured to reduce activity-related pain caused by mesh implantation. Such pain may be related to sexual intercourse and/or orgasm. The male specific mesh may be configured to reduce injury or adhesion to spermatic cord, genital branch of genitofemoral nerve, or a combination thereof. The spermatic cord and its contents may include a spermatic cord, vas deferens, testicular vessels, or a combination thereof. The critical structures of a male patient may include a genitofemoral nerve or a genital nerve, and the spermatic cord and its contents.

The male specific mesh is configured to reduce testicular pain and/or infertility. In specific, the male specific mesh may be configured to, in addition to hernia repair, reduce pain from one or more selected from: mesh erosion into spermatic cord, mesh adhesion or erosion to the vasal nerves, mesh adhesion or erosion to the vas deferens, mesh adhesion or entrapment of spermatic cord vessels, mesh caused vessel obstruction, or a combination thereof. The male specific mesh may be configured to, in addition to hernia repair, reduce mesh erosion into vas deferens that may cause infertility, reduce mesh adhesion to or entrapment of spermatic cord vessels that may result in testicular atrophy.

In addition to inguinal hernia repair, a fin extending inferiorly to the inguinal ligament level or the iliopubic tract level, similar to the fin structures 1114, 1214, 1414, in shape, size, and/or function, may be added to the male-specific meshes as described herein. Such fin structure in male-specific mesh may provide femoral hernia repair in male patients and enable attachment at the most inferior tip of the fin to tissues in its vicinity. Thus a male-specific mesh may facilitate improved fixation of the mesh to the patient even during physical activities post-implantation while providing femoral hernia repair.

The male-specific mesh may be a flat onlay mesh, as can been seen in FIGS. 2-3, 5-6, 7-8. The flat onlay mesh may be substantially two-dimensional, in which the mesh may have a thickness to its third dimension that is substantially homogenous throughout the mesh. The flat onlay mesh may stay flat, become reshaped by body motion and other factors upon implantation to be within a three-dimensional space. Similarly, the female-specific mesh may be a two-dimensional or a three-dimensional mesh upon implantation. The onlay mesh may be used for open inguinal hernia repair.

Figure 2A:
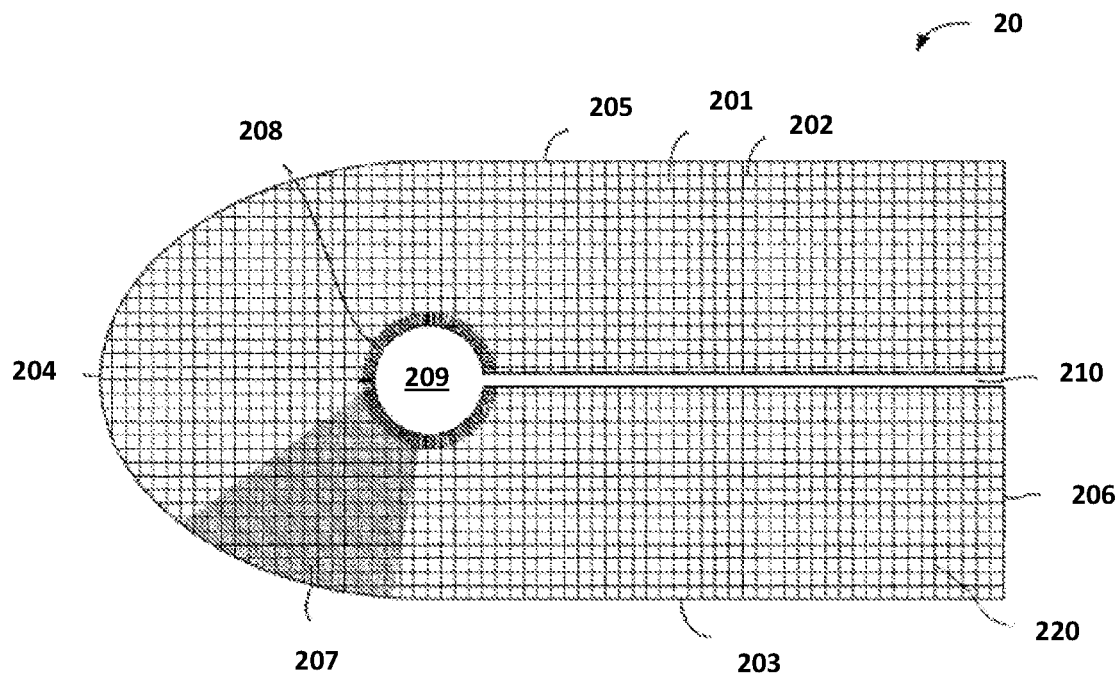
FIG. 2A shows another non-limiting example of a mesh for inguinal hernia repair in male patients described herein with anti-adhesive barrier, in accordance with embodiments.

Referring to FIG. 2A, in a particular embodiment, a flat onlay mesh 20 in an anterior (ventral) view may have an irregular shape with a curved medial edge 204 which connects smoothly and into a straight or curved superior edge 205 and a straight or less curved inferior edge 203. The lateral edge 206 may be straight and may connect with the superior edge and the inferior edge at its two ends. The mesh may be wider in the transverse direction than the longitudinal direction, such that the superior edge and the inferior edge are longer than the medial edge and the lateral edge. The overall mesh structure and the fabric layer may include uniformed pores 201 separated by braid structures 202. Alternatively, the fabric layer may be a flat sheet with no visible porosity and braid to it. A barrier 207, 208 may cover the circumference around a keyhole 209. The width of the barrier 208 extending radially outward from the circumference or edge of the keyhole may be about 1 cm. The barrier 207 may also cover a region defined at the infero-medial side of the mesh. The barrier 207 may radiate out from the keyhole to the inferomedial edge of the mesh (203). The outer circumference of the barrier 207 may range from about 3 cm to about 6 cm of the inferior edge 203 close to the tip of the medial edge 204. The mesh 20 is for use in male subjects. The distance to the tip of the medial edge from the medial-most location of the barrier 207 may be about 1 cm to about 2 cm, at least. The barrier may have a fan like shape starting from a portion of circumference of the keyhole 209 in the medial-inferior area. The portion may be about 25% to about 50% of the circumference. A slit 210 may initiate at the lateral edge 206 of the mesh 20 and makes connection to the keyhole. The slit may bisect the lateral mesh tails at about 30% to 50% mesh height along the superior-to-inferior direction from the inferior edge 203. In other words, the keyhole and/or the list may be at ⅓ or ½ of the mesh height. The barrier width may be monotonically increasing starting from the horizontal centerline (at 30% to 50% of mesh height, the mesh height being in the longitudinal direction of the patient upon implantation) of the mesh toward the inferior edge.

Figure 2B:
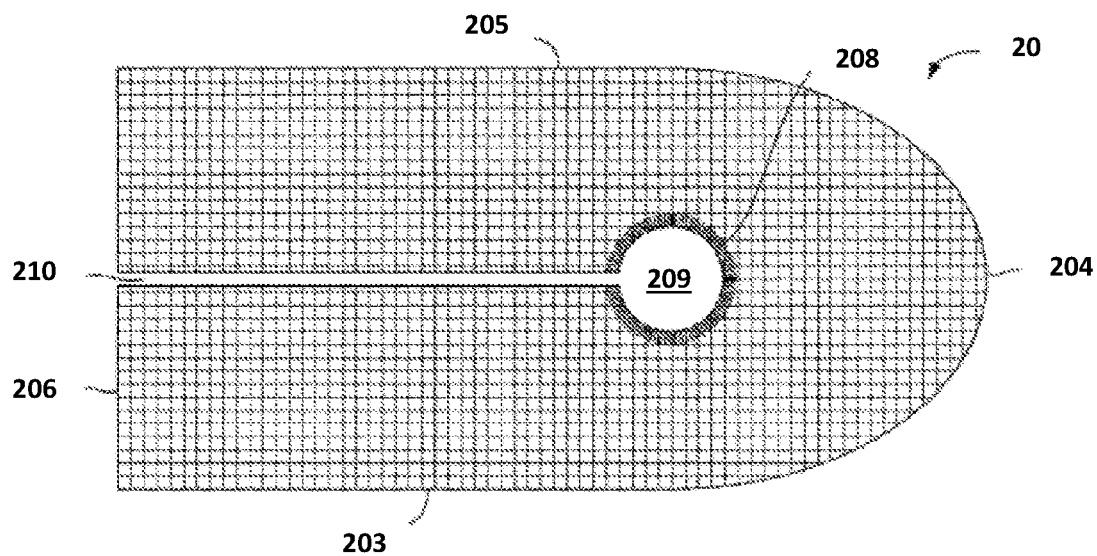
FIG. 2B is a posterior view of the mesh of FIG. 2A, in accordance with embodiments.

Referring to FIG. 2B, in a particular embodiment, a flat onlay mesh 20 in FIG. 2A is shown in a posterior (dorsal) view. The barrier 208 is applied along the circumference of the keyhole 209 with a barrier width of about 1 cm extending radially and outward from the edge of keyhole. On the posterior side, the barrier is not applied at the medial-interior edge as 207 of FIG. 2A.

Figure 7A:
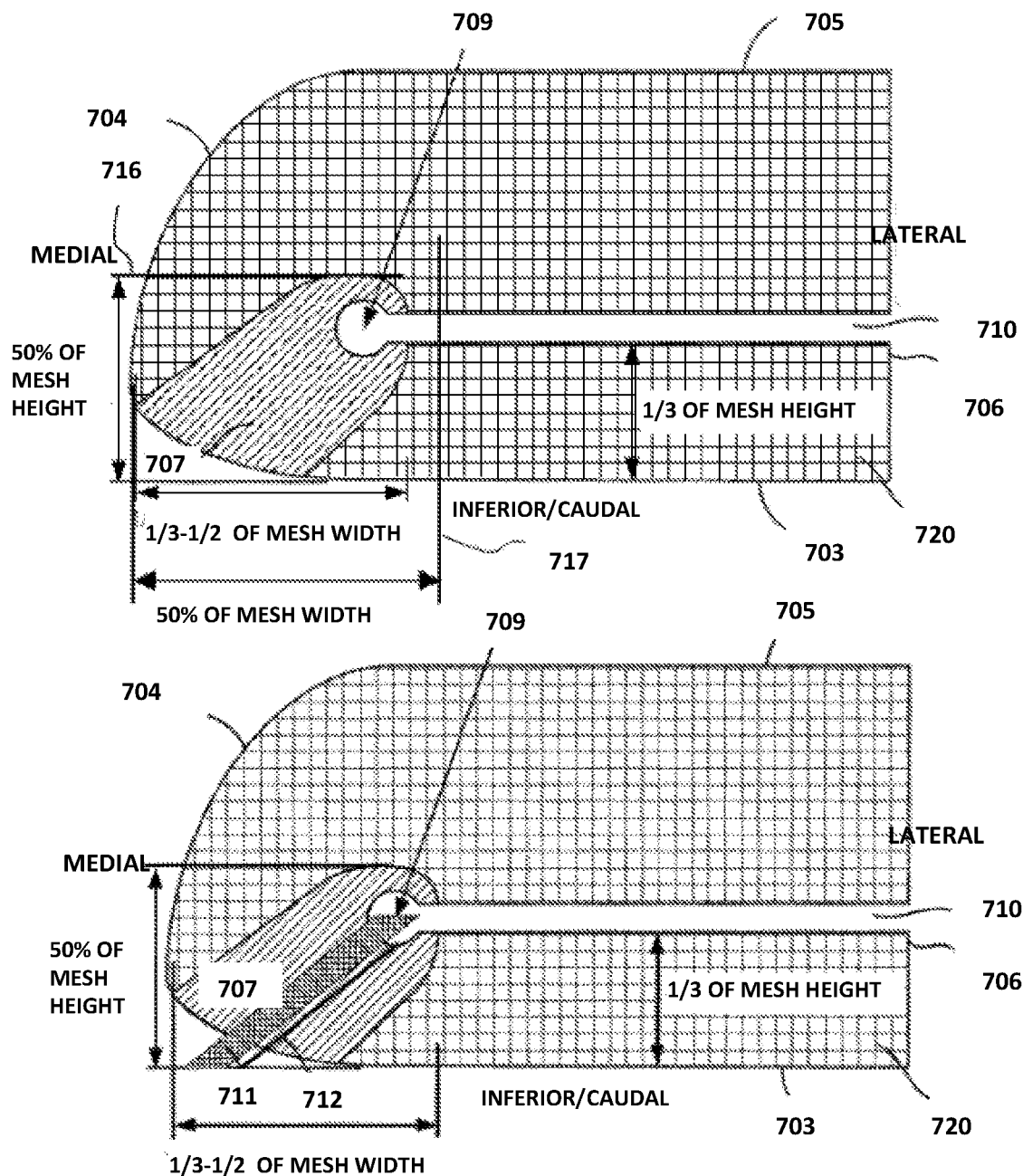
FIG. 7A shows another non-limiting example of a mesh for inguinal hernia repair in male patients described herein with anti-adhesive barrier viewing from the anterior/ventral side, in accordance with embodiments.

FIG. 7A shows a male-specific flat onlay mesh in an anterior (ventral) view. The mesh 70 may be implanted to the left of the midline of the patient. The curved medial edge 704 may be placed closer to the midline of the patient than the lateral edge 706. The barrier 707 may be pre-applied and/or customized on surgical site to a region on the medial-inferior side of the mesh. The region that the barrier occupies may have a height of about 50% of the height of the mesh along the inferior-to-superior direction. The barrier region may have a width of about 33% to about 50% of the width of the mesh laterally. The barrier edge may overlap with part of the medial edge 704 and the inferior edge 703, or both of the mesh. The barrier may have any suitable shape that is sufficient to cover the path of the spermatic cord without affecting desirable adhesion of and integration by other tissues onto the rest of the mesh. Thus, the barrier area may be kept to be less than about 25% of the total mesh area on the anterior side. The barrier may cover the inferomedial corner of the mesh on the anterior side. The mesh may comprise a pre-formed or customized keyhole 709, which may be partly or completely surrounded by the barrier 707. The keyhole may have a size and a shape that is sufficient to allow passage of the spermatic cord and its contents (spermatic cord, testicular vessels, and/or vas deferens) as 711, genital nerve as 712) of a male subject therethrough without squeezing. The keyhole may be joined by a slit 710 which optionally starts from a lateral edge of the mesh. The lower edge of the slit may be located at about 33% of the mesh height along the inferior-to-superior direction. The barrier may cover about 33% to about 50% of the inferior edge, the medial edge, or the inferior and medial edges in combination. The mesh may be wider in the transverse direction than the longitudinal direction, such that the superior edge and the inferior edge are longer than the medial edge and the lateral edge.

Figure 7B:
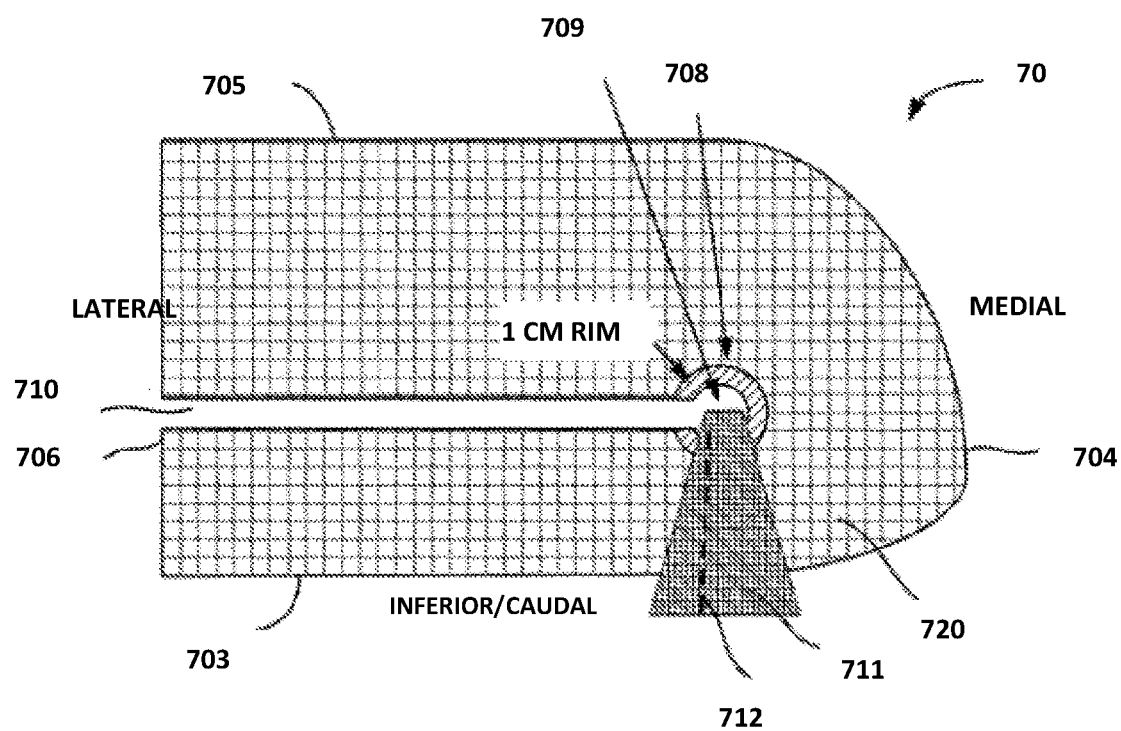
FIG. 7B shows a posterior view the mesh of FIG. 7A, in accordance with embodiments.

FIG. 7B shows a male-specific flat onlay mesh in a posterior (dorsal view). The mesh 70 may be implanted to the left of the midline of the patient. The barrier 708 on the posterior side of the mesh may include a rim around the keyhole 709. Such rim may be about 0.5 cm to about 1.5 cm wide. The spermatic cord and its contents, 711, including but not limited to testicular vessels and vas deferens, and genital nerve, 712, after the mesh is properly implanted, may only contact the keyhole and its immediate surrounding on the posterior side of the mesh. Such contact in the immediate surrounding of the keyhole area may be protected by a ring-shaped barrier 708.

Figure 8A:
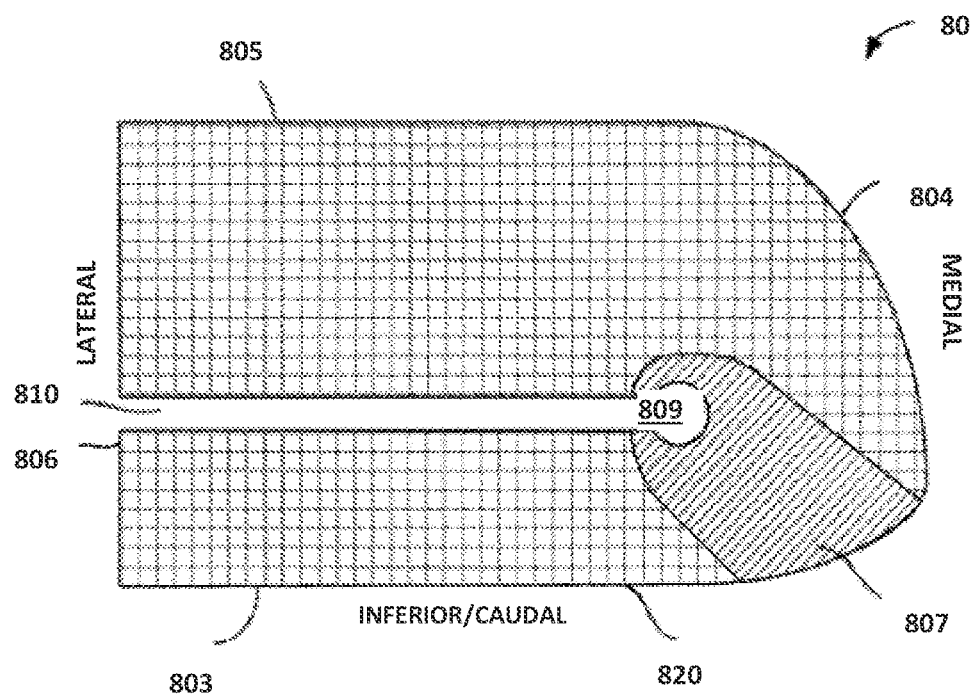
FIG. 8A shows another non-limiting example of a mesh for inguinal hernia repair in male patients described herein with anti-adhesive barrier viewing from the anterior/ventral side, in accordance with embodiments.

FIG. 8A shows a male-specific flat onlay mesh in an anterior (ventral view). The mesh 80 may be implanted substantially on the right-hand side of the midline of the patient. The curved medial edge 804 may be placed the closer to the midline of the patient than the lateral edge 806. The barrier 807 may be pre-applied and/or customized on surgical site to a region on the medial-inferior side of the mesh. The region that the barrier occupies may have a height of about 50% of the height of the mesh along the inferior-to-superior direction. The barrier region may have a width of about 33% to about 50% of the width of the mesh laterally. The barrier edge may overlap with part of the medial edge 804, the inferior edge 803, or both of the mesh. The barrier may have any suitable shape that is sufficient to cover the path of the spermatic cord without affecting desirable adhesion of and integration by other tissues onto the rest of the mesh. Thus, the barrier area may be kept to be less than about 25% of the total mesh area on the anterior side. The barrier may cover the inferomedial corner of the mesh on the anterior side. The mesh may comprise a pre-formed or customized keyhole 809, which may be partly or completely surrounded by the barrier 807. The keyhole may have a size and a shape that is sufficient to allow passage of the spermatic cord and its contents (711 in FIG. 7, genital nerve as 712 in FIG. 7) of a male subject therethrough without squeezing. The keyhole may be joined by a slit 810 which optionally starts from a lateral edge of the mesh. The lower edge of the slit may be located at about 33% of the mesh height along the inferior-to-superior direction. The slit width may be any suitable width that allows passage of the spermatic cord and its contents to the keyhole without constriction. The barrier may cover about 33% to about 50% of the inferior edge, the medial edge, or the inferior and medial edges in combination. The mesh may be wider in the transverse direction than the longitudinal direction, such that the superior edge and the inferior edge are longer than the medial edge and the lateral edge. Similarly to 707, the barrier 807 may be oblique to the vertical and horizontal centerlines, and it may have a shape that fans out from its most superior tip to its edges at the inferomedial corner of the mesh. Such shape and location of the barrier 807 may have similar advantages as disclosed herein for barrier 707.

Figure 8B:
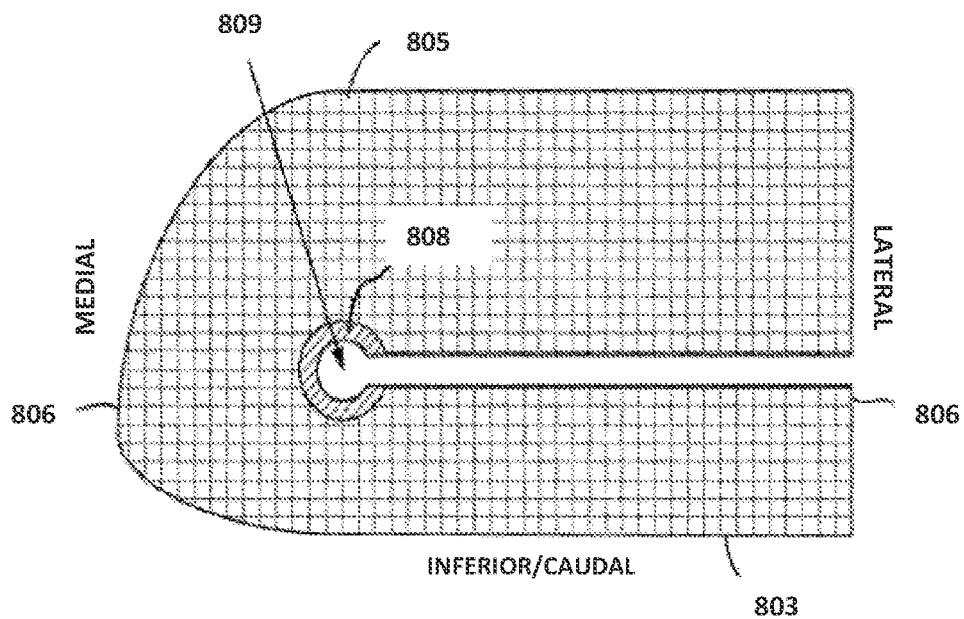
FIG. 8B shows a posterior view the mesh of FIG. 8A, in accordance with embodiments.

FIG. 8B shows a male-specific flat onlay mesh in a posterior (dorsal view). The mesh 80 may be implanted substantially to the right side of the midline of the patient. The barrier 808 on the posterior side of the mesh may include a rim around the keyhole 809. Such rim may be about 0.5 cm to about 1.5 cm wide. On the posterior side of the mesh, the spermatic cord and its contents (including testicular vessels and vas deferens) and genital nerve, after the mesh is properly implanted, may only contact the keyhole edges and its immediate surroundings. Such contact area may be protected by a ring-shaped barrier 808.

The barrier 207, 208, 707, 708, 807, 808 may have a variety of suitable sizes and shapes. The barrier 207, 208, 707, 708, 807, 808 may have any suitable size or shape that prevents direct contact between the spermatic cord and its contents and the fabric layer of the mesh after the mesh is implanted before the barrier starts to dissolve or disappear from the mesh. In addition, the barrier size or shape may not decrease the adhesion of other surrounding tissues to other areas of the fabric layer. Thus, the barrier size may be limited to an optimally small size that covers the area touching the spermatic cord content taking in consideration of cord movement during activities or mesh movement post implantation. In some cases, the barrier may be greater than about 10% to about 25% of the total mesh area on the anterior side. In some cases, the barrier may partly or completely surround the keyhole such that there may be a rim with barrier protection for no less than about 0.5 cm to about 1.5 cm around the keyhole (FIGS. 7A, B). In some cases, the barrier may partly cover the edge of the slit (FIGS. 7A,B) such that there may be a rim with barrier protection for no less than about 0.5 cm to about 1.5 cm at the edges of the slit(s) (FIGS. 7A,B). The barrier may extend to the lower edge of the mesh, which is the inferior edge. In other words, the barrier may be shaped to extend inferiorly from the keyhole, extends toward the inferior edge, and/or reaches inferior edge. The spermatic cord actually travels obliquely to cross the inguinal ligament toward the testicle, so an inferiorly and superiorly extending barrier may protect the entire trajectory of the spermatic cord and its contents.

As a nonlimiting example, the spermatic cord and its contents may travel in a variety of angles, mostly oblique, toward the bottom (inferior) edge of the mesh, reaching toward the testicle. Thus, the barrier may be wide enough to cover the pathway of the spermatic cord as the spermatic cord moves from the keyhole to the edge of the mesh, in order to make sure the pathway of the spermatic cord may be optimally protected by a barrier. The barrier may or may not have a symmetric shape by both side of the slit 210, 710, 810, 310. The mesh may be broader in the lateral-medial (transverse) direction than that of the superior-inferior (longitudinal) direction, especially for female subjects. The lateral-medial direction and the superior-inferior direction of the mesh may refer to the same direction of the patient upon mesh implantation. The transverse and longitudinal directions of the mesh may refer to the same direction of the patient upon mesh implantation.

The barrier 707, 807 may be oblique to a horizontal centerline 716 and a vertical centerline 717 of the mesh. A barrier edge starting from the most superior tip of the barrier and medial to the keyhole 709, 809 may be oblique to a horizontal centerline and a vertical centerline of the mesh. The oblique location and the fan-out shape of the barrier may be optimal to protect the critical structures 711, 712 from directly contacting the fabric layer thus prevent undesired adhesion thereto. Since the critical structures may naturally come into the keyhole in an oblique direction upon implantation and may move to a greater extend as its goes further away from the keyhole on the anterior side, such oblique location and the fan-out shape may provide optimal protection while allowing sufficient and optimal tissue adhesion in other uncovered area of the fabric layer. Similarly, an off-centered keyhole 709 inferior to the horizontal centerline may decrease the barrier size (when the barrier covers the circumference of the keyhole) while still may effectively protect the critical structures and additionally increase desired tissue adhesion to other part of the uncovered fabric layer. In addition, a part of the genital nerve 712 may run in parallel with the spermatic cord anterior to the onlay mesh upon implantation. Another part of the genital nerve 712 may also partly run more inferior to the spermatic cord 711 and in some regions anterior to the onlay mesh 70, 80. Thus, an oblique barrier may provide the advantage of protecting both the spermatic cord and its content and the genital nerve and prevent adhesion of the genital nerve to the fabric layer 720, 820, which significantly helps in preserving nerve function and preventing mesh-induce damages in male patients. As disclosed herein, the critical structures of a male patient may include nerves (including a genital nerve) and the spermatic cord and its contents, while the critical structures of a female patient may include nerves (including a genital nerve) and optionally the round ligament.

In some cases, the barrier 207, 307, 507, 607, 707, and 807 may be oblique to a horizontally-oriented centerline 516, 616, and 716 and a vertically-oriented centerline 517, 617, and 717. In some cases, the barrier is oblique such that a straight line connecting a center of the keyhole and a midpoint of an overlapping edge of said barrier and the fabric layer forms an angle with a vertically-oriented centerline, the angle being in a range of 30 degrees to 60 degrees. In some cases, the barrier is oblique such that a straight line connecting a center of the keyhole and a midpoint of an overlapping edge of said barrier and the fabric layer forms an angle with a horizontally-oriented centerline, the angle being in a range of 30 degrees to 60 degrees. In some cases, the barrier is oblique such that a straight line starting from a most superior tip of said barrier and ending in a most medial tip of said barrier forms an angle with a horizontally-oriented centerline, the angle being in a range of 30 degrees to 60 degrees. In some cases, the barrier is oblique such that an edge of said barrier starting from a most superior tip of said barrier and going medially ends in a point at an edge of the fabric layer, the point being at least 1 cm inferior to the keyhole and medial to a vertically-oriented centerline.

In some cases, mesh braiding of the fabric layer 220, 320, 420, 520, 620, 720, 820 may be variable. The width or length of the pore 101, 201, and 301 may be any number between 0.001 mm to 10 mm or more. In some cases, the mesh pore may be any two-dimensional shape. For nonlimiting examples, the pore may be square, rectangular, round, oval, triangle, hexagon, pentagon, diamond, fan, or a combination thereof. In some cases, the pore size may be variable across the mesh. Alternatively, the fabric layer may not have a weave or a braid at all so that the fabric layer may be a flat sheet without visible pores or without any pores.

It should be understood, that dimensions sizes and shapes are exemplary and that any suitable sizes and shapes may be employed for the mesh.

In some cases, the barrier as disclosed herein, for non-limiting examples, 207, 307, is pre-applied on the anterior side of the mesh. In further cases, the barrier is applied to a region that starts and fans out from a portion of the circumference of the keyhole. The portion of the circumference of the keyhole is anywhere between about 25% to about 50%. In some cases, the barrier as disclosed herein, for example, 208, 308, is pre-applied around a portion or the entirety the circumference of the keyhole. In some cases, the portion is anywhere between about 50% to about 100%. In some embodiments, the barrier is applied for a width of about 0.5 cm to about 1.5 cm extending outward radially from the circumference of the keyhole. The barrier may optionally cover a portion of the inner side or inner wall of the keyhole, and/or a portion or entirety of the inner side of the slit. The barrier may optionally cover a portion or the entirety of the wall of the mesh (in a third-dimension that is orthogonal to the mesh height and the mesh width, not shown), for example, at the medial edge, lateral edge, superior edge, interior edge, at the edge of the keyhole, at the edge of the slit, or a combination thereof. The barrier may optionally cover a portion of the wall of the fabric layer, the portion being where the barrier is applied and overlapped with on the anterior side of the mesh. The portion may be anywhere between about 1% to about 100%.

In some cases, the mesh as describe herein may be any shape that has a curved medial edge or a flat medial edge. The tip or peak of the medial curve may be pointing outward. The mesh may be any shape that has a substantially straight lateral edge or a curved lateral edge. In some cases, the mesh may be any shape that has a straight or curved inferior edge. In some cases, the mesh may be any shape that has a straight or curved superior edge. In some cases, the mesh may be any shape that has at least one smooth edge. In some cases, the mesh edges do not have any abrupt shape changes or transitions. As nonlimiting examples, the mesh has a shape of a square, a rectangle, a diamond, an oval, a trapezoid, a parallelogram, a round, a diamond, a u-shape, a bell-shape, a fan shape, a hexagon, a pentagon, or the like.

In some cases, the size and/or shape keyhole as described herein is predetermined on the mesh. In some cases, the barrier shape and/or size is predetermined relative to the keyhole on the mesh. Not all patients have similar anatomy, size. If the spermatic cord or other tube-like structure of a subject is not forced to enter at exactly where the predetermined keyhole is made, there may be potential for inadequate barrier coverage of the subject, thus may cause damage and injury to the subject. Alternatively, the keyhole may be cut in a mesh (FIGS. 5-6) by a medical professional with customized size and/or shape for a subject and/or the slit joining the keyhole. In this case, the barrier and its effects may remain unchanged as it provides sufficient coverage for a range of keyhole sizes and/or shapes.

In some cases, the barrier 207, 208, 707, 307, 308, 708, 807, and 808 does not extend to the superior half of the mesh. In some cases, the barrier does not extend to the superior half of the mesh except the area immediately surrounding the keyhole 209, 309, 709, 809. Extending the barrier to the superior half of the mesh may reduce the ability of the mesh to properly adhere to the appropriate areas in the body, and may increases risk for hernia recurrence by reducing the total surface area for adherence of the mesh. The barrier may extend to the lower edge of the mesh medially, inferiorly, or both. The spermatic cord may travel obliquely to cross the inguinal ligament toward the testicle, so it is important that its entire trajectory be protected. Thus, the barrier may extend to the lower edge of the mesh medially, inferiorly, or both. The barrier may run obliquely from surrounding area of the keyhole to the inferior-medial corner of the fabric layer 220, 320, 520, 620, 720, and 820.

The barrier 207, 208, 307, 308, 707, 708, 807, 808 may include protection of the spermatic cord at its entry—at the keyhole or slit that is cut. The keyhole and the slit may be where the most amounts of adhesion and thus damage occur. Damage can result from mesh adhesion, erosion, and/or shrinkage, resulting in spermatic cord injury, obstruction, and in some cases transection. The barrier may be on one or both of the surfaces of the fabrication of areas immediately adjacent to the keyhole and/or the slit. The barrier may cover at least a portion of the thickness of the fabrication at the keyhole and/or the slit. The barrier may cover at least a portion of the thickness of the fabrication at the keyhole or the slit. The barrier may cover at least a portion of a wall of a keyhole, a wall of a slit, or both. The barrier, the keyhole 209, 309, 709, 809 and/or the slit 210, 310, 710, 810 may not go beyond a horizontal centerline (516 in FIG. 5), wherein the horizontal centerline is at 50% of mesh height. The barrier, the keyhole 209, 309, 709 and/or the slit 210, 310, 710, 810 may not go beyond a vertical centerline, wherein the horizontal centerline is at 50% of mesh width.

Figure 3A:
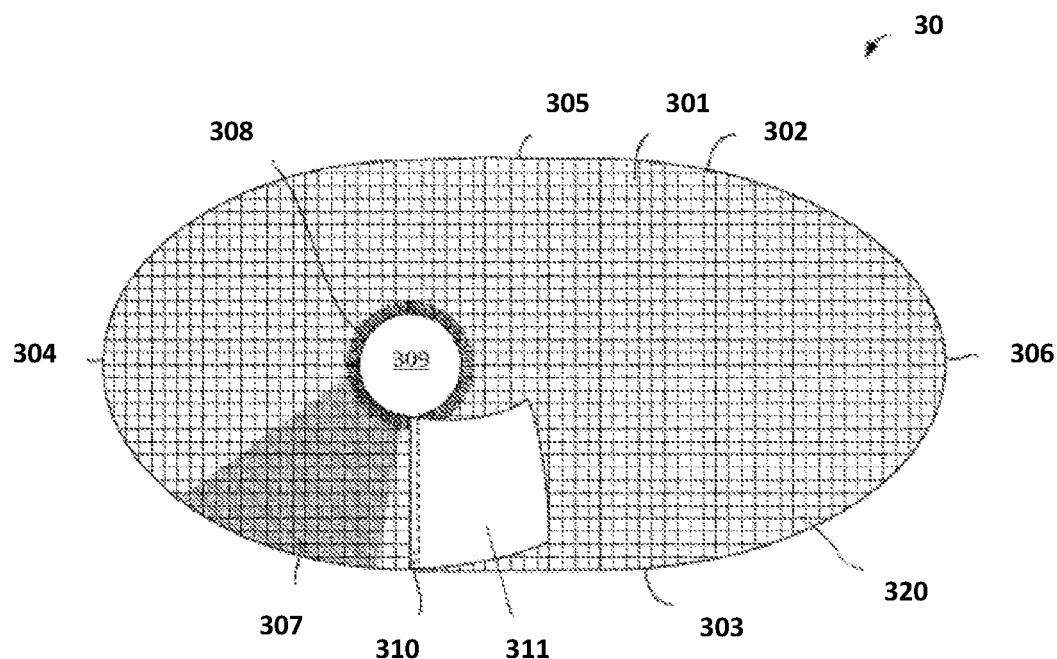
FIG. 3A shows another non-limiting example of a mesh for inguinal hernia repair in male patients described herein with anti-adhesive barrier, in accordance with embodiments.

Referring to FIG. 3A, in a particular embodiment, is a male specific flat only mesh 30 in an anterior view. The curved medial edge 304 may be placed closer to the midline of the patient than the lateral edge 306. The barrier 307 may be pre-applied and/or customized on surgical site to a region on the medial-inferior side of the mesh. The region that the barrier occupies may have a height of less than about 50% of the height of the mesh along the longitudinal (inferior-to-superior) direction. The barrier region may have a width of about 33% to about 50% of the width of the mesh horizontally. The barrier edge may extend to and overlap with part of the medial edge 304, the inferior edge 303, or both of the mesh. The barrier may have any suitable shape that is sufficient to cover the path of the spermatic cord without affecting desirable adhesion of and integration by other tissues onto the rest of the mesh. Thus, the barrier area may be kept to be less than about 25% of the total mesh area on the anterior side. The barrier may cover the inferomedial corner of the mesh on the anterior side. The mesh may comprise a pre¬formed or customized keyhole 309, the keyhole centered at about 50% of mesh height, which may be partly or completely surrounded by the barrier 307. The keyhole may have a size and a shape that is sufficient to allow passage of the spermatic cord contents and genital nerve of a male subject therethrough without constriction. The keyhole may be joined by a slit 310 which optionally starts from an inferior edge of the mesh. The mesh may additionally include a flap 311. The mesh may be wider in the longitudinal direction than transverse direction, such that the superior edge and the inferior edge are longer than the medial edge and the lateral edge.

Figure 3B:
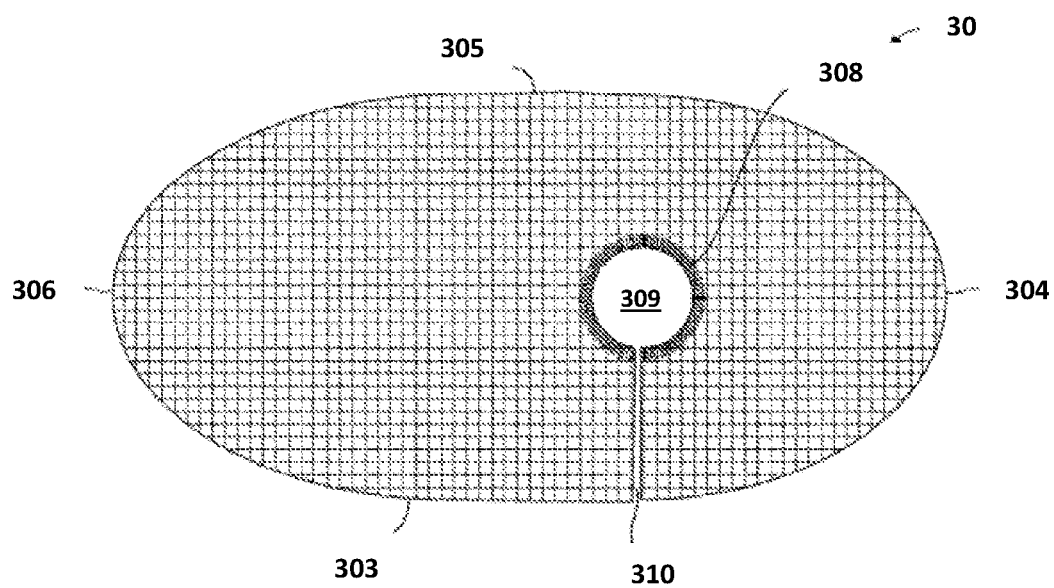
FIG. 3B is a posterior view of the mesh of FIG. 3A, in accordance with embodiments.

Referring to FIG. 3B, in a particular embodiment, a flat onlay mesh 30 in FIG. 3A is shown in a posterior (dorsal) view. The barrier 308 is applied along the circumference of the keyhole 309 with a barrier width of about 1 cm extending radially and outward from the edge of keyhole. On the posterior side, the barrier is not applied at the inferomedial edge as 307 of FIG. 3A.

In some cases, the closure flap 311 may have a shape suitable to cover the slit, the keyhole, or both. As nonlimiting examples, the closure flap has a shape that is substantially a rectangle, square, round, oval, trapezoid, triangle, circular sector, diamond, hexagon, pentagon, or the like. The closure flap has one side that is attached to the mesh, and the other side may be flappable or movable to allow access to the keyhole, and/or the slit and affixed to the mesh to close access to the keyhole, and/or the slit. The barrier may cover a portion or the entirety of the closure flap on its anterior side and/or its posterior side. The barrier may cover a portion of the closure flap that is in close vicinity to circumference of the keyhole when the flap is fixed on the mesh. The closure flap may be reversibly removable from the mesh. The portion of the closure flap is from about 1% to about 99%. The closure flap may not be restrictive to entrap the spermatic cord within the keyhole and result in potential injury and obstruction. The closure flap is to retain the spermatic cord content within the keyhole without re-herniation of content through the slit.

In some cases, the barrier 307 is applied so that there is no gap in barrier coverage toward the edge of the slit on the medial side of the slit. In other cases, the barrier ends before it touches a wall of the slit, thus there is a barrier gap between the barrier and the slit. In some cases, the barrier is only applied to the slit at its end at or in close vicinity (As nonlimiting example, in about 0.1 cm to about 2 cm) to the circumference of the keyhole. In some cases, an edge of the barrier closest to the slit and the wall of the slit are separated by an arbitrary shaped barrier gap. As nonlimiting examples, the arbitrary shape is substantially a triangle, a circular sector, a trapezoid, an oval, a rectangle, or the like with some cut-outs by the keyhole. In some cases, the flat two-dimensional mesh shape and the barrier are made of materials suitable for necessary reshaping (as nonlimiting examples, curving, bending, folding, or the like), so it changes into a shape in three-dimension during or after placement procedure. Such shape change may be variable depending on the surgeon and/or the patient.

Figure 5A:
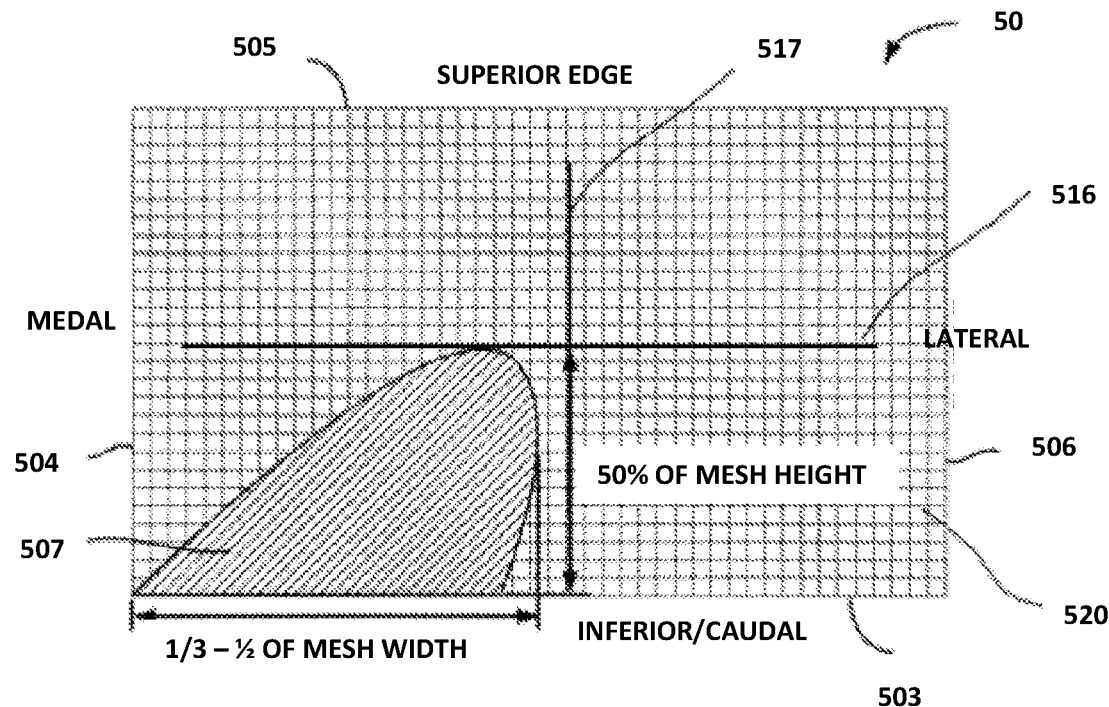
FIG. 5A shows another non-limiting example of a mesh for inguinal hernia repair in male patients described herein with anti-adhesive barrier viewing from the anterior/ventral side, in accordance with embodiments.
Figure 5A:
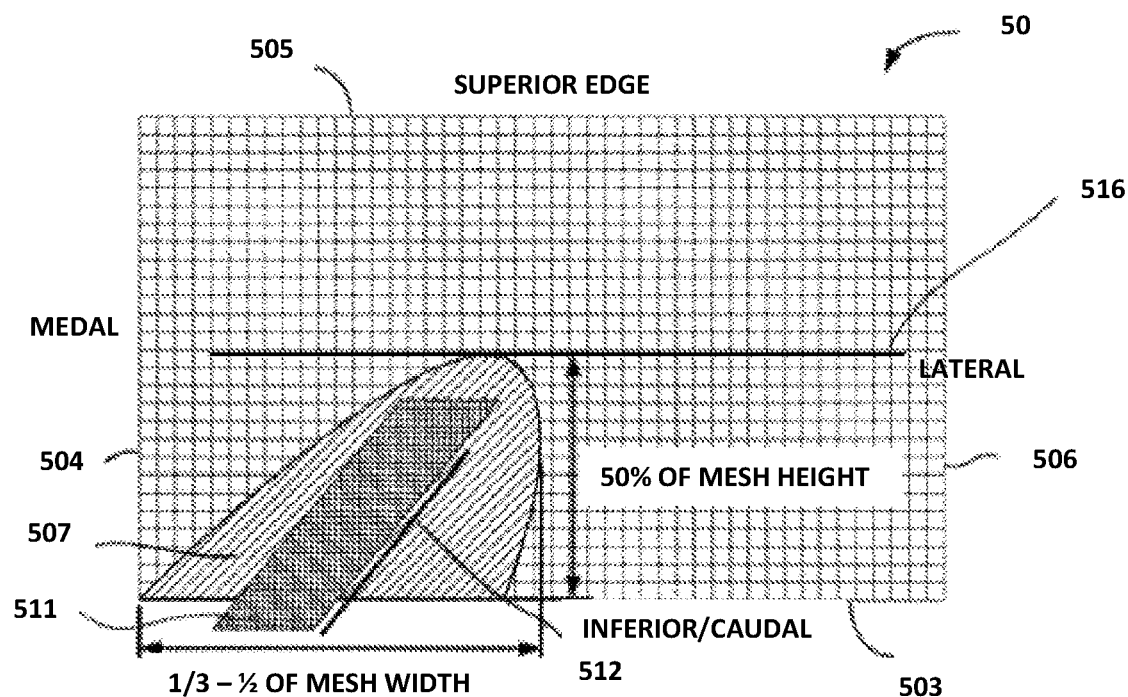

FIG. 5 shows a male-specific flat onlay mesh in an anterior (ventral view) which may be customized by the surgeon for implantation. The keyhole and/or the outer shape of the fabric layer including edges 503-506, can be cut or tailored. The mesh 50 may be implanted to the left of the midline of the patient. The medial edge 504 may be placed closer to the midline of the patient than the lateral edge 506. The four edges of the mesh may be straight lines. The mesh may be customized by a surgeon on site to include a keyhole and a slit, which may be partly or completely surrounded by the barrier 507. The barrier 507 may be pre-applied and/or customized on surgical site to a region on the inferomedial area of the mesh. The region that the barrier occupies may have a height of about 50% of the height of the mesh along the longitudinal (inferior-to-superior) direction, the longitudinal direction overlaps with the longitudinal direction of the patient upon implantation. Line 516 may represent a horizontal centerline at 50% of the mesh height. The barrier region may have a width of about 33% to about 50% of the width of the mesh laterally. The barrier edge may overlap with part of the superior edge 504, part of the inferior edge 503, or both of the mesh. The barrier 507 may have any suitable shape that is sufficient to cover the path of the spermatic cord without effecting desirable adhesion of other tissues to the rest of the mesh. Thus, the barrier area may be kept to be less than about 25% of the total mesh area on the anterior side. The barrier may cover the inferomedial corner of the mesh on the anterior side. The barrier may cover an oblique path starting from the inferomedial corner of the mesh to the center of where the surgeon would position the keyhole. The barrier may cover about 33% to about 50% of the inferior edge, the medial edge, or both. The barrier width may be monotonically increasing starting from the horizontal centerline 516 of the mesh toward the inferior edge. The barrier may not cover beyond the horizontal centerline toward the superior edge, wherein the horizontal centerline 516 is at 50% of mesh height. The barrier may not cover beyond the vertical centerline toward the lateral edge, wherein the vertical centerline is at 50% of mesh width. The keyhole may have a size and a shape that is sufficient to allow passage of the spermatic cord and its contents (spermatic cord 511, genital nerve 512) of a male subject therethrough without constriction. The keyhole may be joined by a slit which optionally starts from a lateral edge of the mesh. The slit width may be any suitable width that allows passage of the spermatic cord and its contents to the keyhole without constriction. The keyhole, the slit, or both may not go beyond the horizontal centerline 516 to the superior half of the mesh. The mesh may be wider in the transverse direction than the longitudinal direction, such that the superior edge and the inferior edge are longer than the medial edge and the lateral edge.

Figure 5B:
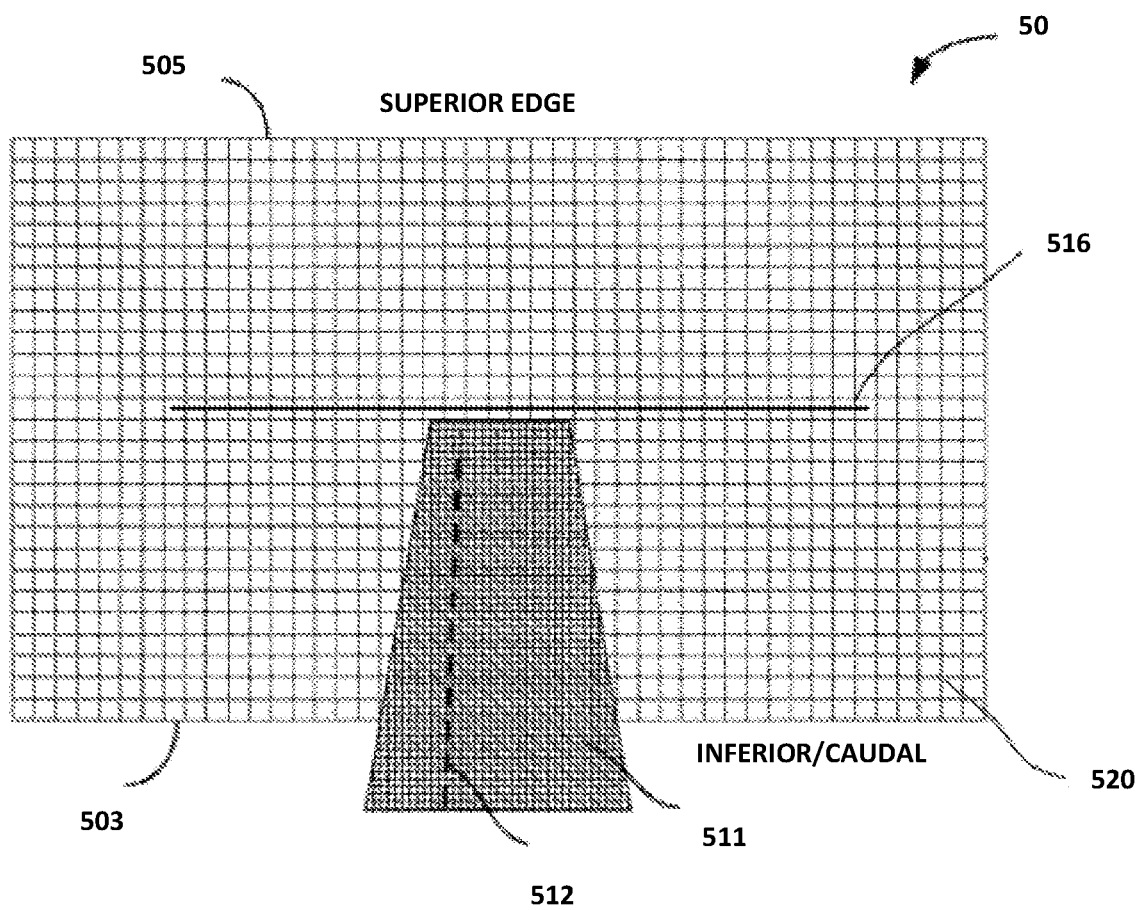
FIG. 5B shows a posterior view the mesh of FIG. 5A, in accordance with embodiments.

FIG. 5B shows a male-specific flat onlay mesh in a posterior (dorsal view). The mesh 50 may be implanted to the left of the midline of the patient. There may be no barrier on the posterior side of the mesh, as this mesh is intended for onlay mesh placement (mesh is positioned on top of the muscle). The spermatic cord and its contents 511, genital nerve 512, after the mesh is properly implanted, may be positioned at an angle that is not substantially parallel to the mesh optionally from the inferior edge of the mesh, such that the spermatic cord content may only contact the mesh at the edge of keyhole as it pierces the mesh. Posteriorly, the spermatic cord and its contents only interact with the mesh at the keyhole.

Figure 6:
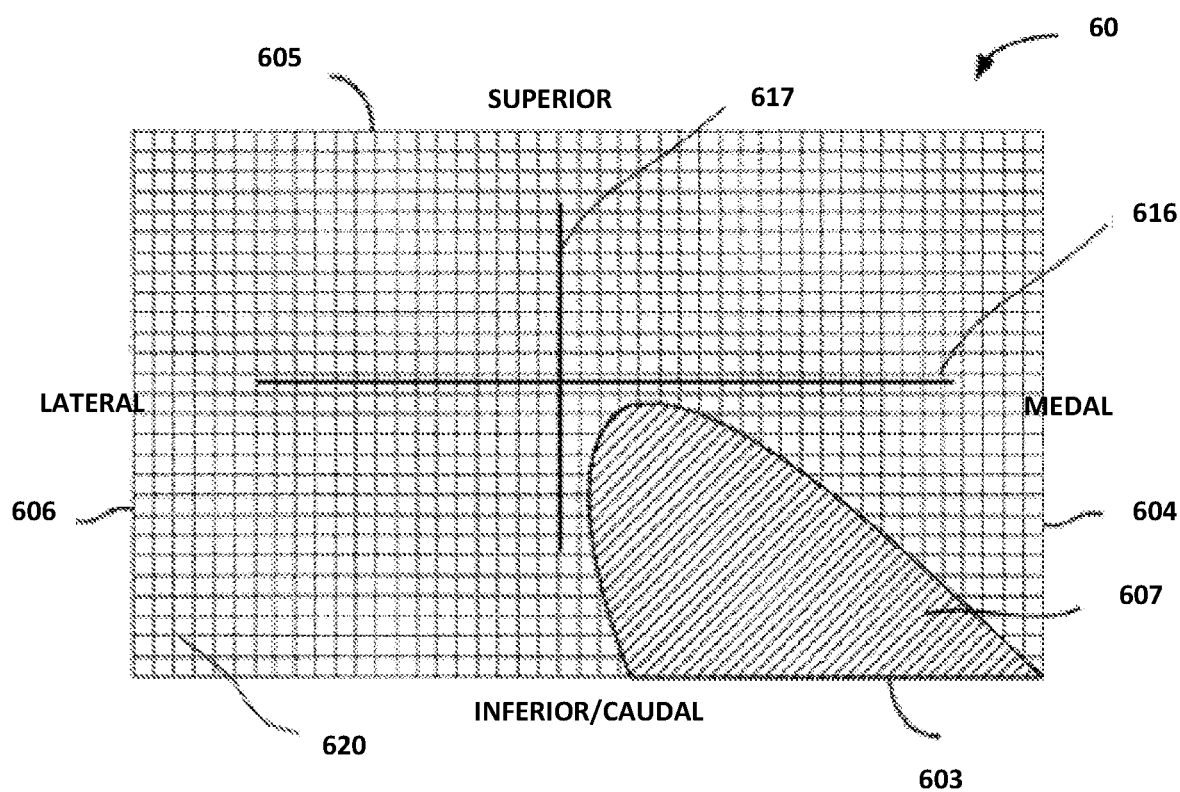
FIG. 6 shows another non-limiting example of a mesh for inguinal hernia repair in male patients described herein with anti-adhesive barrier viewing from the anterior/ventral side, in accordance with embodiments.

FIG. 6 shows a male-specific flat onlay mesh in an anterior (ventral view) which may be customized by the surgeon for implantation into various patients. The keyhole and/or, the outer shape of the mesh, including the edges 603-306, may be cut or tailored. The mesh 60 may be implanted to the right side of the midline of the patient. The medial edge 604 may be placed closer to the midline of the patient than the lateral edge 606. The four edges of the mesh may be straight lines. The barrier 607 may be pre-applied and/or customized on surgical site to a region on the inferomedial area of the mesh. The region that the barrier occupies may have a height of about 50% of the height of the mesh along the longitudinal (inferior-to-superior) direction, the longitudinal direction overlaps with the longitudinal direction of the patient upon implantation. Line 616 represents a horizontal centerline at 50% of the mesh height. The barrier region may have a width of about 33% to about 50% of the width of the mesh laterally. The barrier edge may overlap with part of the superior edge 604, part of the inferior edge 603, or both of the mesh. The barrier may have any suitable shape that is sufficient to cover the path of the spermatic cord and the genital nerve without affecting desirable adhesion of other tissues to the rest of the mesh. Thus, the barrier area may be kept to be less than about 25% of the total mesh area on the anterior side. The barrier may cover the inferomedial corner of the mesh on the anterior side. The barrier may cover an oblique path starting from the inferomedial corner of the mesh to the center of the keyhole, the keyhole being at where the surgeon would cut it. The barrier may cover about 33% to about 50% of the inferior edge, the medial edge, or both. The barrier width may be monotonically increasing starting from the horizontal centerline 616 of the mesh toward the inferior edge. The barrier may not cover beyond the horizontal centerline toward the superior edge, wherein the horizontal centerline 616 is at 50% of mesh height. The barrier may not cover beyond the vertical centerline toward the lateral edge, wherein the vertical centerline is at 50% of mesh width. The mesh may be customized by a surgeon on site to include a keyhole and a slit, which may be partly or completely surrounded by the barrier 607. The keyhole may have a size and a shape that is sufficient to allow passage of the spermatic cord and its contents of a male subject therethrough without constriction. The keyhole may be joined by a slit which optionally starts from a lateral edge of the mesh. The slit width may be any suitable width that allows passage of the spermatic cord and its contents to the keyhole without constriction. There may be no barrier on the posterior side of the mesh. The barrier width may be monotonically increasing starting from the horizontal centerline 616 of the mesh toward the inferior edge. The posterior side of the mesh 60 and the placement of the spermatic cord and its contents may look identical to the posterior side of the mesh 50 which is shown in FIG. 5B. The flat onlay mesh 50, 60 for male patients may be cut or tailored by a surgeon to include a customized keyhole with or without a customized slit. The customized keyhole may be cut completely or partly within the barrier such that the spermatic cord 511 and genital nerve 512 may go through the keyhole without contacting mesh areas that are not covered by the barrier on the anterior side. On the posterior side, the spermatic cord and genital nerve may come into the keyhole in a way such that it may not contact areas that are not covered by the barrier. Specifically, the spermatic cord and the genital nerve may converge substantially in the mesh posteriorly to pierce the mesh via an internal ring of the patient (designated by the keyhole) from a perpendicular angle to the muscle/pelvic wall and/or the posterior side of the mesh (FIGS. 5B, 7B). The onlay mesh may be used for females with the precut or tailored keyhole and/or slit to accommodate the round ligament and genital nerve of a female in a similar fashion as the spermatic cord. In specific, the keyhole and/or slit width may be smaller for female usage to optimally fit the round ligament therethough with minimization of an undesired patulous keyhole. In some cases, the customized keyhole, the customized slit, or both may be cut such that the entirety or the majority of keyhole and slit area is below the horizontal centerline 516, 616 of the mesh, wherein the horizontal centerline is at 50% of mesh height. In some cases, the customized keyhole, the customized slit, or both may be cut such that the entirety or the majority of keyhole and slit area does not go beyond a vertical centerline to the lateral half of the mesh, wherein the vertical centerline is at 50% mesh width.

The male-specific mesh may have a pre-shaped medial edge, as can be seen in FIGS. 2, 3, 7, 8. Alternatively, one or more edges of the mesh may be customized to fit to various need of the patient. Further, the area of the barrier may be shaped to maintain sufficient protection to the spermatic cord and its contents while increase desired tissue adhesion to the mesh area. Further the area of the barrier may be shaped by a medical professional now such that excessive barrier area may be removed to allow desired tissue (tissue other than spermatic cord and its contents) adhesion to the mesh. Alternatively, the medial edge may be cut or tailored by medical professionals to customize the fit to various patients. The mesh may be wider in the transverse direction than the longitudinal direction, such that the superior edge and the inferior edge are longer than the medial edge and the lateral edge.

In some embodiments, the fabric layer of the mesh is only partly covered by the anti-adhesive barrier on at least one side or only one side of the fabric layer. As in FIGS. 2-3 and 5-8, the flat onlay mesh for male may include a barrier of various suitable shapes so that the spermatic cord and its contents are not directly exposed to the fabric layer when the mesh is properly inserted and the barrier is not absorbed.

The male-specific mesh or female-specific mesh, either onlay mesh or sublay mesh, may have left-side or right-side variations depending on where the mesh is implanted relative to the midline of the patient. Left-sided mesh or right-sided mesh may be selected to provide optimal repair coverage for the respective inguinal hernia in different patients. Such left-side and right-side variation accommodates for differences in inguinal hernia locations and repair. It may assure that the barriers that are applied appropriately match the mirrored anatomy of the left and right inguinal region. This may allow for maximization of exposed mesh to areas that require adhesion, nonlimiting examples of tissue requiring adhesion including but not limited to the muscle, fascia, and/or periosteum, which may improve implantation outcomes over meshes with no left-side and right-side variations, improvements including lower recurrence rates for hernia, while at the same time, the left-side or right-side variation of meshes will minimize adhesion of mesh to critical structures such as genital nerve in males and females and spermatic cord content in males.

Figure 9B:
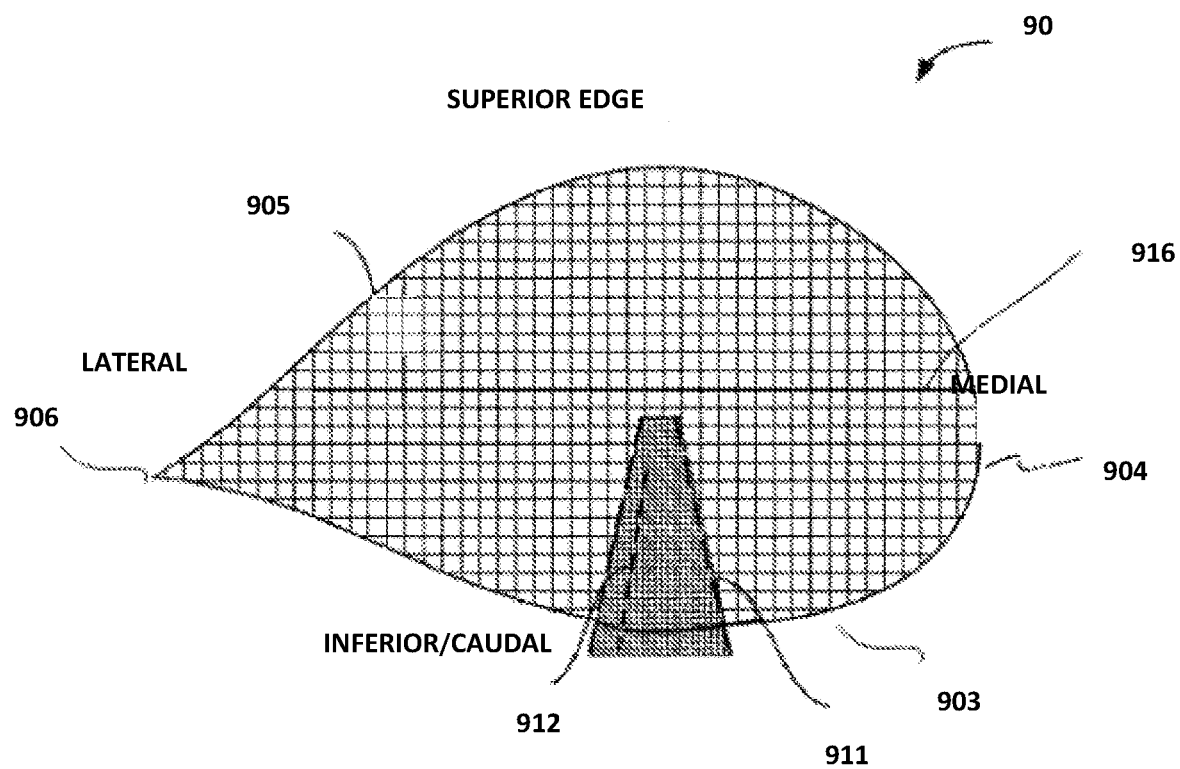
FIG. 9B shows a posterior view the mesh of FIG. 9A, in accordance with embodiments.
Figure 9C:
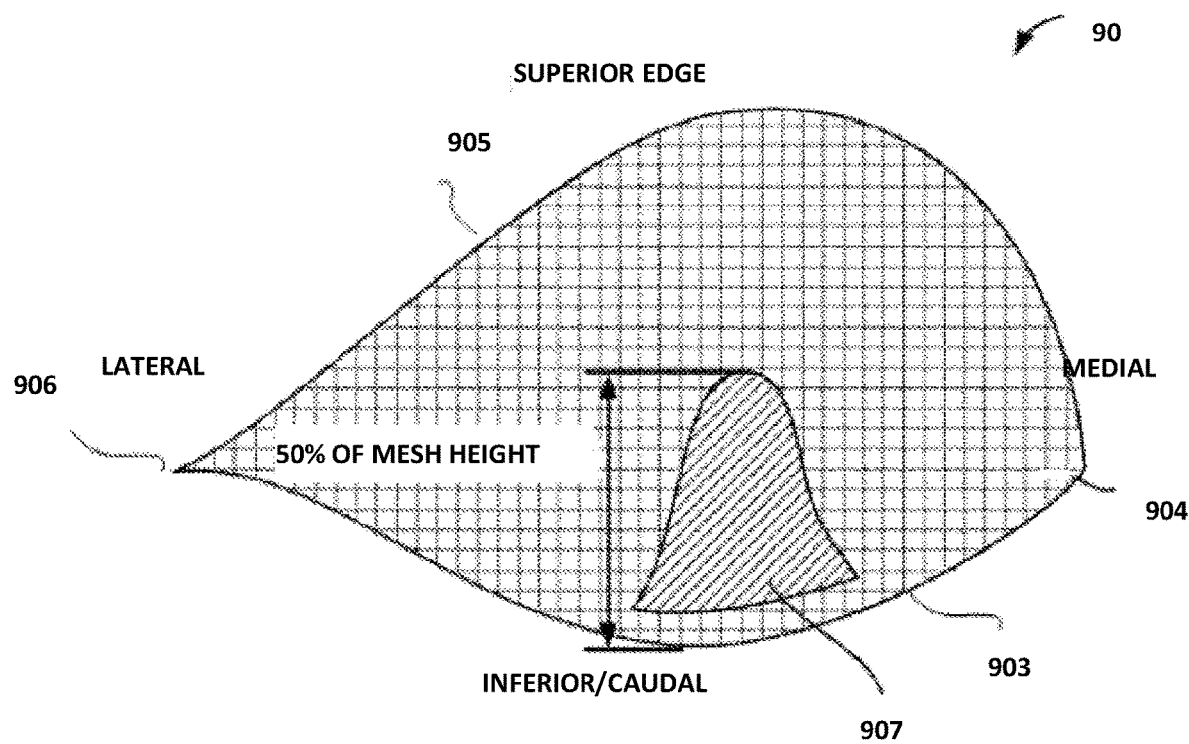
FIG. 9C shows another non-limiting example of a mesh for inguinal hernia repair described herein with anti-adhesive barrier viewing from the anterior/ventral side, in accordance with embodiments.

The male-specific mesh may be used as a sublay mesh (FIGS. 9A-9C). Sublay mesh may be configured for usage in laparoscopic inguinal hernia repair, robotic-assisted inguinal hernia repair, open retromuscular hernia repair, or any other suitable inguinal hernia repair procedures that involves mesh placement deep to (posterior to) the inguinal floor and pelvic muscles. FIG. 9A shows a flat or a three-dimensional sublay mesh specifically for usage in a male patient in an anterior view. The sublay mesh may be implanted to the left side of the midline of the patient. The sublay mesh 90 may have an arbitrary two-dimensional or 3-dimensional shape that is placed behind (more posterior to) the spermatic cord and hernia area. The sublay mesh may have one or more curved edges or may be flat on its edges. The sublay mesh may have a pre-shaped water-drop configuration, widest medially and tapered laterally. It may also have a more rectangular shape that allows for the surgeon to tailor the mesh by cutting it to the desired shape. In the curved configuration, the superior edge 905 and curved inferior edge 903 may join into a lateral edge 906 that is pointy or of a shortest length among four edges. The curved superior edge 905 and curved inferior edge 903 may join into a medial edge 904 that is also curved with a peak or plateau pointing outwardly from the fabric layer. One or more of the superior 905, inferior 903, and lateral 904 edges may be curved or flat. The edges may be curved such that the peak of the curve is pointing outward from the mesh. The sublay mesh may include a barrier 907 of an arbitrary shape. The barrier may be located below the horizontal centerline line 916, wherein the horizontal centerline is at 50% of mesh height. The barrier may be located substantially in a region close to the vertical centerline of the mesh, wherein the vertical centerline is at 50% of mesh width. The barrier may be located medial to the vertical centerline. The barrier may extend inferiorly from the horizontal centerline and may stop within about 1 cm of the inferior edge in order to allow the inferior edge to adhere to surrounding tissues. Such design of barrier may prevent mesh folding and/or mesh movement post-procedure. As nonlimiting examples, mesh may fold from anterior side toward the posterior side, from inferior edge toward the horizontal centerline, from lateral edge toward medial edge. The spermatic cord 911 and the genital nerve 912 may be positioned anterior (ventral) to the mesh anterior surface. The spermatic cord and the genital nerve may or may not overlap with each other, may come from an angle that is not substantially parallel to the mesh surface. The spermatic cord may be in contact with the exposed 1 cm edge of the mesh that lacks barrier. This minimal amount of adhesion will not contribute to the problems of chronic pain, testicular pain, and functional impairment. However, it will assure that the most inferior edge of the mesh is adhered down to tissue along the entirety of its edge. This adherence of the mesh edge reduces risk of mesh being free to fold up in the horizontal plane. Folding at the inferior edge of the mesh over the level of the spermatic cord is a known cause of hernia recurrence.

FIG. 9B shows the sublay mesh of FIG. 9A in a posterior view. There may be no barrier on the posterior side of the mesh 90. The spermatic cord and its contents (911, 912), after the mesh is properly implanted, may not directly contact the posterior side of the mesh as the sublay technique may serve as a blanket over the spermatic cord contents and the anterior side of the mesh may be analogous to the underside of a blanket. The spermatic cord content may or may not overlap with each other. The sublay mesh 90 may not have a keyhole and/or a slit.

The mesh 90 may not have a keyhole, which may be an intentional design of the male-specific sublay mesh. Keyholing of retroperitoneally placed mesh may have a greater chance of spermatic cord adhesion, erosion, and injury therefore; there may be less testicular pan, sexual dysfunction, infertility, or other mesh-caused health problem for male patients. The sublay mesh may only contact the spermatic cord and the genital nerve at its anterior side thus it is free of barrier on the posterior side. When viewed from the posterior side of the mesh, the spermatic cord and nerve are underneath the mesh.

FIG. 9C shows a flat or 3-dimensional sublay mesh specifically for usage in a male patient. The sublay mesh may be implanted to the right side of the midline of the patient in an anterior view. The sublay mesh 90 may have an arbitrary two-dimensional or 3-dimensional shape that is placed underneath the spermatic cord and hernia area. The sublay mesh may have one or more curved edges or may be flat on one or more of its edges. The sublay mesh may have a pre-shaped water-drop configuration, widest medially and tapered laterally. Alternatively, it may have a more rectangular shape that allows for the surgeon to tailor the mesh by cutting it to the desired shape. In the curved configuration, the superior edge 905 and inferior edge 903 may join into a lateral edge 906 that is pointy or of a shortest length among four edges. One or more of the superior 905, inferior 903, and lateral 904 edges may be curved or flat. The edges may be curved such that the peak of the curve is pointing outward from the mesh. The sublay mesh may include a barrier 907 of an arbitrary shape. The barrier may be located below the horizontal centerline line 916, wherein the horizontal centerline is at 50% of mesh height. The barrier may be located substantially in a region close to the vertical centerline of the mesh, wherein the vertical centerline is at 50% of mesh width. The barrier may be medial to the vertical centerline. The barrier may stop within about 1 cm of the inferior edge in order to allow the inferior edge to adhere down to surrounding tissues. Such design of barrier may prevent mesh folding and/or mesh movement post-procedure. As nonlimiting examples, mesh may fold from anterior side toward the posterior side, from inferior edge toward the horizontal centerline, from lateral edge toward medial edge.

The spermatic cord 911 and the genital nerve 912 may be positioned anterior (ventral) to the mesh anterior surface. The spermatic cord and the genital nerve may or may not overlap with each other, may come from an angle that is not substantially parallel to the mesh surface. The spermatic cord may be in contact with the exposed 1 cm edge of the mesh that lacks barrier.

The barrier 907 may have a shape that fans out inferiorly such that the width of the barrier increases gradually from its most superior portion of the barrier towards its most inferior portion. The barrier may have as non-limiting examples, a bell shape, a parabolic shape, a triangle shape, a finger nail shape. The barrier may be substantially symmetric about the vertical centerline at 50% of mesh width or may be shifted toward the medial edge. The narrowest width of the barrier may be sufficient to prevent direct contact of the spermatic cord and its contents and the genital nerve from the fabric layer at the level of the internal ring. The barrier may have an inverted U-shape with the arc being in close vicinity to the horizontal centerline. The barrier may extend substantially inferiorly but not obliquely or laterally. Shape and position of the barrier may optimize protection and anti-adhesion of the spermatic cord and its contents and/or genital nerve from the fabric layer. The shape and position of the barrier may maximize infiltration and adhesion of other tissues to the fabric layer.

FIG. 15 shows a mesh that may be used in male patients. The mesh 1500 may be a combination of an onlay mesh 1531 and a sublay mesh 1532 joined optionally by a hollow mesh tube 1533. The onlay mesh, including its size, shape, and/or function, may be similar to the onlay meshes 20, 30, 50, 60, 70, 80, previously described herein. Optionally, the onlay mesh may have one or more edges, 1503-1506. Each edge may be flat or curved. Each edge may be shaped or sized as previously described for onlay mesh edges. The mesh may include a keyhole 1507 whose function, size, shape, position, and/or other features that may be very similar to keyhole previously described, 209, 309, 709, 809. Alternatively, the mesh may include a keyhole 1507 that is inferior to the horizontal centerline 1516 and lateral to a vertical centerline of the onlay mesh 1517. The sublay mesh may be similar to sublay meshes 90 as previously described. The spermatic cord and its contents and/or the genitofemoral nerve may come into the keyhole from the anterior side of the onlay mesh at an angle that is oblique to a slit 1510 and exist between the posterior side of the onlay mesh 1531 and the anterior side of the sublay mesh 1532. The tube may have a length such that the critical structures 1511, 1512 are not constricted in the anterior to posterior direction by the onlay mesh and the sublay mesh. The mesh may include a barrier 1507, and 1534. The barrier 1507 on the onlay mesh may be any barrier that is previously described for male-specific onlay meshes. The barrier 1507 on the sublay mesh may be any barrier that is previously described for male-specific onlay meshes. Optionally, the barrier 1507 may cover the entire circumference of the keyhole with a rim of at least 0.5 cm. Alternatively, the barrier 1507 may cover only part of the circumference of the keyhole with a rim of at least 0.5 cm. The barrier 1507 on the onlay mesh may be located completely inferior to a horizontal centerline and medial to a vertical centerline of that onlay mesh as previously described. The barrier 1507 on the sublay mesh may be located completely inferior to a horizontal centerline and medial to a vertical centerline of that sublay mesh as previously described. The barrier 1507 may include an edge that overlaps substantially with a part of the circumference of a cross-section of the tube at the onlay mesh and at the sublay mesh. Such overlapping edges at the onlay and the sublay mesh may have different length (bottom panel). The barrier may also include a region 1534 that is on the tubular surface of the hollow tube 1533. To optimally protect the critical tissue 1511, 1512, this region may cover the region that the critical structures may contact when it comes through the keyhole 1509 and exit between the onlay and sublay mesh. Such region may also be limited to be substantially within an inferolateral quarter of the tubular surface of the tube to allow adhesion of the tube to other tissues. This barrier region 1534 may be less than 25% to 50% of entire tubular surface of the hollow tube. The tube may have an arbitrary cross-section that may or may not be identical at the location where it joins the onlay mesh or the sublay mesh. The barrier region 1534 may cover the entire length of the tube from the onlay mesh to the sublay mesh. The barrier 1534 may connect the barrier region on the sublay mesh on one end. The barrier 1534 may contact the projection on the posterior side from the anterior barrier 1507 on the onlay mesh on the other end. The barrier region 1534 may be inferior to horizontal centerlines 1516a, 1516b. The mesh 1500 may be advantageous over the single onlay mesh or single sublay mesh as it provides a sandwich-type repair of the hernia defect under low tension which ensures protection from both above or underneath the critical structures. Such low tension may be advantages especially during activities post implantation. The mesh may be more complicated to implant as compared to single onlay or sublay meshes.

In some embodiments, the fabric layer is not covered by a barrier in a region so that it allows tissue ingrowth onto the fabric layer. This region shall measure to be at least 75% of the anterior surface area, as the barrier should encompass no more than 25% of the mesh surface area.

For males, the mesh may have broad medial coverage and progressively tapering lateral coverage. In some embodiments, the mesh may have broad medial coverage and little to no tapering laterally. This may then be tailored by the surgeon as needed. The weight of the mesh may not be critical to its design, and all mesh weights, such as heavyweight (greater than 90 grams/square meter), medium weight (40-90 grams/square meter), lightweight (20-40 grams/square meter), and ultra-lightweight (under 20 gram/square meter) may be considered non-limiting options in design. The density and weave of the mesh content may determine these weights. The density of the mesh is the density combining the interstitial structure and hollow pores of the mesh. The density of the mesh may or may not include the applied barrier. The mesh density may reflect one or more of: thickness of mesh, weaving density, pore size, pore shape, material density of interstitial structure, and width and height of interstitial grid lines.

Areas of mesh overlap with the spermatic cord may be protected with a barrier. This may apply to all two-dimensional flat mesh as well as more complex three-dimensional mesh with inlay component. Since the mesh itself may be used as a patch, with or without a keyhole component, adherence to the spermatic cord itself is not critical to its function. It is more important that the mesh adhere to surrounding structure, such as muscle, fascia, periosteum, and prevent organs and fat from herniating under or through the mesh. Thus, the edges of the mesh, regardless of adjacent structures, may not have any barrier.

Gender-Specific Mesh for Women

The female-specific mesh may be configured to reduce chronic pain related to the mesh. The female-specific mesh may reduce pain related to the weight of the mesh, or pain related to foreign body inflammatory response cause by implantation of the mesh. The female-specific mesh may be configured to reduce activity-related pain and/or pain related to sexual activity, such as intercourse and orgasm. The female-specific mesh may be configured to reduce risk of hernia recurrence. The female-specific mesh may be configured to treat a femoral hernia or prevent a femoral hernia.

The female-specific mesh may be a flat onlay mesh. The flat onlay mesh is configured to be used for open inguinal hernia repair, for example using the Lichtensten onlay patch technique.

The flat onlay or sublay mesh may be cut or tailored by a medical professional. The flat onlay or sublay mesh may include a pore size of at least about 4 mm. Other smallest pore sizes of a female mesh may be about 2 mm, about 3 mm, about 3.5 mm, about 4.5 mm, about 5 mm, or about 2.5 mm.

In some embodiments, light-weight flat mesh, for non-limiting example, less than 40 gm/m$^2$, with 4 mm wide pores or interstices may be an appropriate mesh for women of normal to low body mass, for non-limiting example, less than about 30 kg/m$^2$. In some embodiments, heavier weight flat mesh, for non-limiting example, about 90 gm/m$^2$, about 4 mm wide pores or interstices may be used for women of higher body mass, for non-limiting example, no less than 30 kg/m$^2$. In some embodiments, the light-weight mesh helps to alleviate discomfort, pain, or functional impairment of the human body. In some embodiments, light-weight flat mesh, for non-limiting example, less than about 40 gm/m$^2$, with about 4 mm wide pores or interstices is used for men of normal to low body mass, for non-limiting example, less than about 30 kg/m$^2$.

For females, the mesh may have normal broad medial coverage and also a broad lateral coverage, to help conform to the flatter, broader, wider pelvis. This is significantly different than existing mesh design, which may be most appropriate for the male pelvic anatomy. To accommodate the anatomical differences in female as disclosed herein, for example, the wider, flatter, shallower pelvis in female, lateral half of the mesh is wider and not tapering as the male meshes to enable sufficient coverage and protection.

The round ligament, unlike the spermatic cord, may not pose major risk in postoperative pain. In fact, many surgeons, including most hernia specialists, urologists, and gynecologists, routinely transect the round ligament when performing an inguinal hernia repair. This has not been shown to have any adverse consequence to the female patient. However, it may allow for a flatter mesh placement, without need for keyhole or slit, and with lower risk of herniation of contents under or through the mesh at the site of overlap with the round ligament. As a result, there may be a lower hernia recurrence risk. The critical structures of a female patient may include a genitofemoral nerve, a genital nerve, and/or other nerves. The critical structures of a female may not include a round ligament.

The genitofemoral nerve may remain at risk for adherence to the mesh in hernia repair among females. Adhesion barrier along the path of the genitofemoral nerve posteriorly and the genital branch of the genitofemoral nerve anteriorly may help reduce this risk of chronic postoperative pain. Since the genital nerve may run obliquely to a horizontal centerline or a vertical centerline of a female mesh upon implantation. Such oblique position of the genital nerve may include the inferior-medial portion of the mesh, especially when the genital nerve moves due to activity or other motions post implantation. It is advantages to include a barrier that covers at least partly the oblique track of genital nerve upon mesh implantation, taking into consideration of it possible movements, to optimize protect while minimize the reduction in adhesion to other tissues.

Mesh weight (i.e., density) has been shown to be directly related to postoperative inflammation and thus postoperative acute and chronic pain patterns. In females, this correlation may be strongest, and so usage of lighter weight mesh products may improve outcomes in terms postoperative mesh-related pelvic pain. In rare circumstances, such as with the morbidly obese or women with multiple risk factors for hernia recurrence, heavier weight mesh may be necessary to reduce hernia recurrence risk.

In some embodiments, as can been seen in FIG. 1, the flat onlay mesh for female may not include a keyhole or a slit. The flat onlay mesh may only include a barrier on the posterior side but may not include a barrier on the anterior side (not shown).

Referring to FIG. 1, in a particular embodiment, a flat onlay mesh 10 for female patients is shown in a posterior view. The mesh may be implanted substantially to the right side of the midline of the patient. The mesh may have a substantially rectangular shape with an overall weave structure. The mesh may have four edges that are substantially straight 103, 104, 105, and 106, or may be curved. The overall mesh structure may include uniformed pores 101 separated by grid structures 102. In some cases, mesh braiding may be variable or non-existent. The width or length of the pore may be any number between 0 mm to 10 mm or more. In some cases, the mesh pore may be any two-dimensional or 3-dimensional shape. For nonlimiting examples, the pore may be square, rectangular, round, oval, triangle, hexagon, pentagon, diamond, fan, or a combination thereof. In some cases, the pore size may be variable across the mesh. The mesh 10 may include a barrier 107 superimposed on the posterior side of the mesh occupying about 50 percent of its length along the inferior edge 103 starting from the medial edge 104 of the mesh. The barrier 107 covers the fabric layer and/or pores 101 and grid structures 102 thereunderneath. The width of the barrier along the medial edge 104 is about 2 cm. In this embodiment, the barrier 107 is only applied on the posterior side of the mesh but not applied on the anterior side of the mesh. In some cases, the flat only mesh 10 is placed anterior to (ventral to) the hernia defect and/or muscle defects. The genital nerve 113 of the patient may travel along the posterior edge and inferior edge of the mesh. The barrier is intended to prevent the nerve from adhesion or erosion by the mesh. The mesh may be wider in the transverse direction than the longitudinal direction, such that the superior edge 105 and the inferior edge 103 are longer than the medial edge 104 and the lateral edge 106.

Figure 10A:
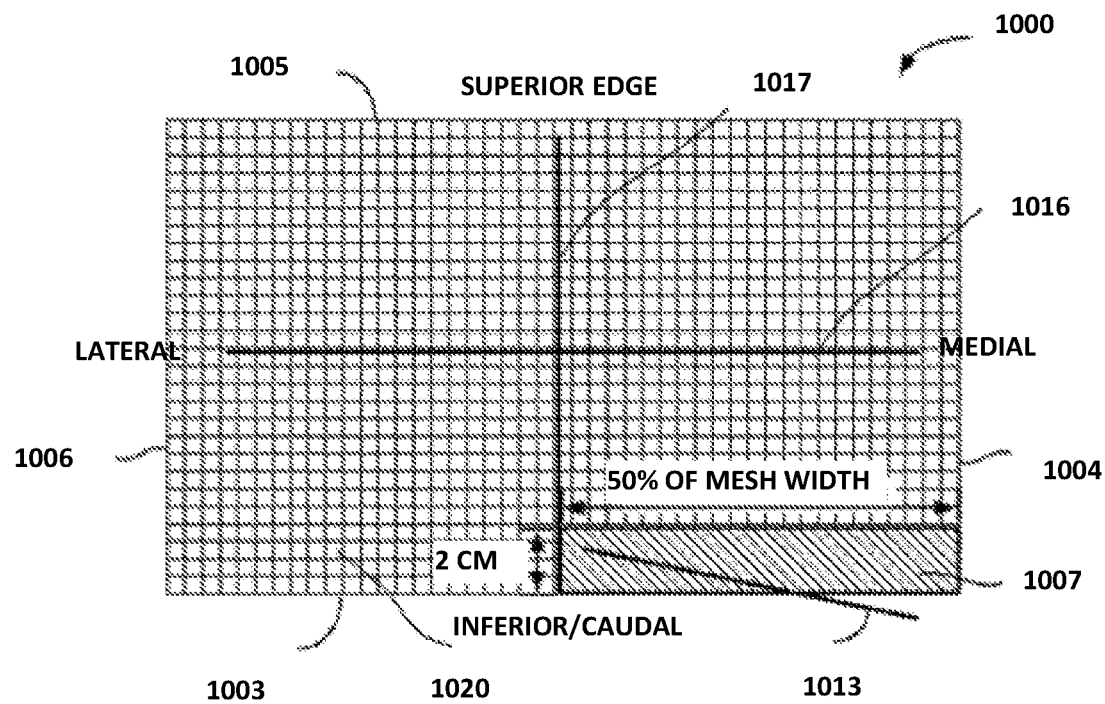
FIG. 10A shows another non-limiting example of a mesh for inguinal hernia repair in female patients described herein with anti-adhesive barrier viewing from the posterior side, in accordance with embodiments.
Figure 10B:
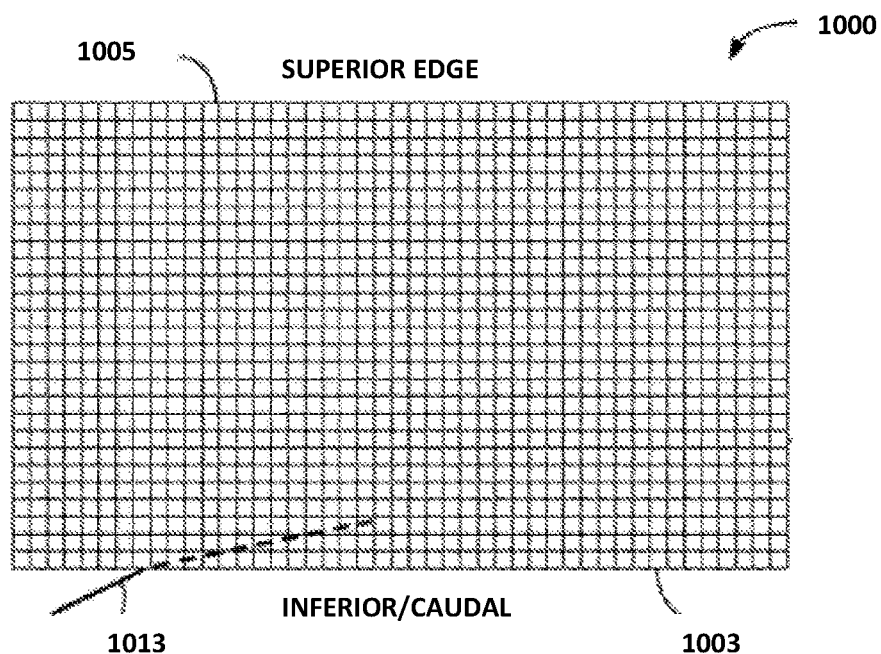
FIG. 10B shows an anterior view the mesh of FIG. 10A, in accordance with embodiments.

FIG. 10A shows a flat onlay mesh 1000 for female patients in a posterior view. The mesh may be implanted substantially to the left side of the midline of the patient. The mesh may have a substantially rectangular shape with an overall weave structure. The mesh may have four edges that are substantially straight 1003, 1004, 1005, and 1006, or they may be curved. The mesh 1000 may include a barrier 1007 superimposed on the posterior side of the mesh occupying about 50 percent of its length along the inferior edge 1003 starting from the medial edge 1004 of the mesh. The barrier 1007 covers pores and/or grid structures thereunderneath. The width of the barrier along the medial edge 1004 is about 2 cm. In this embodiment, the barrier 1007 is only applied on the posterior side of the mesh but not applied on the anterior side of the mesh. In some cases, the flat only mesh 1000 is placed anterior (ventral) to the hernia defect and/or muscle defects. FIG. 10B shows the anterior view of the mesh in FIG. 10A. The mesh may be wider in the transverse direction than the longitudinal direction such that the superior edge 1005 and the inferior edge 1003 are longer than the medial edge 1004 and the lateral edge 1006.

Figure 11A:
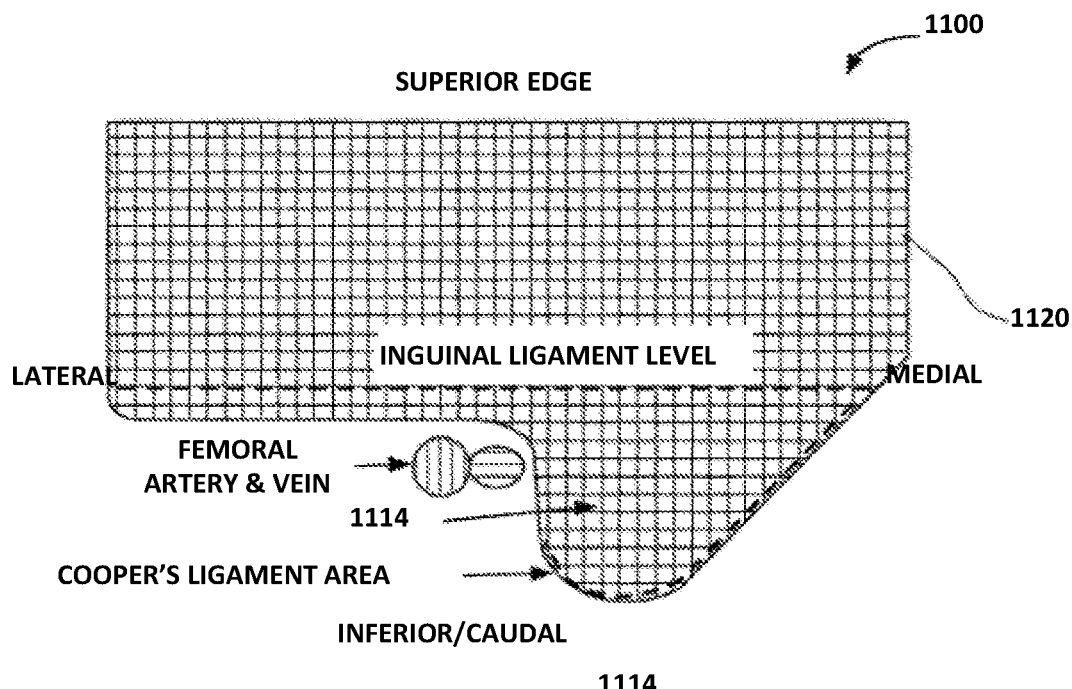
FIG. 11A shows another non-limiting example of a mesh for inguinal hernia repair in female patients described herein with anti-adhesive barrier viewing from the posterior side, in accordance with embodiments.
Figure 11B:
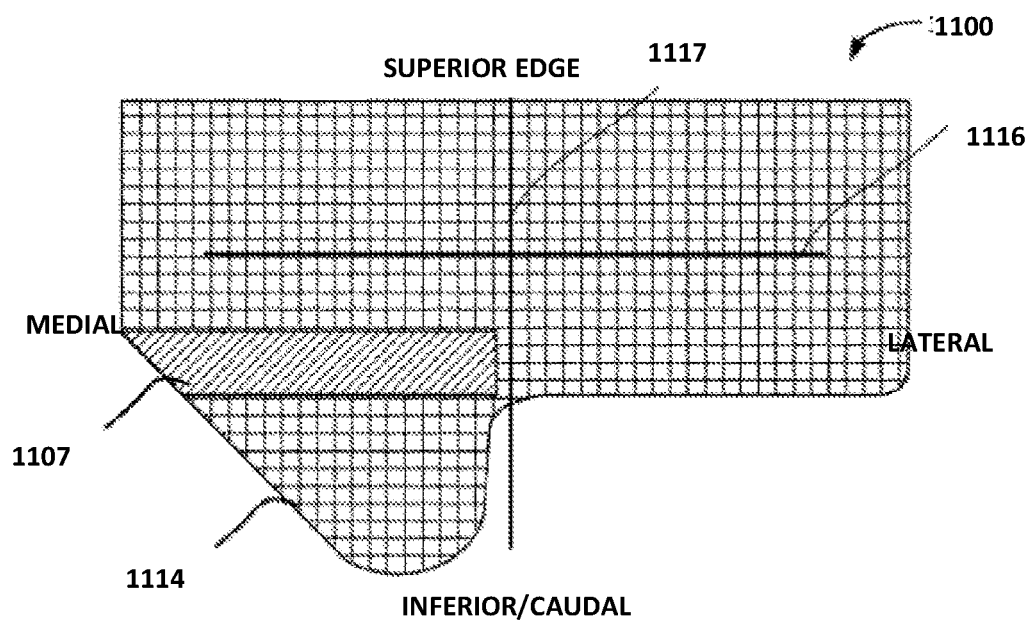
FIG. 11B shows an anterior view the mesh of FIG. 11A, in accordance with embodiments.

FIG. 11A shows a flat onlay mesh 1100 for female patients in a posterior view. The mesh may be implanted substantially to the left side of the midline of the patient. The mesh may have an irregular shape comprising a substantially rectangular shape and an irregular drape 1114 at the inferior edge of the mesh. The mesh may have four edges that are either substantially straight or curved. The mesh 1100 may extend inferiorly from the inguinal ligament level of the patient after it is properly implanted. The irregular drape 1114 may cover the femoral area of the patient and the inferior tip of the drape may be configured to allow attachment to the Cooper's ligament area of the patient. The drape may be located medial to the femoral artery and vein. The drape area of the mesh may not obstruct the femoral artery and vein. The mesh can be tailored further to assure this. FIG. 11B shows the anterior view of the mesh in FIG. 11A. The mesh may include a barrier 1107 on the anterior side of the mesh. The barrier may be located at the inferomedial edge of the substantially rectangular shape of the mesh. The mesh may be superiorly adjacent to the irregular drape 1114.

Figure 12A:
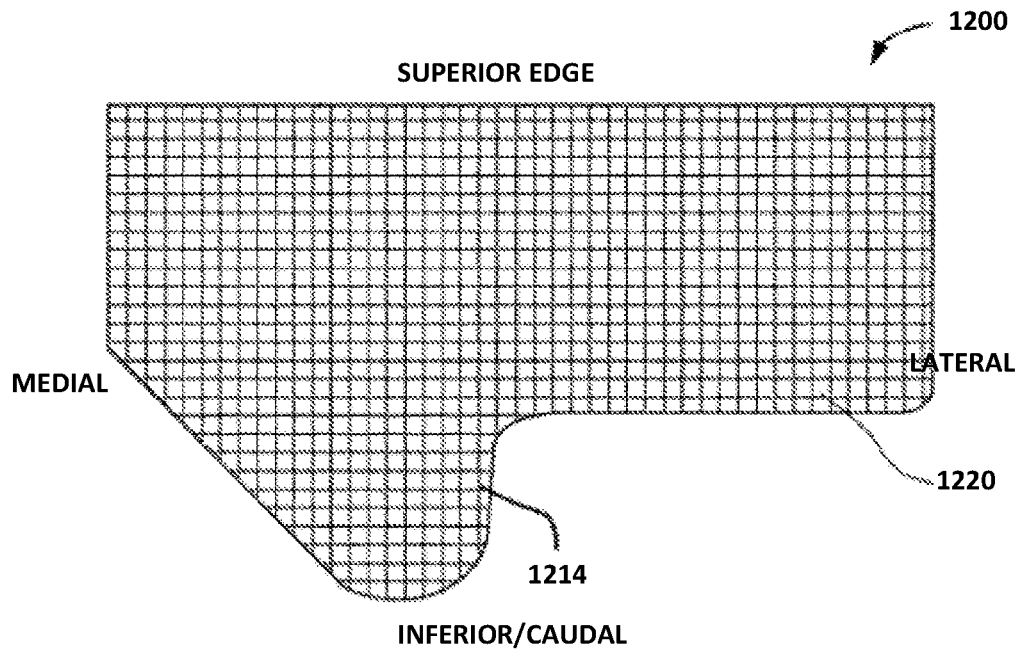
FIG. 12A shows another non-limiting example of a mesh for inguinal hernia repair in female patients described herein with anti-adhesive barrier viewing from the posterior side, in accordance with embodiments.
Figure 12B:
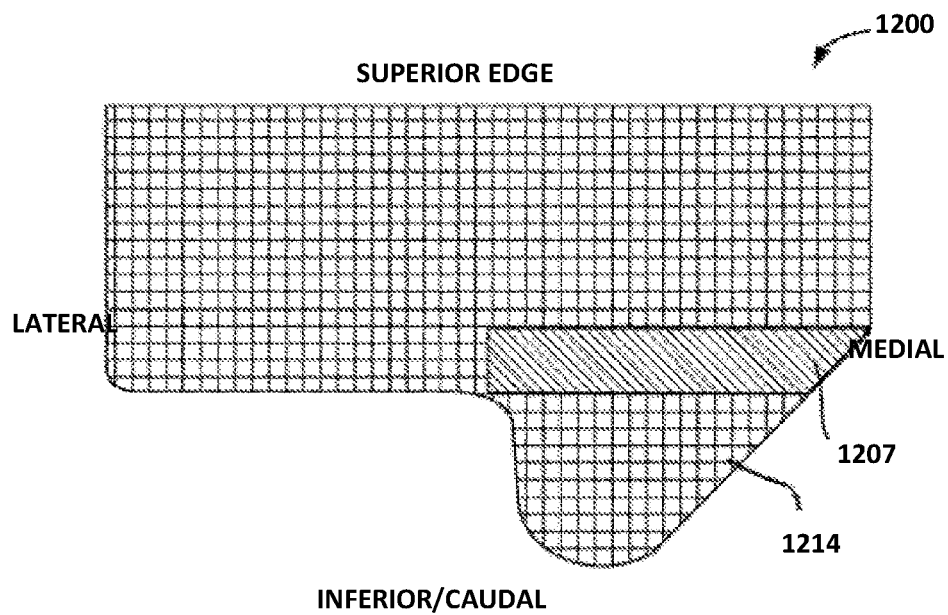
FIG. 12B shows an anterior view the mesh of FIG. 12A, in accordance with embodiments.

FIG. 12A shows a flat onlay mesh 1200 for female patients in a posterior view. The mesh may be implanted substantially to the right of the midline of the patient. The mesh may have an irregular shape comprising a substantially rectangular shape and an irregular drape 1214 at the inferior edge of the mesh. The mesh may have four edges that are either substantially straight or curved. The mesh 1200 may extend inferiorly from the inguinal ligament level of the patient after it is properly implanted. The irregular drape 1214 may cover the femoral area of the patient and the inferior tip of the drape may be configured to allow attachment to the Cooper's ligament area of the patient. The drape may be located medial to the femoral artery and vein. The drape area of the mesh may not obstruct the femoral artery and vein. The mesh may be further tailored to assure this non-obstruction of femoral artery and vein. FIG. 12B shows the anterior view of the mesh in FIG. 12A. The mesh may include a barrier 1207 on the anterior side of the mesh. The barrier may be located at the inferomedial edge of the substantially rectangular shape of the mesh. The mesh may be superiorly adjacent to the irregular drape 1214.

In some cases, the size of a flat onlay mesh 10, 1000, 1100, 1200 may be about 1 inch by about 4 inches, about 2 inch by about 4 inches, about 3 inch by about 6 inches, and/or about 4 inch by about 6 inches or greater. The shorter dimension may be along the vertical plane, and longer along its width in the transverse direction than in the longitudinal direction. In some cases, the length along the medial or lateral edge is about 0.5 inches to about 10 inches. In some cases, the width along the inferior or superior edge is about 0.5 inches to about 10 inches. In some cases, the pore may have a width or length of at least 3 mms. In some cases, the pore size of the mesh is at least 4 mms. For use in female patients, the flat onlay mesh does not include a keyhole structure. In some cases, in the absence of spermatic cord and its contents in females, the barrier protects the genital nerve branch of the genitofemoral nerve 113 in FIG. 1, from undesired adhesion to the mesh, and prevents one or more of them from injury due to adhesion or contact with the mesh. In some cases, no barrier is needed to protect the round ligament of a female subject. The nerve runs only directly facing the posterior side of the mesh when placed as an onlay.

Figure 4:
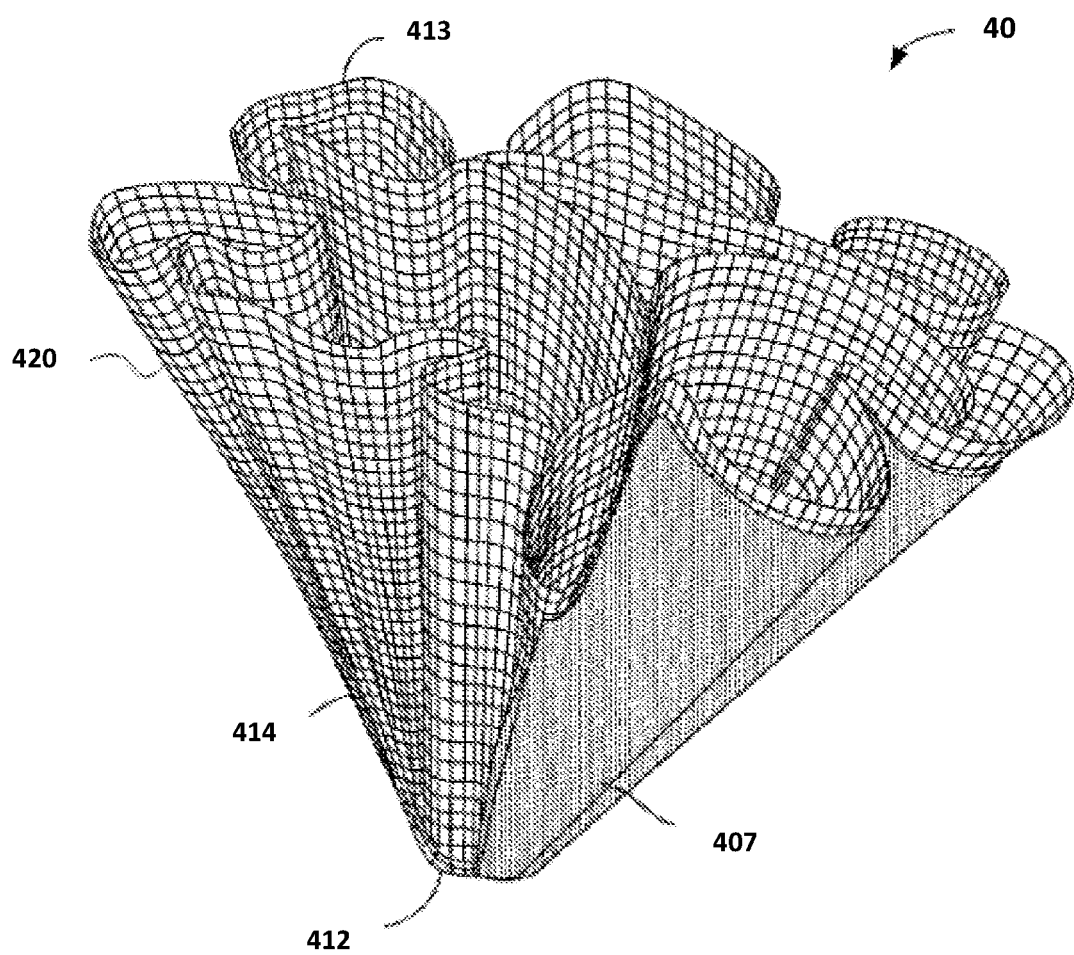
FIG. 4 shows a non-limiting example of a mesh for inlay inguinal hernia repair described herein with anti-adhesive barrier, in accordance with embodiments.

The mesh 10, 1000, 1100, 1200 may have at least two sides; a first side of the mesh may face posterior (dorsal) direction of a subject while the second side of the mesh may face anterior (ventral) side of a subject, or vice versa. The first side, the second side or both sides of the mesh may be flat, curved, bent, folded, uneven, or any other three-dimensional shape. As a nonlimiting example, the mesh may be folded into a mesh plug as shown in FIG. 4. The mesh may have a thickness extending from the first side to the second side of it.

The mesh 10, 1000, 1100, 1200 may include a layer or a sheet of fabric, fabrication, or the like. Such layer may have a grid pattern. The grid pattern may include interstitial pores 101 separated by grid structures 102. The grid pattern may include openings 101 separated by interlaced structures 102. The grid structure may be permeable or non-permeable to preselected element(s). The mesh pattern, the grid structure, and/or the pore size may be spatially uniform throughout the mesh. The mesh pattern, the grid structure, and/or the pore size may be spatially variable throughout the mesh. Such variable features to the mesh may provide variability in tissue adhesion, physical support, and/or ability to deform or reshape as the body moves. The variability may be in the shape, size, and/or dimension of pores and/or grid. Such layer may have a solid pattern. Such layer may include a solid pattern that may be permeable or non-permeable to preselected element(s). Such a layer may have a solid pattern in some spatial area of the mesh and a mesh pattern in the other spatial area of the mesh. The interstitial openings and an interlaced structure may be absent in a mesh. As non-limiting examples, the layer may include human-derived biologic tissue, animal-derived biologic tissue, a synthetic film or layer, a biologic film or layer, an absorbable layer, a non-absorbable layer, any other suitable material.

The mesh 10, 1000, 1100, 1200 may not have a passageway or a slit that can be configured to allow passage of a tube-like structure of the human body. The surgeon may choose to add a slit or keyhole to accommodate for the round ligament and/or genital nerve branch of the genitofemoral nerve. Such a passageway may restrict the natural movement and positioning of the genital nerve and, with risk for genital nerve compression (with pain at upper inner thigh and labia). The mesh may only include one layer of fabrication.

The mesh may include an optional drape, 1114, 1214 to treat or prevent femoral hernia, which is more commonly seen among women. The drape can be an inferior extension from the barrier 107, 1007, 1107, and 1207 on the mesh.

In some cases, the mesh 10, 1000, 1100, 1200 works as an onlay patch. The onlay mesh may be implanted over (anterior to) a critical anatomical structure, the spermatic cords and its contents, and/or nerves, such that the posterior side of the onlay mesh may face and/or contact the critical anatomical structure while the anterior side of the onlay mesh may not face and/or not directly contact the critical anatomical structure.

The female-specific onlay mesh 10, 1000, 1100, 1200 may be precut. The precut onlay mesh 1100, 1200 may be configured for usage for open inguinal hernia repair. The precut onlay mesh may be configured to address high incidence of femoral hernias among women. Such precut onlay mesh may be used for men with femoral hernias, too. The precut onlay mesh may include an extra mesh area 1114, 1214, extending below the inguinal ligament to at least partly cover the femoral space. The edge of the extra mesh area may be attached to Cooper's ligament.

Alternatively, the precut onlay mesh 1100, 1200 may be used for male patients with femoral hernias. Though femoral hernias are rare among men and prophylaxis is not standard, the use of mesh 1100 or 1200 configuration can be used to treat femoral hernias in males. The placement of the mesh may be similar as with females, however, a slit and keyhole will be necessary to accommodate for the spermatic cord and its contents. This can be tailored by the surgeon.

Figure 13A:
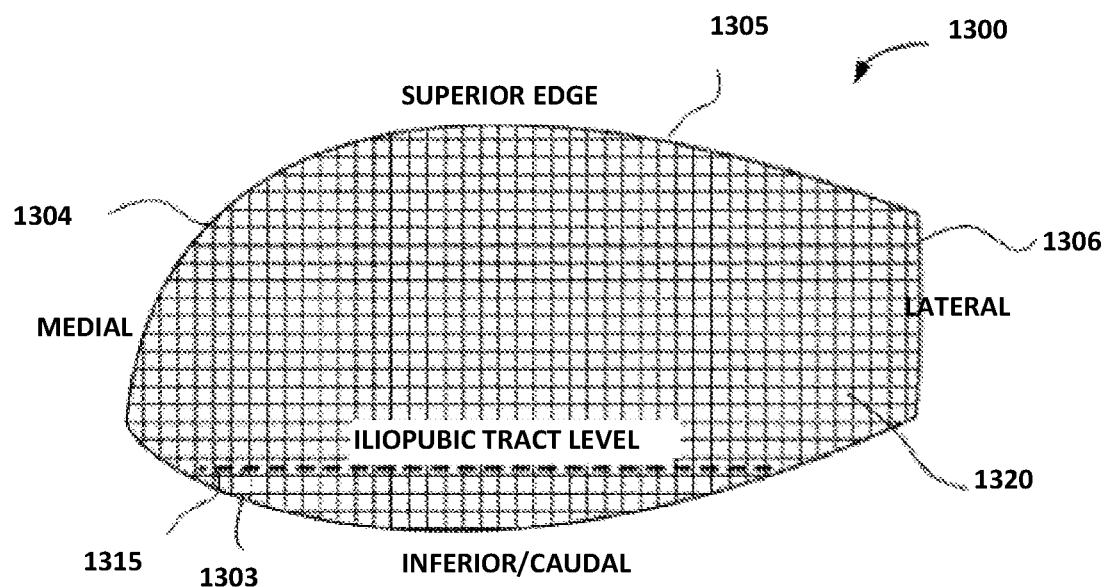
FIG. 13A shows another non-limiting example of a mesh for inguinal hernia repair in female patients described herein viewing from the anterior/ventral side, in accordance with embodiments.
Figure 13B:
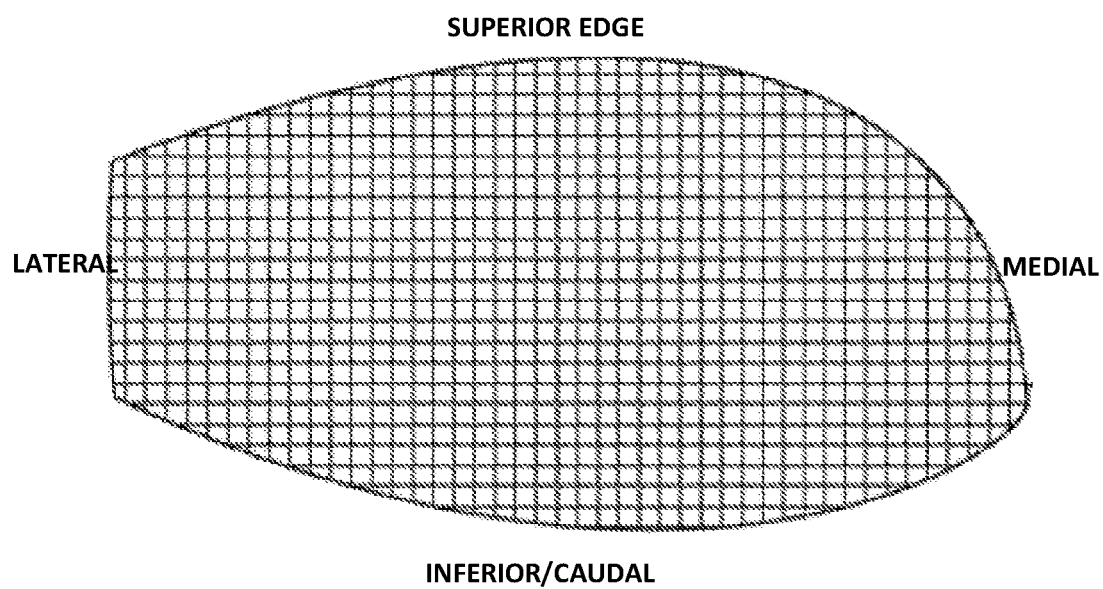
FIG. 13B shows a posterior view the mesh of FIG. 13A, in accordance with embodiments.

FIG. 13A shows a flat or 3-dimensional sublay mesh 1300 for female patients that may be implanted substantially to the left side of the midline of the patient in an anterior view, or, optionally, a flat or 3-dimensional sublay mesh 1300 for female patients that may be implanted substantially to the right side of the midline of the patient when viewed posteriorly. The mesh may have an irregular shape. The mesh may have four edges that are either substantially straight or curved. The mesh may be wider laterally such that the superior edge 1305 and the inferior edge 1303 are wider than the length of the medial edge 1304 and the lateral edge 1306. The lateral edge may be flat and not as tapered as the male specific mesh. This provides for better wide coverage of the wider, flatter, shallower female pelvis, which will improve rates of hernia recurrence. The mesh 1300 may extend significantly inferior to the iliopubic tract level of the patient after it is properly implanted. The mesh may not have a barrier on its anterior or posterior side. FIG. 13B shows the posterior view of the left side mesh in FIG. 13A or optionally, the anterior view of the right side mesh in FIG. 13A. The mesh may not include a barrier on the anterior or posterior side of the mesh.

Figure 14A:
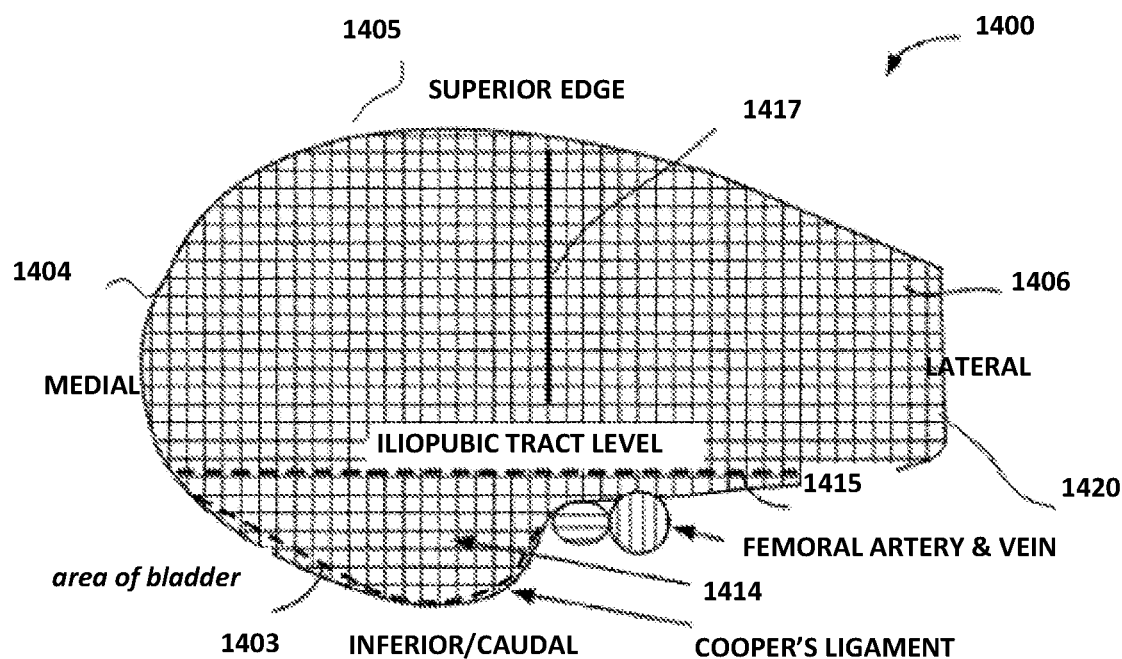
FIG. 14A shows another non-limiting example of a mesh for inguinal hernia repair in female patients described herein viewing from the anterior/ventral side, in accordance with embodiments.
Figure 14B:
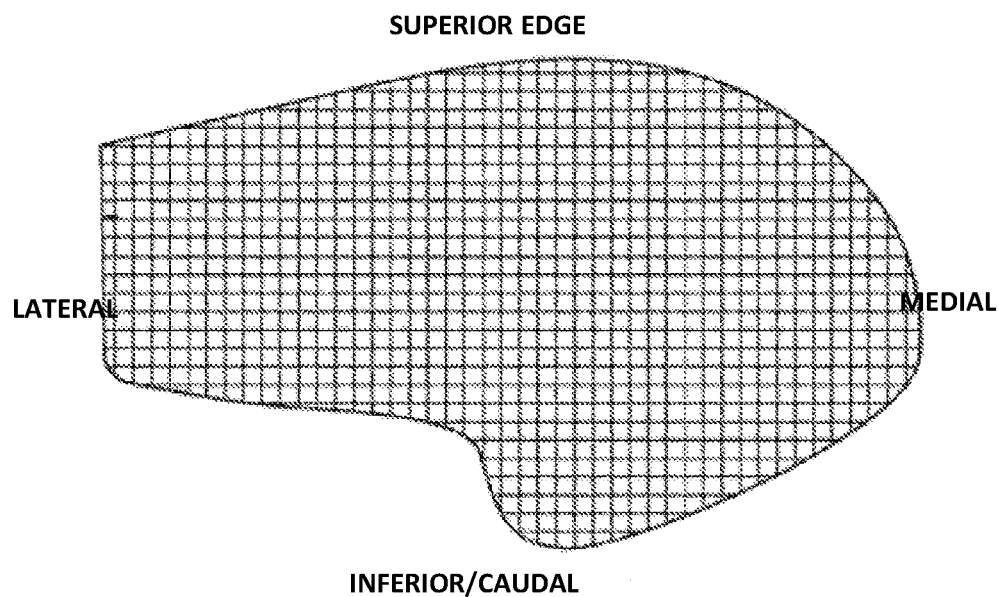
FIG. 14B shows a posterior view of the mesh of FIG. 14A, in accordance with embodiments.

FIG. 14A shows a flat or 3-dimensional sublay mesh 1400 for female patients that may be implanted substantially to the left side of the midline of the patient in an anterior view, or, optionally, a flat or 3-dimensional sublay mesh 1400 for female patients that may be implanted substantially to the right side of the midline of the patient when viewed posteriorly. The mesh may have an irregular shape. The mesh may have four edges that are either substantially straight or curved. The mesh may be wider laterally such that the superior edge 1405 and the inferior edge 1403 are wider than the length medial edge 1404 and the lateral edge 1406. This configuration may provide for better wide coverage for the wider, flatter, and shallower female pelvis as compared to males, which may improve rates of hernia recurrence. The lateral edge may be flat. The mesh 1400 may extend significantly inferior to the iliopubic tract level of the patient after it is properly implanted. The mesh may not have a barrier on its anterior side or posterior side, or both. The mesh may include an optional drape, 1414. The drape may be located medial to the femoral artery and vein. The drape area of the mesh may not obstruct the femoral artery and vein. The mesh may be further tailored to assure this non-obstruction. The drape may significantly extend inferior to the iliopubic tract level after the mesh is properly implanted. The drape may protect the femoral space. The most inferior part of the drape may allow attachment of the mesh to the Copper's ligament that ensures the mesh's proper positioning after implantation. The drape may not obstruct the femoral artery and vein. FIG. 14B shows the anterior view of the left side mesh in FIG. 14A or optionally, the anterior view of the right side mesh in FIG. 14A. The mesh may not include a barrier on the posterior side of the mesh.

In a female patient, a sublay mesh may not have any barrier either to the anterior or to the posterior side of the mesh. The female-specific mesh may be a sublay mesh configured to be used for laparoscopic inguinal hernia repair, robotic-assisted repair, and/or open retromuscular mesh placement. The female-specific sublay mesh may be wide enough laterally to accommodate for wide and shallow female pelvis. The female-specific sublay mesh may not encroach on the bladder region after proper implantation into the patient.

To accommodate the anatomical differences in female as disclosed herein, for example, the wider, flatter, shallower pelvis in female, lateral half of the sublay mesh 1300, 1400 (lateral to a vertical centerline) is wider and not tapering as the male sublay meshes 90 to enable sufficient coverage and protection in female post implantation.

The female-specific mesh, either onlay or sublay mesh, may have left-side or right-side variations (FIGS. 1, 10-14) depending where the mesh is implanted relative to the medial line of the patient. Left-sided mesh or right-sided mesh may be selected to provide optimal repair coverage for the respective inguinal hernia in different patients. Such left-side and right-sided variation accommodates for differences in inguinal hernia locations and repair. It assures that the barriers that are applied appropriately match the mirrored anatomy of the left and right inguinal region. This allows for maximization of exposed mesh to areas that require adhesion, such as the muscle, fascia, and periosteum, which will improve outcomes, such as lower recurrence rates for hernia, while at the same time will minimize adhesion of mesh to critical structures such as genital nerve in females.

General Meshes

In some cases, the mesh may not be a flat mesh but a three-dimensional mesh, sometimes referred to as a plug, for inlay implantation. This may be implanted into the hernia defect to effectively plug the hole in the muscle, fascia, and/or periosteum. This mesh plug may be appropriate for both male and female hernias. Referring to FIG. 4, in a particular embodiment, a mesh 40 for inlay placement is shown. The mesh plug may have a three-dimensional shape suitable for necessary reshaping (as nonlimiting examples, curving, bending, folding, or the like), so it may change its shape in three-dimension during or after placement procedure to accommodate for the hernia defect size and shape. The mesh plug 40 may be similar to non-limiting examples: a folded umbrella, a shuttlecock, a sphere, ball, ovoid shape, or other 3-dimensional space-occupying forms. The mesh plug 40 may have an anterior (ventral) edge 413 with foldings similar to the rim of a collapsed umbrella without the ribs. The mesh plug 40 may have posterior (dorsal) edge 412 wherein the mesh structural is similar to the tip of a folded umbrella without hub, tip or ribs. The barrier 407 may be applied from the posterior edge 412 and extends radially toward the anterior edge 413 of the mesh plug. The barrier 407 is optionally applied to about 50% of the outer circumference of the mesh plug 40. The surgeon may position the mesh plug to allow the barrier to come in contact with the critical structures, such as genital nerve in males and females and/or spermatic cord in males. As standard, the spermatic cord and its contents are placed lateral to the mesh plug in an indirect inguinal hernia repair, and so the plug would be positioned with the barrier 407 facing laterally. The barrier 407 may stop at about 1 cm away from the anterior edge of the mesh plug 40.

In some cases, the barrier is superimposed on a portion or the entirety of the outer wall of the mesh plug 40. The portion is about 1% to about 25%. In some cases, the barrier is applied to a portion that starts from the posterior (dorsal) edge (as a nonlimiting example, the posterior tip at the bottom when unextended as in FIG. 4) of the mesh and extends in any suitable shape that may prevent undesired tissue adhesion or damages to the patient. In some cases, the barrier is pre-applied before mesh placement. In some cases, the barrier may be modified before mesh placement by medical professionals to meet specific need(s) of the procedure/patient. In some cases, the barrier may be modified during or after mesh placement by the surgeon to achieve optimal effect. In some cases, modification of the barrier may include any changes to preexisting barrier or the mesh structure to which it attaches. Non-limiting examples change the area of barrier coverage on the mesh, apply or increase barrier coverage to the mesh, reduce or remove barrier coverage to the mesh, and/or change mechanical, thermal, chemical, or biological properties of the barrier. In further cases, barrier coverage includes the size, shape of coverage area and the position of coverage on the mesh.

In some cases, the barrier 207, 307, 507, 607, 707, and 807 may be oblique to a horizontal centerline and a vertical centerline of the mesh 20, 30, 50, 60, 70, and 80. A barrier edge starting from the most superior tip of the barrier and medial to the keyhole 209, 309, 709, and 809 may be oblique to a horizontal centerline and a vertical centerline of the mesh. The oblique location and the fan-out shape of the barrier may be optimal to protect the critical structures 511, 512, 711, and 712, from directly contacting the fabric layer thus prevent undesired adhesion thereto. Since the critical structures may naturally come into the keyhole in an oblique direction upon implantation and may move to a greater extend as its goes further away from the keyhole on the anterior side, such oblique location and the fan-out shape may provide optimal protection while allowing sufficient and optimal tissue adhesion in other uncovered area of the fabric layer. Similarly, as compared to a centered keyhole at 50% of mesh height 209, 309, an off-centered keyhole 709, 809 inferior to the horizontal centerline may decrease the barrier size (when the barrier covers at least a portion of the circumference of the keyhole) while still may effectively protect the critical structures. Additionally, a decrease in barrier size may allow an increase in increase in the total area of uncovered fabric layer on at least one side and thus may elevate desired tissue adhesion to other part of the uncovered fabric layer.

Fabric Layers

The meshes 10, 20, 30, 40, 50, 60, 70, 80, 90, 1000, 1100, 1200, 1300, 1400 and methods disclosed herein may include at least one fabric layer 120, 220, 320, 420, 520, 620, 720, 820, 920, 1020, 1120, 1220, 1320, and 1420. The meshes as disclosed herein may only comprise a single fabric layer. The single fabric layer of a 2-dimensional mesh may comprise a surface area on one side of the fabric layer. The one side may be an anterior side, or a posterior side. The surface area on the anterior side and the surface area on the posterior side may be identical. The single fabric layer of a 3-dimensional mesh may comprise a surface are on multiple sides of the fabric layer. The sides may be an anterior, posterior, medial, and/or lateral side.

The surface area of the fabric layer may be the maximal area restricted by the edges of the fabric layer. The single fabric layer may have variation in its weave pattern, pore size, weight, density, and/or other physical features. The fabric layer may be adhesive to surrounding tissues. The fabric layer may be selectively anti-adhesive to spermatic cords, contents and/or critical nerves in the area. The fabric layer may be flat, folded, curved, or other 3-dimensional shape. The flat fabric layer may be folded, curved or bent under force. The flat fabric layer may be resiliently curved or bent. The fabric layer may be resiliently reshaped to different degrees from a flat fabric layer to accommodate the anatomy of different patients. The fabric layer may have a pre-determined resistance to reshaping in certain directions in order to hold the herniated tissue back from bulging.

The fabric layer 120, 220, 320, 420, 520, 620, 720, 820, 920, 1020, 1120, 1220, 1320, 1420, and 1520 may include a region that is barrier-free. The barrier-free region may include a region that superior to the horizontal centerline 516, 616, 716, 816, 916, and 1016. The barrier-free region may include a region that is lateral to the vertical centerline 517, 617, 717, 817, 917, and 1017. The barrier-free region may include a region that is superior to the horizontal centerline and medial to the vertical centerline. The barrier-free region may include a region that is a fin extending inferiorly from the iliopubic tract level. The barrier-free region may be a rim of about 0.8 to about 1.2 cm from an inferior edge of the fabric layer. The barrier-free region may be a rim of about 0.8 to about 1.2 cm from an anterior edge of a mesh plug. The barrier-free region in male-specific meshes may be greater than 75% of the surface area on the anterior side or the posterior side of the fabric layer. The barrier-free region in female-specific meshes may be greater than 85% on the anterior side or the posterior side of the fabric layer.

The fabric layer 120, 220, 320, 420, 520, 620, 720, 820, 920, 1020, 1120, 1220, 1320, 1420 and 1520 may include a grid, a braid, a weave, an interlaced structure, or the like that defines a plurality of interstitial pores 101, 201, 301. The pores may have a maximal dimension on the surface area that. the maximal dimension being a width, a length, a diameter, a long axis, or a diagonal. The maximal dimension may be no less than 5 mm, 4 mm, 3 mm, 2 mm, or 1 mm. Alternatively, the fabric layer may be sheet without any visible weave or any visible pores to naked eyes. The fabric layer may allow tissue adhesion to the mesh with tissue that is directly contacting one side or both side of the fabric layer. Such tissue adhesion may be nonselective. The grid, braid, weave of the fabric layer may enable tailoring of a keyhole and a slit to accommodate critical structures of the male or female patients without disruption or damage to the rest of the fabric layer and its physical properties.

The meshes 10, 20, 30, 40, 50, 60, 70, 80, 90, 1000, 1100, 1200, 1300, and 1400 as disclosed herein may not comprise a second fabric layer that is not anti-adhesive, or not functionally equivalent to an anti-adhesive barrier. The mesh as disclosed herein may not comprise a second fabric layer that is in direction contact or in close proximity to the first fabric layer. The close proximity may include a shortest distance between the two layers of less than 1mm. A second fabric layer may add additional weight and density to the mesh. This translates into increase stiffness, less compliance, which may significantly increase chronic pain and limitations in range of motion in the inguinal pelvic region. The second fabric layer may exert additional requirements on attachment to the first fabric layer that can hold the two layers together at least in some regions. Such additional attachment may increase the risk of mesh failing due to the failure of the additional attachment. The second fabric layer and its attachment to the first fabric layer may cause possible problems when the fabric layer is shaped or customized by a medical professional. The second fabric layer and its attachment to the first fabric layer may decrease the desired tissue adhesion to the mesh. It may demand mounting or adhesion between the two layers that may present additional manufacturing procedures, costs, and possible failure due to partial or complete loss of adhesion between the two layers. It will also increase the risk of infection, as bacteria can be harbored within the two layers of fabric.

The fabric layer 120, 220, 320, 420, 520, 620, 720, 820, 920, 1020, 1120, 1220, 1320, and 1420 may include a horizontal centerline. In some cases, the horizontal centerline is at exactly 50% of mesh height, the mesh height being in the superior-to-inferior direction, or the longitudinal direction of the mesh or of the patient upon implantation. Alternatively, the horizontal centerline may be at about 50% of mesh height, the mesh height being in the superior-to-inferior direction, or the longitudinal direction. The fabric layer 120, 220, 320, 420, 520, 620, 720, 820, 920, 1020, 1120, 1220, 1320, and 1420 may include a vertical centerline. In some cases, the vertical centerline is at exactly 50% of mesh width, the mesh height being in the medial-to-lateral direction, or the transverse direction of the mesh or of the patient upon implantation. Alternatively, the vertical centerline may be at about 50% of mesh width, the mesh width being in the medial-to-lateral direction, or the transverse direction.

The fabric layer 120, 220, 320, 420, 520, 620, 720, 820, 920, 1020, 1120, 1220, 1320, and 1420 may include an inferomedial region, quarter, corner, or edge. The inferomedial quarter may be the quadric of the surface area touching the inferior and medial edges of the fabric layer. Similarly, the inferolateral region may be the quadric touching the inferior and lateral edges of the fabric layer. A quadric, as described herein, may start from the tip point at exactly 50% mesh height and 50% mesh width and may fan out in an about 90-degree angle toward two adjacent edges of the surface area of the fabric layer. The two edges of the quadric starting from the tip point of the quadric may end when each edge touches one of two adjacent edges of the fabric layer. In further cases, the quadric may be bounded by its two edges at the midpoints of two adjacent edges of the fabric layer. The inferomedial corner may be a portion of the quadric touching the inferior and medial edges of the fabric layer. The inferolateral corner may be a portion of the quadric touching the inferior and lateral edges of the fabric layer.

The mesh height may be the maximal distance between a superior edge and an inferior edge in the longitudinal direction. The mesh width may be the maximal distance between a medial edge and a lateral edge in the transverse direction.

In some cases, the meshes as disclosed herein may include a fin. In some cases, a fin as disclosed herein may be added to the meshes as disclosed herein either during manufacturing or by a surgeon. If needed, the new mesh combining a mesh as disclosed herein and a fin as disclosed herein may be tailored to properly fit into various patients. As a nonlimiting example, a fin may be included in an onlay female-specific mesh 1114, 1214, or a sublay female-specific mesh 1414. Alternatively, a fin with similar function, shape, and/or size as disclosed in FIGS. 11, 12, and 14 may be added to any male or female meshes as disclosed herein. Such a mesh with added fin may be tailored and implanted such that the fin may be in similar positions of the male or female patient relative to a Cooper's ligament area, a femoral space, a femoral artery, a femoral vein, or a combination thereof upon implantation. As a nonlimiting example, a fin may be added to male sublay mesh 90 or male onlay mesh 70. With an added fin, the barrier may stay on the anterior side for onlay meshes. With an added fin, the barrier may be on the posterior side for sublay meshes. Alternatively, with an added fin, the barrier may be on the anterior side for sublay meshes. In some cases, without a fin, the barrier as disclosed herein may be on the posterior side for onlay female meshes. With an added fin, the barrier as disclosed herein may need to be on the anterior side for onlay female meshes. If the mesh without a fin has no barrier, addition of the fin to the mesh does not change that.

Barriers

The devices and methods disclosed herein may comprise a barrier (also called anti-adhesive barrier herein) or a method of applying a barrier so that the subject's critical structures in contact with the barrier, for non-limiting example, such as (but not limited to) genital nerve in males and females and/or spermatic cord in males, is protected from undesired inflammatory responses caused by the proper implantation of the mesh at least for a pre-determined period of time, for non-limiting example, during the initial inflammatory healing phase after implantation. The barrier protects the critical structures from undesired adhesions to the mesh that might cause tissue damages, discomfort, pain, functional impairment, or infertility. The barrier and methods of applying the barrier described herein do not inhibit or affect the desired tissue adhesion or ingrowth onto the mesh where the barrier is not applied—whether on the same side of the mesh or on the opposite side of mesh. The barrier uses one or more synthetic or biological materials that ensure the protection of the nerve and/or spermatic cord especially during the initial phase of inflammation that typically occurs soon after the mesh implantation. The barrier provides this protection for a pre-determined period of time, at least, for example at least until the initial inflammation after implantation subsides by at least about 40%, at least about 50%, at least about 60%, at least about 75%, at least about 80%, at least about 85%, at least about 90%, at least about 95%, from about 50% to about 100%, from about 50% to about 90%, from about 70% to about 90%, from about 75% to about 95%, from about 75% to about 100%, or about 100%.

In some embodiments, the barrier 107, 207, 208, 307, 308, 407, 507, 607, 707, 708, 807, 808, 907, 1007, 1107, and 1207 is used to prevent or minimize inflammatory response to the mesh implantation. In some embodiments, the barrier is used to prevent or minimize adhesion or attachment of critical structures to the fabric layer of the implantable mesh when the structures make contact with the implantable mesh. In some embodiments, the barrier protects the genital nerve in males and females and/or spermatic cord in males from exposure to the synthetic materials of the mesh while the mesh is properly implanted. In some embodiments, the barrier protects the genital nerve in males and females and/or spermatic cord in males from attachment to the fabric layer as a result of tissue ingrowth or infiltration to the fabric layer. In some embodiments, the critical structures may include one or more of the following: a spermatic cord, a vas deferens, a testicular vessel, a genitofemoral nerve, and a genital branch of the genitofemoral nerve.

In some embodiments, the barrier 107, 207, 208, 307, 308, 407, 507, 607, 707, 708, 807, 808, 907, 1007, 1107, and 1207 is not permanent. In some embodiments, the barrier lasts for about a pre-determined period time. In some embodiments, the barrier is configured to optimally minimize the inflammatory reaction to the mesh, especially to the fabric layer, in the initial phase after implantation of the mesh. In some embodiments, this initial phase lasts from 4 days to about 8 months. In some embodiments, the barrier prevents the massive inflammatory reaction that occurs at the initial implantation of the synthetic mesh from transferring onto the genital nerve in males and females and/or spermatic cord in males. In some embodiments, the inflammatory reaction is caused by contact to a part of the mesh or insertion of the mesh. In some embodiments, the barrier is absorbed or dissolved by the human body after a time period of about 5 days to about 6 months. In some embodiments, the barrier is absorbed or dissolved by the human body after a time period of about 1 week to about 6 weeks. In some embodiments, the barrier is absorbed or dissolved after a certain period of time to facilitate tissue ingrowth onto the fabric layer of the mesh. In some embodiments, the barrier is absorbed or dissolved to expose the mesh that used to be covered underneath the barrier to the surrounding tissue, thereby maximizing the mesh strength and value. In some embodiments, the barrier may be permanent, thereby maximizing the protection effect of the barrier on the critical structures and minimizes the unwanted adhesion of critical structures that may cause physiological problems of the patient. In some embodiments, the barrier may be a part of the fabric layer and but with physical and/or biological differences to the rest of the fabric layer. The differences include the ability to allow tissue adhesion to the fabric layer/barrier that is in direct contact with.

In some embodiments, the barrier 107, 207, 208, 307, 308, 407, 507, 607, 707, 708, 807, 808, 907, 1007, 1107, and 1207 is applied onto at least or only one side of the fabric layer. In some embodiments, the barrier is applied on at least or only one side of the fabric layer via non-limiting examples of stitching, sewing, weaving, gluing, spraying, or other manufacturing methods for attachment. In some embodiments, the attachment means, for example, the gluing or the sewn-in material, is also absorbable or dissolvable by the human body. In some embodiments, it is permanent. In some embodiments, the additional material that is used to attach the barrier to the fabric layer is also absorbed or dissolved in a predetermined period of time. In some embodiments, the additional material is used to stitch, sew, glue, spray, or attach the barrier to one side of the fabric layer.

In some cases, the barrier 107, 207, 208, 307, 308, 407, 507, 607, 707, 708, 807, 808, 907, 1007, 1107, and 1207 may be a coating/processing on the fabric layer that is anti-adhesive. Alternatively, the barrier may be an overlay of a second fabric layer that is non-adhesive, such as a biologic tissue over the fabric layer. Alternatively, the barrier may be a totally separate weave of mesh on top and/or beneath the fabric layer which renders it absent or low in adhesions.

In some embodiments, the barrier 107, 207, 208, 307, 308, 407, 507, 607, 707, 708, 807, 808, 907, 1007, 1107, and 1207 is pre-applied to the mesh before sterile packaging. In some embodiments, the barrier is tailored by the surgeon or health professional before implantation after the sterile packaging has been opened. In some embodiments, the barrier is applied on-site of surgery after the sterile packaging has been opened.

In some embodiments, the mesh disclosed herein includes at least two different barriers. In some embodiments, the mesh is a hybrid mesh, and the first barrier is a biological barrier or an absorbable or dissolvable barrier. In some embodiments, the mesh is a hybrid mesh, and the second barrier is a biological or synthetic barrier that is integrated or placed on the synthetic fabric layer of the mesh.

In some embodiments, the barrier 107, 207, 208, 307, 308, 407, 507, 607, 707, 708, 807, 808, 907, 1007, 1107, and 1207 as disclosed herein includes one or more selected from a variety of anti-adhesive barriers that help reduce the adhesion of the mesh onto critical structures. Such barriers include but are not limited to various cellulose-derived products, for nonlimiting examples, icodextrin, collagen, poliglecaprone 25, omega-3 fatty acids, polytetrafluoroethylene, peritoneum, and various other tissue allografts and xenografts. In some cases, these barriers as disclosed herein come in forms of liquids, gels, powders, sheets, or other possible forms. In some cases, the length of time in which the barrier has full effect is variable. In some embodiments the barrier is made of at least one biological material. In some embodiments, the barrier is a biologic tissue, for example, a human or xenogenic tissue, a biological product, a suture, for example, poliglecaprone 25, or an anti-inflammatory product for example, a product normally used for cardiac stents. In some cases, at least 1 week of barrier in effect is necessary. In some cases, preferably 3 weeks of barrier minimum, as that is the time during which maximal inflammation ensues after mesh implantation. In some cases, placement of a barrier as disclosed herein prevents adhesion of critical anatomy to the mesh by limiting mesh adhesion to the areas where there are no critical structures.

The devices and methods disclosed herein comprise a barrier or a method of applying a barrier in order to minimize adherence of the mesh to critical structures without adversely affecting the adherence of the mesh to intended structures, such as muscle, fascia, and/or periosteum. Thus, the clinical goal is to reduce postoperative chronic pain, improve quality of life, and lower infertility risks without compromising the hernia repair and without adversely affecting the success rate of the hernia repair as it relates to recurrence.

In some embodiments, a barrier of the device protects the critical structures that it contacts from adhesion to the mesh and/or tissue ingrowth into the mesh when the mesh is properly implanted. In some embodiments, the barrier and methods of applying the barrier disclosed herein are applicable to any existing mesh or any other possible mesh feasible for inguinal hernia repair. In some embodiments, the barriers and methods are applicable to mesh with or without an element for inserting a tube-like structure therewithin, for non-limiting example, a keyhole. In some embodiments, the barrier and methods are applicable to mesh with or without an element, for non-limiting example, a slit, for sliding or guiding a tube-like structure from an edge of the mesh toward the keyhole like element toward the center of the mesh. In some embodiments, the barrier and methods are applicable to laparoscopic or posterior repairs. In some embodiments, the barrier and methods are applicable to laparoscopic mesh, a mesh plug, a combination of mesh plug and a regular mesh, or a prolene/polyprolene hernia system (PHS) mesh. In some embodiments, the barrier is applied on anterior side only but not at posterior side. In some embodiments, the barrier is completely within an inferomedial section which is 25% of mesh surface area on one side.

The adhesion barrier may be placed along the path of the mesh based on the intended placement of the mesh. As a nonlimiting example, for onlay mesh placement with flat mesh, performed in open fashion, it is typical for the spermatic cord to pierce through a hole within the mesh and lay on top of (anterior to) the mesh for a certain length prior to entering the scrotum. The devices and methods disclosed herein may be configured to limit its interaction with the mesh and the inflammatory reaction that ensues postoperatively. Thus, the neck of the keyhole may be covered with an adhesion barrier along its anterior, posterior, and inner layers. Also, the narrow path of the spermatic cord anterior to the mesh may also be covered with an adhesion barrier. The rest of the mesh, both anteriorly and posteriorly, as well as the edges of the mesh, may be free from adhesion barrier, to maximize adherence to the muscle, fascia, and/or periosteum surrounding it. As another example, in the case of posterior mesh placement, which is typical of laparoscopic or robotic-assisted inguinal hernia repair, the barrier may be limited to a segment of the lower (inferior) portion of the anterior side of the mesh, which may run dorsally in the retroperitoneal space. This may prevent mesh overlap with the narrow portion of the genitofemoral nerve as it pierces the ilioinguinal fold, and in males it may prevent adherence of mesh to the spermatic cord and its contents. The rest of the mesh, both anteriorly and posteriorly, as well as the edges of the mesh, may free from adhesion barrier, to maximize adherence to the muscle, fascia, and/or periosteum surrounding it. As another example, a mesh product with an inlay component, the area of the mesh placed within the inguinal canal and in direct contact with the spermatic cord and its contents and/or genital nerve may be protected with a barrier.

In some embodiments, a barrier protects the critical structures that it contacts from adhesion to the mesh and/or tissue ingrowth to the mesh at least within a certain period of time after the mesh is properly implanted. In some embodiments, the barriers and methods of applying the barriers disclosed herein are applicable to any existing mesh or any other possible mesh feasible for inguinal hernia repair. In some embodiments, the barriers and methods are applicable to mesh with or without an element for inserting a tube-like structure therewithin, for a non-limiting example, a keyhole. In some embodiments, the barriers and methods are applicable to mesh with or without an element (for a nonlimiting example, a slit) for sliding or guiding a tube-like structure from an edge of the mesh toward the keyhole-like element toward the center of the mesh. In some embodiments, the barriers and methods are applicable to laparoscopic or posterior retromuscular repairs. In some embodiments, the barrier and methods are applicable to laparoscopic mesh, a mesh plug, a combination mesh plug and a regular mesh, or a prolene/polyprolene hernia system (PHS) mesh. In some embodiments, the barrier is applied on anterior surface only but not at posterior surface. In some embodiments, the barrier is at inferomedial section of 25% of mesh surface area.

In some embodiments, a barrier as disclosed herein protects the critical structures that it contacts. In some embodiments, a barrier protects the tissue and prevents tissue adhesion to the mesh, scaffold, or other implant which is used in an inguinal hernia repair procedure. In some embodiments, the barriers and methods of applying the barriers disclosed herein are applicable to any existing and future mesh, scaffold, or other implant, whether synthetic or non-synthetic, which is used for inguinal hernia repair.

In some embodiments, the barriers and methods as disclosed herein are applicable to mesh used in both males and females. The barriers and methods are applicable to all mesh with or without an element to allow for the sliding or guiding of a tube-like structure through the mesh, from the keyhole toward the edge of the mesh. As nonlimiting examples, the element includes a slit or strap to form a keyhole, In some embodiments, the barriers and methods are applicable to mesh used in one or more selected from: a) as an onlay, implanted on top of or anterior to the hernia defect, b) as an inlay, implanted within the defect, and c) as a sublay, implanted behind or posterior to the inguinal hernia defect, d) as a combination of any of a), b), and/or c). In some embodiments, the mesh is implanted in open, laparoscopic, or robotic-assisted inguinal hernia repairs. In some embodiments, the barrier is applied on the anterior, posterior, outer, or the inner keyhole surface(s) of the mesh. In some embodiments, there is no barrier along the outer edge of the mesh. In some cases, the barrier is limited to covering only areas that are potentially in contact with critical anatomy which includes but are not limited to the spermatic cord and genitofemoral nerve.

Sizes

The mesh may have any shape or size that is suitable for onlay or sublay implantation for inguinal hernia. The maximal horizontal width of the mesh in the lateral-to-medial direction may be about 0.1 inch to about 15 inches. The maximal vertical height of the mesh in the superior-to-inferior direction may be about 0.5 inch to about 15 inches. Nonlimiting example of mesh sizes include about 1 inch by about 4 inches, about 2 inches by about 4 inches, about 3 inch by about 6 inches, about 4 inch by about 6 inches, about 3 inch by about 5 inches, about 5 inch by about 7 inches, about 1 inch by about 3 inches, about 2.5 inch by about 4.5 inches, or about 3.5 inch by about 5.5 inches.

In some embodiments, the barrier is sized to properly protect the nerve and/or spermatic cord and its contents from contacting the synthetic material or inflammation-inducing material of the mesh. In some embodiments, the barrier is sized to properly protect the tube-like structure from contacting the fabric layer of the mesh.

In some embodiments, the barrier has a shape of one of the following: a rectangle, a triangle, a square, a circle, a tear drop, an oval, a parallelogram, a fan, a trapezoid, a pentagon, a hexagon, an irregular shape, a half circle, a half oval, a parabolic shape, an hour glass shape, a pear shape, or any arbitrary shape.

In some embodiments, the barrier occupies at least 10%, at least 15%, at least 20%, at least 25%, at least 30%, at least 35%, at least 40%, at least 45%, at least 50%, at least 55%, at least about 10%, at least about 15%, at least about 20%, at least about 25%, at least about 30%, at least about 35%, at least about 40%, at least about 45%, at least about 50%, at least about 55%, 10%, 15%, 20%, 25%, 30%, 35%, 40%, 45%, 50%, 55%, about 10%, about 15%, about 20%, about 25%, about 30%, about 35%, about 40%, about 45%, about 50%, about 55%, at most 12%, at most 15%, at most 20%, at most 25%, at most 30%, at most 35%, at most 40%, at most 45%, at most 50%, at most 55%, at most about 12%, at most about 15%, at most about 20%, at most about 25%, at most about 30%, at most about 35%, at most about 40%, at most about 45%, at most about 50%, and/or at most about 55% of the surface area on only one side of the mesh. In some embodiments, when the mesh includes two separate pieces of fabric layers separated by a tube-like mesh connecting element, the barrier occupies at least 10%, at least 15%, at least 20%, at least 25%, at least 30%, at least 35%, at least 40%, at least 45%, at least 50%, at least 55% at least about 10%, at least about 15%, at least about 20%, at least about 25%, at least about 30%, at least about 35%, at least about 40%, at least about 45%, at least about 50%, at least about 55%, 10%, 15%, 20%, 25%, 30%, 35%, 40%, 45%, 50%, 55%, about 10%, about 15%, about 20%, about 25%, about 30%, about 35%, about 40%, about 45%, about 50%, about 55%, at most 12%, at most 15%, at most 20%, at most 25%, at most 30%, at most 35%, at most 40%, at most 45%, at most 50%, at most 55%, at most about 12%, at most about 15%, at most about 20%, at most about 25%, at most about 30%, at most about 35%, at most about 40%, at most about 45%, at most about 50%, and/or at most about 55% of the surface area on any one or both of the separated fabric layers on only one side. In some embodiments, the barrier occupies at one or more of: at least 10%, at least 15%, at least 20%, at least 25%, at least 30%, at least 35%, at least 40%, at least 45%, at least 50%, at least 55%, at least 60%, at least 70%, at least 80%, at least 90%, at least 100%, at least about 10%, at least about 15%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 100%, 10%, 15%, 20%, 25%, 30%, 35%, 40%, 45%, 50%, 55%, 60%, 70%, 80%, 90%, or 100%, about 10%, about 15%, about 20%, about 25%, about 30%, about 35%, about 40%, about 45%, about 50%, about 55%, about 60%, about 70%, about 80%, about 90%, about 100%, at most 12%, at most 15%, at most 20%, at most 25%, at most 30%, at most 35%, at most 40%, at most 45%, at most 50%, at most 55%, at most 60%, at most 70%, at most 80%, at most 90%, at most 100%, at most about 12%, at most about 15%, at most about 20%, at most about 25%, at most about 30%, at most about 35%, at most about 40%, at most about 45%, at most about 50%, and/or at most about 55%, at most about 60%, at most about 70%, at most about 80%, at most about 90%, at most about 100%, of the surface area of the inner surface of the tube-like mesh element.

In some embodiments, the barrier has a maximal height of 1.5 inches. In some embodiments, the barrier has a maximal height of 1.5 inches and a maximal width of 3 inches when the total mesh has a 3 inch height and a 6 inch width. In some embodiments, the barrier has a maximal height of 2 inches and a maximal width of 2 inches when the total mesh has a 4 inch height and a 4 inch width. In some embodiments, the barrier has a maximal height of 0.5 inches to 4 inches. In some embodiments, the barrier has a maximal height of 0.5 to 4 inches and a maximal width of 0.5 to 5 inches when the total mesh has a height about 1.3 times to 3 times the height of the barrier and a width that is 1.3 times to 3 times the width of the barrier.

In some embodiments, the barrier is centered over a "notch" at lower border of the mesh, which signifies the area of the external iliac vessels.

In some embodiments, the mesh includes one or more selected from non-limiting list: a plug, a Prolene Hernia System® mesh, a Kugel mesh hernia patch °, and a Progeria Mesh System®. In some embodiments, the mesh does not include a keyhole-like feature. In some embodiments, the barrier covers the contact area between the tube-like structure and the mesh.

In some cases, the barrier is made of one or more material suitable for anti-adhesion of tissues to the mesh. In some cases, the barrier may have variable materials in different portions of the barrier. In some cases, the barrier may have same combination of materials with different concentrations, different volumes, or other different properties in various portions of the barrier. In some cases, the barrier may have different number or different order of application of sublayers in various portions. In some cases, the various portion of the barrier may be processed differently before or during placements. As non-limiting examples, the process includes a mechanical process, a chemical process, a physical process, a biological process, or a combination thereof. In some cases, the barrier may be removed or added to specified regions of the mesh during or after placement of the mesh to precisely protect specified tissues without adding interferences to other regions or tissues of the body. In some cases, the barrier and its properties may vary over time so that it provides optimal effect during the recovery. In some cases, the barrier may dissolve or be absorbed by the body over time.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, or +/−15%, depending on the embodiment. As a non-limiting example, about 100 meters represents a range of 95 meters to 105 meters, 90 meters to 110 meters, or 85 meters to 115 meters depending on the embodiments. The term "substantially" refers to less than or equal to +/−1%, +/−2%, +/−3%, +/−4%, +/−5%, +/−6%, +/−7%, +/−8%, +/−9%, +/−10%, +/−11%, +/−12%, +/−14%, or +/−15% variation. As a non-limiting example, substantially parallel represents a range of −1 to 1 degree difference, −5 to 5 degree difference, or −15 degrees to 15 degrees of difference from being parallel, depending on the embodiments.

All publications, patents, and patent applications mentioned in this specification are herein incorporated by reference to the same extent as if each individual publication, patent, or patent application was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An implantable mesh for sublay inguinal hernia repair in a male patient, comprising:
    a) a fabric layer comprising an anterior side and a posterior side, wherein the posterior side comprises a surface area that is configured to enable tissue adhesion to the fabric layer; and
    b) an anti-adhesive barrier disposed on and fixed to the anterior side of the fabric layer in a barrier position that is i) inferior to a horizontally-oriented centerline, and ii) medial to a vertically-oriented centerline, wherein a width of an inferior portion of the barrier is greater than a width of a superior portion of the barrier, and wherein the anti-adhesive barrier disposed in the barrier position is configured to prevent adhesion of a spermatic chord and a genital nerve of the male patient to the fabric layer upon implantation of the implantable mesh.

2. The implantable mesh of claim 1, wherein the fabric layer comprises a mesh shape with a curved superior edge and a curved inferior edge, wherein the curved superior edge and the curved inferior edge are configured to (i) join into a pointed lateral edge at a lateral side of the fabric layer, and (ii) join into a curved medial edge at a medial side of the fabric layer.

3. The implantable mesh of claim 1, wherein an inferior edge of the anti-adhesive barrier is disposed above an inferior edge of the fabric layer at a pre-determined distance to enable tissue adhesion to the inferior edge of the fabric layer.

4. The implantable mesh of claim 3, wherein the predetermined distance is about 1 cm.

5. The implantable mesh of claim 1, wherein the barrier is bell-shaped such that a width of the barrier shape increases along a length of the barrier shape extending from a most superior portion of the barrier to a most inferior portion of the barrier.

6. The implantable mesh of claim 5, wherein the barrier is shaped such that the barrier fans out towards a medial edge and an inferior edge of the fabric layer.

7. The implantable mesh of claim 6, wherein the width of the barrier shape gradually increases as the barrier extends toward the medial edge and the inferior edge of the fabric layer.

8. The implantable mesh of claim 1, wherein the barrier covers a part of the surface area on the anterior side of the fabric layer, the part being less than 25%.

9. The implantable mesh of claim 1, wherein at least a portion of the fabric layer is barrier-free, the at least a portion being greater than 75% of the surface area.

10. The implantable mesh of claim 9, wherein the portion of the fabric layer that is barrier-free comprises a first region superior to the horizontally-oriented centerline and a second region lateral to the vertically-oriented centerline.

11. The implantable mesh of claim 1, wherein a portion of the fabric layer is barrier-free, and wherein the portion is (i) at least 25% of a mesh width from a most medial tip of the fabric layer and (ii) inferior to a horizontally-oriented centerline.

12. The implantable mesh of claim 1, wherein a maximal width of the barrier shape is no greater than 50% of a width of the implantable mesh.

13. The implantable mesh of claim 1, wherein the barrier is not oblique with respect to the fabric layer such that a straight line connecting a most superior point of the barrier shape and a midpoint of a most inferior edge of the barrier shape is substantially parallel to a vertically-oriented centerline.

14. The implantable mesh of claim 1, wherein the barrier is not oblique with respect to the fabric layer such that a straight line connecting a most superior point of the barrier shape and a midpoint of a most inferior edge of the barrier shape is substantially orthogonal to a horizontally-oriented centerline.

15. The implantable mesh of claim 1, wherein the mesh is configured to be implanted posterior to a hernia defect, and posterior or deep to a spermatic cord and a genital nerve of the male patient.

16. The implantable mesh of claim 1, further comprising a fin configured to provide femoral space coverage for a femoral hernia, and wherein the fin is (i) barrier-free and (ii) configured to extend inferiorly from an inguinal ligament level of the male patient upon implantation.

17. The implantable mesh of claim 1, wherein the implantable mesh further comprises a keyhole, and wherein the keyhole is configured to accommodate the spermatic cord and the genital nerve of the male patient without constriction.

18. The implantable mesh of claim 1, wherein the fabric layer comprises one or more pores that enable tissue adhesion to the implantable mesh upon implantation in the male patient.

19. The implantable mesh of claim 1, wherein the fabric layer comprises a weave defining interstitial pores, and wherein the weave is configured to enable tailoring of a keyhole without unravelling.

\* \* \* \* \*